(12) United States Patent
Nikolin et al.

(10) Patent No.: US 11,464,852 B2
(45) Date of Patent: Oct. 11, 2022

(54) MODIFIED PEDV SPIKE PROTEIN

(71) Applicant: Boehringer Ingelheim Vetmedica GmbH, Ingelheim am Rhein (DE)

(72) Inventors: Veljko Nikolin, Hannover (DE); Andreas Gallei, Wedemark (DE)

( * ) Notice: Subject to any disclaimer, the term of this patent is extended or adjusted under 35 U.S.C. 154(b) by 172 days.

(21) Appl. No.: 16/575,106

(22) Filed: Sep. 18, 2019

(65) Prior Publication Data

US 2020/0093919 A1 Mar. 26, 2020

(30) Foreign Application Priority Data

Sep. 20, 2018 (EP) .................................... 18195774
Mar. 28, 2019 (EP) .................................... 19165973

(51) Int. Cl.
*A61K 39/225* (2006.01)
*A61P 31/14* (2006.01)
*C12N 15/85* (2006.01)

(52) U.S. Cl.
CPC ............ *A61K 39/225* (2013.01); *A61P 31/14* (2018.01); *C12N 15/85* (2013.01)

(58) Field of Classification Search
None
See application file for complete search history.

(56) References Cited

U.S. PATENT DOCUMENTS

2015/0283229 A1\* 10/2015 Hernandez ............. A61K 45/06
424/186.1

FOREIGN PATENT DOCUMENTS

| CN | 105462936 | \* | 4/2016 |
| CN | 106 148 287 A | | 11/2016 |
| WO | 2016/130569 A1 | | 8/2016 |

OTHER PUBLICATIONS

Kweon et al., Vaccine, 1999, 17:2546-2553. (Year: 1999).*
Opriessnig et al., Veterinary Research, 2017, 48:69. (Year: 2017).*
Database EMBL; Oct. 31, 2012; accession No. AFV59242; XP-002796048.
Database EMBL; Mar. 5, 2013; accession No. AGG34688; XP-002796049.
Database EMBL; Sep. 9, 2012; accession No. AFR11477; XP-002796050.
Database EMBL; Jun. 2, 2017; accession No. ART84226; XP-002796051.
Madu et al., "Characterization of a Highly Conserved Domain within the Severe Acute Respiratory Syndrome Coronavirus Spike Protein S2 Domain with Characteristics of a Viral Fusion Peptide", Journal Virology, 2009, vol. 83 (15), pp. 7411-7421.
Park, Jung-Eun, et al. "Porcine Epidemic Diarrhea Vaccine Evaluation Using a Newly Isolated Strain from Korea." Veterinary Microbiology, vol. 221, 2018, pp. 19-26.
PCT International Search Report (ISR) for related PCT/EP2019/074995 dated Jan. 13, 2020.
Shirato at al., "Mutation in the cytoplasmic retrieval signal of porcine epidemic diarrhea virus spike (S) protein is responsible for enhanced fusion activity", Virus Research, 2011, vol. 161 (2), pp. 188-193.
Ujike & Taguchi, "Incorporation of Spike and Membrane Glycoproteins into Coronavirus Virions", Viruses, 2015, vol. 7, pp. 1700-1725.

\* cited by examiner

*Primary Examiner* — Nicole Kinsey White
(74) *Attorney, Agent, or Firm* — Suzanne Seavello Shope

(57) ABSTRACT

The present invention relates to a nucleic acid molecule encoding a modified porcine epidemic diarrhea virus (PEDV) spike (S) protein and the PEDV (S) protein thereof. Further, the present invention relates to immunogenic compositions comprising said modified PEDV spike protein and methods for immunizing a subject comprising the administration of said immunogenic composition to a subject.

15 Claims, 2 Drawing Sheets

Specification includes a Sequence Listing.

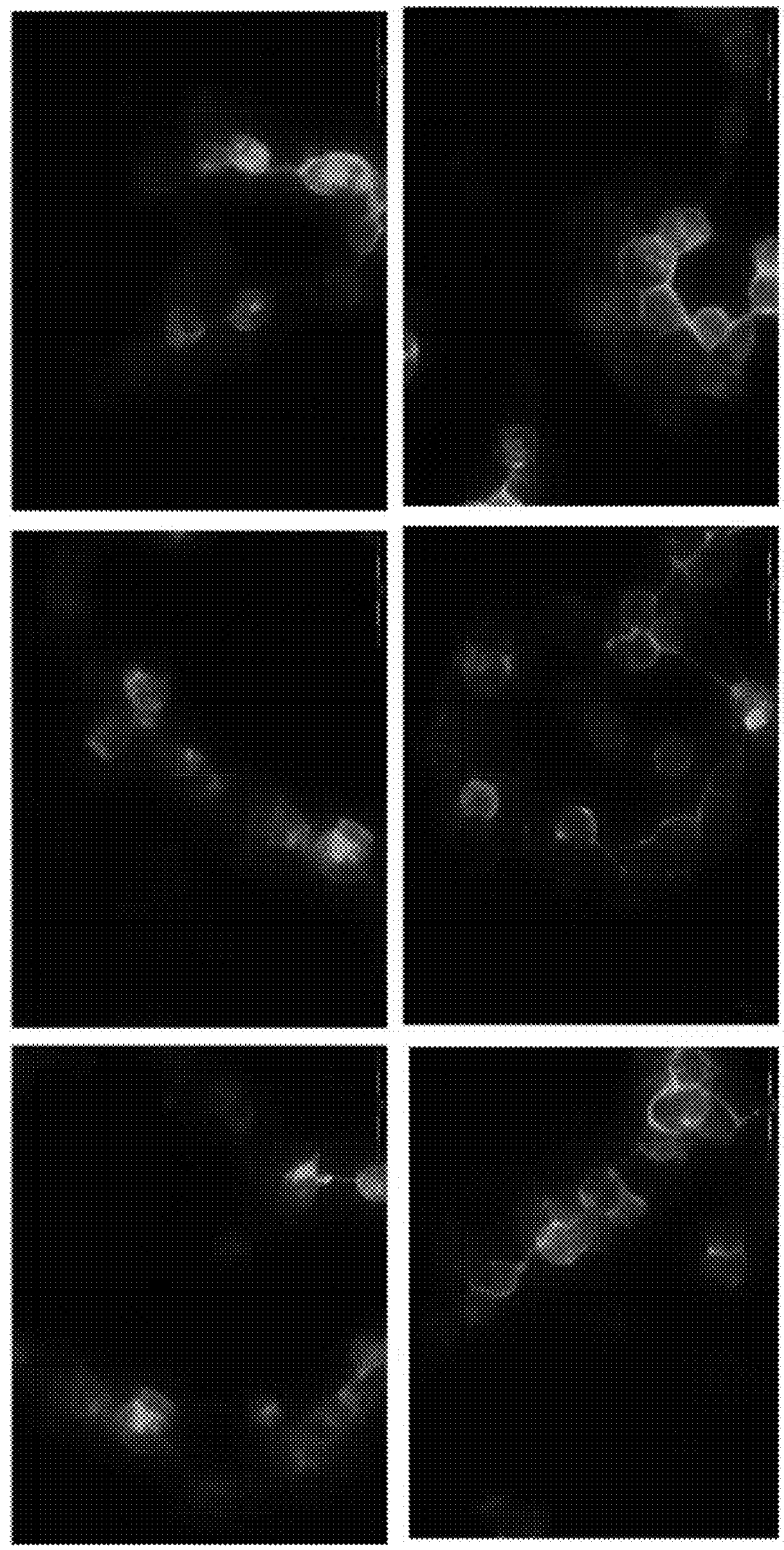

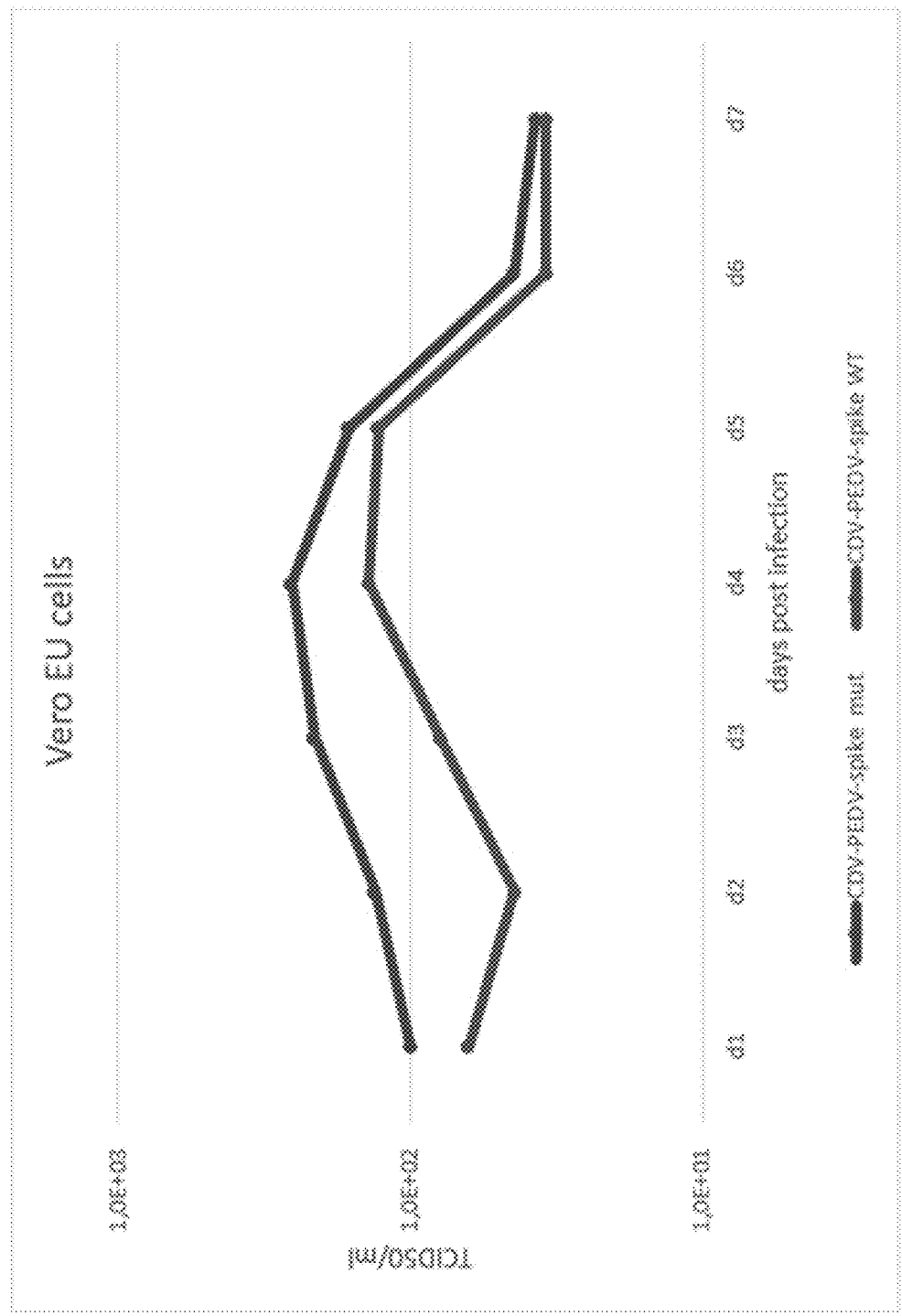

MODIFIED PEDV SPIKE PROTEIN

SEQUENCE LISTING

This application contains a sequence listing in accordance with 37 C.F.R. 1.821-1.825. The sequence listing accompanying this application is hereby incorporated by reference in its entirety.

BACKGROUND OF THE INVENTION

Field of the Invention

The present invention relates to modified PEDV (porcine epidemic diarrhea virus) spike (S) proteins. The modifications result in improved production methods of PEDV vaccines. Further, vaccines comprising the modified Spike proteins are effective as a vaccine and provide protection against PEDV infection or challenge. Due to the high mortality (up to 100%) in less than 10 day old piglets, the disease is of economic concern, for example to the U.S. swine industry.

Description of the Related Art

The porcine epidemic diarrhea virus is an enveloped, positive-sense single-stranded RNA virus that causes acute diarrhea, vomiting, and dehydration in pigs. In pigs three weeks of age and younger, clinical signs (including acute watery, diarrhea, vomiting, and dehydration) can be seen as soon as 24 hours after PEDV infection leading up to 100% mortality. Further, the gross and histological changes in the gut of animals infected with PEDV can cause gross pathological lesions in the small intestine.

PEDV was first identified in Europe but has become increasingly problematic in many Asian countries, including Korea, China, Japan, the Philippines, and Thailand. Since 2013, PEDV emerged in the U.S. and the economic impact of PEDV infection has already been substantial. Accordingly, there is a continuing need to develop vaccines capable of protecting pigs against disease associated with PEDV. In this regard, in particular vaccines are needed that are effective against emerging PEDV strains which could be administered via a mucosal route (oral or intranasal).

Although only one serotype of PEDV has been reported, phylogenetic studies of the S gene show that PEDV can be genetically separated into 2 groups: genogroup 1 (G1; classical) and genogroup 2 (G2; field epidemic or pandemic). Each of the genogroups can be further divided into subgroups (1a and 1b; 2a and 2b). G1a includes the prototype PEDV strain CV777, vaccine strains, and other cell culture-adapted strains, whereas G1b comprises new variants that were first identified in China and later in the United States, South Korea and Europe. G2 comprises global field isolates, which are further clustered into 2a and 2b subgroups (G2a and G2b) responsible for previous local epidemic outbreaks in Asia and recent pandemic outbreaks in North America and Asia, respectively.

PEDV is a member of the subfamily Coronavirinae of genus *Alphacoronavirus*. PEDV is an enveloped virus possessing approximately a 28 kb, positive-sense, single stranded RNA genome, with a 5' cap and a 3' polyadenylated tail. (Pensaert and De Bouck P. 1978). The genome comprises a 5' untranslated region (UTR), a 3' UTR, and at least seven open reading frames (ORFs) that encode four structural proteins (spike (S), envelope (E), membrane (M), and nucleocapsid (N)) and three non-structural proteins (replicases 1a and 1b and ORF3); these are arranged on the genome in the order 5'-replicase (1a/1b)-S-ORF3-E-M-N-3' (Oldham J. 1972; and Bridgen et al. 1993).

The PEDV S protein is a type I glycoprotein, wherein the S protein (of G2b PEDV) is composed of 1,383 amino acids (aa). The S protein can be divided into S1 (e.g., 1-789 aa) and S2 (e.g., 790-1,383 aa) domains based on its homology with S protein of other coronaviruses. The S protein in coronaviruses is a surface antigen, where it plays a role in regulating interactions with host cell receptor glycoproteins to mediate viral entry, and stimulating induction of neutralizing antibodies in the natural host. Thus, the S glycoprotein is a primary target for the development of effective vaccines against PEDV.

Madu et al 2009 (J. Virol.; 83 (15), p. 7411-7421) describe two single mutations (L803A or L804A) in the spike protein of SARS (severe acute respiratory syndrome) and show that each of the single mutations has an impact on membrane fusion activity. Further, Ujike & Taguchi 2015 (Viruses; 7, 1700-1725) describe that mutation of the tyrosine dependent YXXI signal exhibited enhanced cell surface expression. Shirato et al 2011 (Virus Res.; 161 (2):188-93) describe that the mutation H1381R in the KxHxx motif of PEDV results in a transport of the spike protein to the plasma membrane. However, none of said documents disclose that any modifications within the spike protein could improve the production methods of PEDV vaccines and that such produced vaccines with the modifications within the spike protein would still be suitable as a vaccine and provide protection against PEDV infection or challenge.

The solution to the above technical problem is achieved by the description and the embodiments characterized in the claims.

Thus, the invention in its different aspects is implemented according to the claims.

BRIEF DESCRIPTION OF THE DRAWINGS

FIG. 1. Cellular localization of target proteins (PEDV-S2b-wt and PEDV-S2b-mut) in RK13 cells. Three upper panels demonstrate the expression of spike protein launched from EHV1-PEDV-S2b-wt recombinant vector primarily localized in the cytoplasm, while as shown in the three lower panels, PEDV-S expressed from EHV1-PEDV-S2b-mut localized primarily within the cellular membrane.

FIG. 2. Comparison of the growth of the vectors described in Example 3 (CDV-PEDV-spike-MUT (=CDV-PEDV-spike mut) and CDV-PEDV-spike-WT (=CDV-PEDV-spike WT)) in Vero cells, wherein the upper curve relates to CDV-PEDV-spike mut, and the lower curve relates to CDV-PEDV-spike WT.

DETAILED DESCRIPTION OF THE INVENTION

Before the aspects of the present invention are described, it must be noted that as used herein and in the appended claims, the singular forms "a", "an", and "the" include plural reference unless the context clearly dictates otherwise. Thus, for example, reference to "an antigen" includes a plurality of antigens, reference to the "virus" is a reference to one or more viruses and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies as reported in the publications which might be used in connection with the invention. Nothing herein is to be construed as an admission that the invention is not entitled to antedate such disclosure by virtue of prior invention.

The invention is based on the surprising finding that mutations in the amino acid sequence of PEDV spike protein are sufficient to increase the production levels of the vector based PEDV vaccines. Further, animal studies have shown that PEDV vector based vaccines having such a modified spike protein are effective and provide or enable protection against PEDV infection or challenge. Thus, the present invention solves the problems inherent in the prior art and provides a distinct advance in the state of the art.

In this regard, the present invention provides a nucleic acid molecule encoding a porcine epidemic diarrhea virus (PEDV) spike (S) protein comprising the amino acid sequence $$RSX_1IEDX_2X_3, \quad (SEQ\ ID\ NO: 1)$$

wherein (I) $X_2$ is an amino acid residue other than a leucine residue and $X_3$ is a leucine residue, or (II) $X_2$ is a leucine residue and $X_3$ is an amino acid residue other than a leucine residue, or (III) $X_2$ is an amino acid residue other than a leucine residue and $X_3$ is an amino acid residue other than a leucine residue.

In particular, R of the sequence $RSX_1IEDX_2X_3$ (SEQ ID NO:1, and also of any of the sequences SEQ ID NOS: 4, 5, 21-25 and 31-35, is the conserved arginine residue located in C-terminal direction of the S1/S2 cleavage site. Said R is also termed "the conserved arginine residue of the S1/S2 cleavage site of said PEDV S protein" hereinafter. More particular, said R is the arginine residue N-terminally flanking the fusion peptide of said PEDV S protein. The sequence of said fusion peptide generally starts with the sequence SXIED. In particular, said fusion peptide is within the S2 subunit of the PEDV S protein.

The sequence $RSX_1IEDX_2X_3$ (SEQ ID NO:1) is thus also particularly understood to be a sequence of the fusion domain of said PEDV S protein.

More particularly, in the context of the sequence $RSX_1IEDX_2X_3$ (SEQ ID NO:1), and also of any of the sequences SEQ ID NOs: 4, 5, 21-25 and 31-35, R relates to the conserved arginine residue at amino acid position 894 if the PEDV S protein is a genotype 2a (G2a) PEDV S protein, or relates to the conserved arginine residue at amino acid position 891 if the PEDV S protein is a genotype 2b (G2b) PEDV S protein. Thus, with regard to the amino acid position, the statement "R is the conserved arginine residue of the S1/S2 cleavage site of said PEDV S protein" is understood to be equivalent to "R is the arginine residue at amino acid position 894 if the PEDV S protein is a genotype 2a (G2a) PEDV S protein, and wherein the numbering of the amino acid position refers to the amino acid sequence of wild type G2a PEDV S protein, preferably of SEQ ID NO:2 or SEQ ID NO:39, or R is the arginine residue at amino acid position 891 if the PEDV S protein is a genotype 2b (G2b) PEDV S protein and wherein the numbering of the amino acid position refers to the amino acid sequence of wild type G2a PEDV S protein, preferably of SEQ ID NO:3".

Generally, the present invention provides a nucleic acid molecule encoding a porcine epidemic diarrhea virus (PEDV) spike (S) protein comprising the amino acid sequence $$RSX_1IEDX_2X_3, \quad (SEQ\ ID\ NO: 1)$$

wherein R is the conserved arginine residue of the S1/S2 cleavage site of said PEDV S protein, $X_1$ can be any amino acid residue, and wherein (I) $X_2$ is an amino acid residue other than a leucine residue and $X_3$ is a leucine residue, or (II) $X_2$ is a leucine residue and $X_3$ is an amino acid residue other than a leucine residue, or (III) $X_2$ is an amino acid residue other than a leucine residue and $X_3$ is an amino acid residue other than a leucine residue.

The term "nucleic acid molecule" refers to polynucleotides including DNA molecules, RNA molecules, cDNA molecules or derivatives. The term encompasses single as well as double stranded polynucleotides. Preferably, the term refers to single stranded RNA or double stranded cDNA. The nucleic acid of the present invention encompasses isolated polynucleotides (i.e. isolated from its natural context) and genetically modified forms. Moreover, comprised are also chemically modified polynucleotides including naturally occurring modified polynucleotides such as glycosylated or methylated polynucleotides or artificial modified ones such as biotinylated polynucleotides. Further, it is to be understood that the spike proteins as mentioned above may be encoded by a large number of polynucleotides due to the degenerated genetic code. Further, the terms "nucleic acid" and "polynucleotide" are interchangeable and refer to any nucleic acid. The terms "nucleic acid" and "polynucleotide" also specifically include nucleic acids composed of bases other than the five biologically occurring bases (adenine, guanine, thymine, cytosine and uracil).

The term "PEDV" is well known to the person skilled in the art. PEDV stands for porcine epidemic diarrhea virus and is a member of the subfamily Coronavirinae of the genus *Alphacoronavirus*.

The term "spike" refers to a specific protein of the PEDV that is well known by the person skilled in the art. The spike protein is the major inducer of antibodies and protective immune response. Further, the spike protein plays a major role in the cell entry program of PEDV by binding cellular receptors of the host cell and also by mediating virus-cell membrane fusion with the host cell. Further, it is understood that the term "PEDV S protein" is equivalent to the abbreviated term "PEDV S", which is frequently used in the context of PEDV.

The term "protein", "amino acid" and "polypeptide" are used interchangeable. The term "protein" refers to a sequence of amino acids (aa) composed of the natural occurring amino acids as well as derivatives thereof. The naturally occurring amino acids or genetically encoded amino acid residues, respectively, are well known in the art and are described in standard text books of biochemistry. Within the amino acid sequence the amino acids are connected by peptide bonds. Further, the two ends of the amino acid sequence are referred to as the carboxyl terminus (C-terminus) and the amino terminus (N-terminus). The term "protein" encompasses essentially purified proteins or protein preparations comprising other proteins in addition. Further, the term also relates to protein fragments. Moreover, it includes chemically modified proteins. Such modifications may be artificial modifications or naturally occurring modifications such as phosphorylation, glycosylation, myristoylation and the like.

In the context of the present invention, the wording "R is the conserved arginine residue of the S1/S2 cleavage site of said PEDV S protein" is understood be equivalent to "R is the conserved arginine residue located in C-terminal direction of the S1/S2 cleavage site of said PEDV S protein" or is equivalent to "R is the conserved arginine residue N-terminally flanking the fusion peptide of said PEDV S protein", respectively. The wording "N-terminally flanking the fusion peptide" is understood to be equivalent to "N-terminally flanking the fusion peptide sequence".

The sequence $RSX_1IEDX_2X_3$ (SEQ ID NO:1) is to be understood as follows:

R is the conserved arginine residue of the S1/S2 cleavage site of said PEDV S protein, S is the amino acid residue serine, $X_1$ is any of the 20 genetically encoded amino acid residues, I is an isoleucine residue, E is a glutamate residue, D is an aspartate residue, $X_2$ is a variable. $X_2$ has two conditions. $X_2$ can be an amino acid residue other than a leucine (condition 1) which means that $X_2$ can be any of the genetically encoded amino acid residues besides a leucine residue. Alternatively, $X_2$ can be a leucine residue (condition 2), $X_3$ is a variable. $X_3$ has two conditions. $X_3$ can be an amino acid residue other than a leucine residue (condition 1) which means that $X_3$ can be any of the genetically encoded amino acid residues besides leucine. Alternatively, $X_3$ can be a leucine residue (condition 2).

Thus, the present invention provides a nucleic acid molecule encoding a porcine epidemic diarrhea virus (PEDV) spike (S) protein comprising:

a) the amino acid sequence $RSX_1IEDLX_2$ (SEQ ID NO:21), and wherein R is the conserved arginine residue of the S1/S2 cleavage site of said PEDV S protein, $X_1$ can be any amino acid residue, $X_2$ is an amino acid residue other than a leucine residue, or b) the amino acid sequence $RSX_1IEDX_2L$ (SEQ ID NO:22), and wherein R is the conserved arginine residue of the S1/S2 cleavage site of said PEDV S protein, $X_1$ can be any amino acid residue, $X_2$ is an amino acid residue other than a leucine residue, or c) the amino acid sequence $RSX_1IEDX_2X_3$ (SEQ ID NO:1), and wherein R is the conserved arginine residue of the S1/S2 cleavage site of said PEDV S protein, $X_1$ can be any amino acid residue, $X_2$ and $X_3$ are amino acid residues other than leucine residues.

Preferably, the present invention provides a nucleic acid molecule encoding a porcine epidemic diarrhea virus (PEDV) spike (S) protein comprising:

a) the amino acid sequence RSXIEDLA (SEQ ID NO:23), and wherein R is the conserved arginine residue of the S1/S2 cleavage site of said PEDV S protein and X can be any amino acid residue, or b) the amino acid sequence RSXIEDAL (SEQ ID NO:24), and wherein R is the conserved arginine residue of the S1/S2 cleavage site of said PEDV S protein and X can be any amino acid residue, or c) the amino acid sequence RSXIEDAA (SEQ ID NO:25), and wherein R is the conserved arginine residue of the S1/S2 cleavage site of said PEDV S protein and X can be any amino acid residue.

The term "genetically encoded amino acid residue", as described in the context of the present invention, in particular refers to an amino acid residue (single letter code in brackets) selected from the group consisting of alanine residue (A), cysteine residue (C), aspartate residue (D), glutamate residue (E), phenylalanine residue (F), glycine residue (G), histidine residue (H), isoleucine residue (I), lysine residue (K), leucine residue (L), methionine residue (M), asparagine residue (N), proline residue (P), glutamine residue (Q), arginine residue (R), serine residue (S), threonine residue (T), valine residue (V), tryptophan residue (W) and tyrosine residue (Y).

Further, the present invention provides a nucleic acid molecule encoding a porcine epidemic diarrhea virus (PEDV) spike (S) protein selected from the group consisting of the following (a) and (b):

(a) a genotype 2a (G2a) PEDV S protein having at least one mutation, wherein the leucine residue at amino acid position 900 is substituted by an amino acid residue other than a leucine residue, and/or the leucine residue at amino acid position 901 is substituted by an amino acid residue other than a leucine residue, wherein the numbering of the amino acid positions refers to the amino acid sequence of wild type G2a PEDV S protein of SEQ ID NO:2 or SEQ ID NO:39.

(b) a genotype 2b (G2b) PEDV S having at least one mutation, wherein the leucine residue at amino acid position 897 is substituted by an amino acid residue other than a leucine residue, and/or the leucine residue at amino acid position 898 is substituted by an amino acid residue other than a leucine residue, wherein the numbering of the amino acid positions refers to the amino acid sequence of wild type G2b PEDV S protein of SEQ ID NO:3.

Thus, the present invention provides a nucleic acid molecule encoding a porcine epidemic diarrhea virus (PEDV) spike (S) protein selected from the group consisting of the following (a) and (b):

(a) a genotype 2a (G2a) PEDV S protein having at least one mutation, wherein the leucine residue at amino acid position 900 is substituted by an amino acid residue other than a leucine residue and the residue at amino acid position 901 is a leucine residue, or the residue at amino acid position 900 is a leucine residue and the residue at amino acid position 901 is substituted by an amino acid residue other than a leucine residue, or the residues at amino acid positions 900 and 901 are substituted by an amino acid residue other than a leucine residue, wherein the numbering of the amino acid positions refers to the amino acid sequence of wild type G2a PEDV S protein of SEQ ID NO:2 or SEQ ID NO:39;

(b) a genotype 2b (G2b) PEDV S having at least mutation, wherein the leucine residue at amino acid position 897 is substituted by an amino acid residue other than a leucine residue and the residue at amino acid position 898 is a leucine residue, or the residue at amino acid position 897 is a leucine residue and the leucine residue at amino acid position 898 is substituted by an amino acid residue other than a leucine residue, or the residues at amino acid positions 897 and 898 are substituted by an amino acid residue other than a leucine residue, wherein the numbering of the amino acid positions refers to the amino acid sequence of wild type G2b PEDV S protein of SEQ ID NO:3.

As described herein, the wording "the residues at amino acid positions 900 and 901 are substituted by an amino acid residue other than a leucine residue" is equivalent to "the residues at amino acid positions 900 and 901 are each substituted by an amino acid residue other than a leucine residue", and the wording "the residues at amino acid positions 897 and 898 are substituted by an amino acid residue other than a leucine residue" is equivalent to "the residues at amino acid positions 897 and 898 are each substituted by an amino acid residue other than a leucine residue", respectively.

It is further understood that the term "genogroup" is equivalent to the term "genotype" as frequently used in the literature in the context of PEDV. The terms "genotype 2a (G2a)" and "genotype 2b (G2b)" are well known to the person skilled in the art. By phylogenetic studies of the S gene PEDV can be genetically separated into 2 groups: genogroup 1 (G1; classical) and genogroup 2 (G2; field epidemic or pandemic). Each of the genogroups can be further divided into subgroups (1a and 1b; 2a and 2b). G2 comprises global field isolates, which are further clustered into 2a and 2b subgroups responsible for previous local epidemic outbreaks in Asia and recent pandemic outbreaks in North America and Asia, respectively.

The term "wherein the numbering of the amino acid positions refers to the amino acid sequence of wild type G2a PEDV S protein of SEQ ID NO:2 or SEQ ID NO:39" and "wherein the numbering of the amino acid positions refers to the amino acid sequence of wild type G2b PEDV S protein of SEQ ID NO:3" has to be understood that the numbering of amino acid positions refer to the amino acid sequence of full length wild type G2a PEDV S protein (SEQ ID NO:2 or SEQ ID NO:39) and wild type G2b PEDV S protein (SEQ ID NO:3), respectively. Hence, the numbering of the amino positions as mentioned herein is with reference to a wild type G2a PEDV S protein and wild type G2b PEDV S protein sequence having 1388 or 1386, respectively, or 1383 amino acid residues, including a methionine residue at the (N-terminal) amino acid position 1. Thus, the numbering, as used in the context of the present invention, relates to the sequence of a naturally occurring G2a PEDV S protein and wild type G2b PEDV S protein, as set forth in SEQ ID NO:2 or SEQ ID NO:39, respectively, and SEQ ID NO:3. In other words, if reference is made exemplary to the amino acid or residue at position 900, the amino acid residue is meant which corresponds to amino acid 900 of SEQ ID NO:2 or SEQ ID NO:39, respectively. However, this does not mean that the spike proteins according to the invention have the identical amino acid sequence with SEQ ID NO:2 or SEQ ID NO:39, respectively. It only says, that the corresponding amino acids of the spike protein according to the inventions code for the amino acid residue, as explicitly mentioned.

In another specific aspect of the nucleic acid molecule according to the present invention said amino acid residue other than a leucine residue is selected from the group consisting of alanine residue, glycine residue, isoleucine residue, methionine residue and valine residue.

In another specific aspect of the nucleic acid molecule according to the present invention said amino acid residue other than a leucine residue is selected from the group consisting of alanine residue or glycine residue. Thus, the present invention in particular provides a nucleic acid molecule encoding a porcine epidemic diarrhea virus (PEDV) spike (S) protein comprising:

a) the amino acid sequence
(SEQ ID NO: 23)
RSXIEDLA,
or b) the amino acid sequence
(SEQ ID NO: 24)
RSXIEDAL,
or c) the amino acid sequence
(SEQ ID NO: 25)
RSXIEDAA,
or d) the amino acid sequence
(SEQ ID NO: 31)
RSXIEDLG,
or e) the amino acid sequence
(SEQ ID NO: 32)
RSXIEDGL,
or f) the amino acid sequence
(SEQ ID NO: 33)
RSXIEDGG,
or g) the amino acid sequence
(SEQ ID NO: 34)
RSXIEDGA,
or h) the amino acid sequence
(SEQ ID NO: 35)
RSXIEDAG, and wherein R is the conserved arginine residue of the S1/S2 cleavage site of said PEDV S protein and X can be any amino acid residue.

In another specific aspect of the nucleic acid molecule according to the present invention said amino acid residue other than a leucine residue is an alanine residue.

In another specific aspect of the nucleic acid molecule according to the present invention the numbering of the amino acid positions refers to the amino acid sequence RSXIEDLLF (SEQ ID NO:4) of wild type G PEDV S protein, wherein R is the conserved arginine residue of the S1/S2 cleavage site and LL are the amino acid positions 900 and 901 within the genotype 2a (G2a) PEDV S or LL are the amino acid positions 897 and 898 within the genotype 2b (G2b) PEDV S.

In another specific aspect of the nucleic acid molecule according to the present invention said PEDV S protein comprises the amino acid sequence RSXIEDAAF (SEQ ID NO:5), wherein R is the conserved arginine residue of the S1/S2 cleavage site of said PEDV S protein and AA are the amino acid positions 900 and 901 within the genotype 2a (G2a) PEDV S or AA are the amino acid positions 897 and 898 within the genotype 2b (G2b) PEDV S.

In another specific aspect of the nucleic acid molecule according to the present invention said PEDV S protein further comprises the amino acid sequence $$X_1X_2X_3FX_4KX_5X_6X_7X_8, \quad \text{(SEQ ID NO: 6)}$$

wherein $X_8$ is the C-terminal amino acid residue of said PEDV S protein or the amino acid residue at the −2 position relative to the C-terminal amino acid position of said PEDV S protein, $X_2$ to $X_5$, $X_7$ and $X_8$ can be any amino acid residue, and wherein (i) $X_1$ is an amino acid residue other than a tyrosine residue and $X_6$ is a histidine residue, or (ii) $X_1$ is a tyrosine residue and $X_6$ is an amino acid residue other than a histidine residue, or (iii) $X_1$ is an amino acid residue other than a tyrosine residue and $X_6$ is an amino acid residue other than a histidine residue.

Preferably, in the context of the present invention, $X_8$ is the C-terminal amino acid residue of said PEDV S protein if said PEDV S protein is a genotype 2b (G2b) PEDV S protein, or $X_8$ is the amino acid residue at the −2 position relative to the C-terminal amino acid position of said PEDV S protein if said PEDV S protein is a genotype 2a (G2a) PEDV S protein. The term "amino acid residue at the −2 position relative to the C-terminal amino acid position of said PEDV S protein" is understood to be in particular equivalent to" amino acid residue at the amino acid position n-2, wherein n is the amino acid position of the C-terminal amino acid residue of said PEDV S protein". Thus, for instance, if a PEDV protein, such as a genotype 2a (G2a) PEDV S protein, has an amino acid sequence being 1388 amino acid residues in length, then the amino acid residue at the −2 position relative to the C-terminal amino acid position of said PEDV S protein is the amino acid residue at the amino acid position 1386 of said PEDV protein, or of said genotype 2a (G2a) PEDV S protein, respectively. Further, as described herein, it is in particular understood that the wording "$X_2$ to $X_5$, $X_7$ and $X_8$ can be any amino acid residue" is equivalent to "each of $X_2$ to $X_5$, $X_7$ and $X_8$ can be any amino acid residue". Also, it is in particular understood that the wording "$X_2$, $X_3$, $X_4$, $X_5$, $X_6$, $X_7$ can be any amino acid residue" is equivalent to "each of $X_2$, $X_3$, $X_4$, $X_5$, $X_6$ and $X_7$ can be any amino acid residue", "$X_1$, $X_2$, $X_3$, $X_4$, $X_6$, $X_7$ can be any amino acid residue" is equivalent to "each of $X_1$, $X_2$, $X_3$, $X_4$, $X_6$ and $X_7$ can be any amino acid residue", and "$X_2$, $X_3$, $X_4$, $X_5$, $X_7$, $X_8$ can be any amino acid residue" is equivalent to "each of $X_2$, $X_3$, $X_4$, $X_5$, $X_7$ and $X_8$ can be any amino acid residue", respectively.

Advantageously, said modification within the retention signal of the spike protein to $X_1X_2X_3FX_4KX_5X_6X_7X_8$ (SEQ ID NO:6) results in a localization of the spike protein into the plasma membrane.

Furthermore, these modifications improve the production methods of PEDV vaccines. This particularly refers to the stability of the recombinant vectors and in addition may allow the recombinant vector to grow with higher titers in the production cell line due to preventing of biological activities of PEDV spike protein through described mutations.

Further, the present invention provides a nucleic acid molecule encoding a porcine epidemic diarrhea virus (PEDV) spike (S) protein comprising the amino acid sequence $$X_1X_2X_3FX_4KX_5X_6X_7X_8, \quad \text{(SEQ ID NO: 6)}$$

wherein $X_8$ is the C-terminal amino acid residue of said PEDV S protein or the amino acid residue at the −2 position relative to the C-terminal amino acid position of said PEDV S protein, $X_2$ to $X_5$, $X_7$ and $X_8$ can be any amino acid residue, and wherein (i) $X_1$ is an amino acid residue other than a tyrosine residue and $X_6$ is a histidine residue, or (ii) $X_1$ is a tyrosine residue and $X_6$ is an amino acid residue other than a histidine residue, or (iii) $X_1$ is an amino acid residue other than a tyrosine residue and $X_6$ is an amino acid residue other than a histidine residue, and wherein preferably $X_7$ is
the C-terminal amino acid residue of said PEDV S protein
if said PEDV S protein is a genotype 2b (G2b) PEDV S protein, or
the amino acid residue at the −2 position relative to the C-terminal amino acid position of said PEDV S protein
if said PEDV S protein is a genotype 2a (G2a) PEDV S protein.

In another specific aspect of the nucleic acid molecule according to the present invention said PEDV S protein further comprises:

a) the amino acid sequence $X_1X_2X_3FX_4KX_5HX_6X_7$ (SEQ ID NO:26), wherein $X_7$ is the C-terminal amino acid residue of said PEDV S protein or the amino acid residue at the −2 position relative to the C-terminal amino acid position of said PEDV S protein, $X_1$ is an amino acid residue other than a tyrosine residue and $X_2$, $X_3$, $X_4$, $X_5$, $X_6$, $X_7$ can be any amino acid residue, and wherein preferably $X_7$ is
the C-terminal amino acid residue of said PEDV S protein
if said PEDV S protein is a genotype 2b (G2b) PEDV S protein, or
the amino acid residue at the −2 position relative to the C-terminal amino acid position of said PEDV S protein
if said PEDV S protein is a genotype 2a (G2a) PEDV S protein;

or b) the amino acid sequence $YX_1X_2FX_3KX_4X_5X_6X_7$ (SEQ ID NO:27), wherein $X_7$ is the C-terminal amino acid residue of said PEDV S protein or the amino acid residue at the −2 position relative to the C-terminal amino acid position of said PEDV S protein, $X_5$ is an amino acid residue other than a histidine residue and $X_1$, $X_2$, $X_3$, $X_4$, $X_6$, $X_7$ can be any amino acid residue, and wherein preferably $X_7$ is
the C-terminal amino acid residue of said PEDV S protein
if said PEDV S protein is a genotype 2b (G2b) PEDV S protein, or
the amino acid residue at the −2 position relative to the C-terminal amino acid position of said PEDV S protein
if said PEDV S protein is a genotype 2a (G2a) PEDV S protein;

or c) the amino acid sequence $X_1X_2X_3FX_4KX_5X_6X_7X_8$ (SEQ ID NO:6), wherein $X_8$ is the C-terminal amino acid residue of said PEDV S protein or the amino acid residue at the −2 position relative to the C-terminal amino acid position of said PEDV S protein, $X_1$ is an amino acid residue other than a tyrosine residue and $X_6$ is an amino acid residue other than a histidine residue and $X_2$, $X_3$, $X_4$, $X_5$, $X_7$, $X_8$ can be any amino acid residue, and wherein preferably $X_8$ is the C-terminal amino acid residue of said PEDV S protein if said PEDV S protein is a genotype 2b (G2b) PEDV S protein, or the amino acid residue at the −2 position relative to the C-terminal amino acid position of said PEDV S protein if said PEDV S protein is a genotype 2a (G2a) PEDV S protein.

In another specific aspect of the nucleic acid molecule according to the present invention said PEDV S protein further comprises:

a) the amino acid sequence
                       (SEQ ID NO: 28)
AXXFXKXHXX-COOH,
or b) the amino acid sequence
                       (SEQ ID NO: 29)
YXXFXKXRXX-COOH,
or c) the amino acid sequence
                       (SEQ ID NO: 30)
AXXFXKXRXX-COOH, wherein X—COOH is the C-terminal amino acid residue of said PEDV S protein or the amino acid residue at the −2 position relative to the C-terminal amino acid position of said PEDV S protein, and X can be any amino acid residue, and wherein preferably X—COOH is the C-terminal amino acid residue of said PEDV S protein if said PEDV S protein is a genotype 2b (G2b) PEDV S protein, or the amino acid residue at the −2 position relative to the C-terminal amino acid position of said PEDV S protein if said PEDV S protein is a genotype 2a (G2a) PEDV S protein.

In another specific aspect of the nucleic acid molecule according to the present invention, (a) in said G2a PEDV S protein further the tyrosine residue at amino acid position 1377 is substituted by an amino acid residue other than a tyrosine residue, and/or the histidine residue at amino acid position 1384 is substituted by amino acid residue other than a histidine residue, or (b) in said G2b PEDV S protein further the tyrosine residue at amino acid position 1374 is substituted by an amino acid residue other than a tyrosine residue, and/or the histidine residue at amino acid position 1381 is substituted by an amino acid residue other than a histidine residue.

As defined above, the numbering, as used in the context of the present invention, relates to the sequence of a naturally occurring G2a PEDV S protein and wild type G2b PEDV S protein, as set forth in SEQ ID NO:2 or SEQ ID NO:39, respectively, and SEQ ID NO:3.

In another specific aspect of the nucleic acid molecule according to the present invention, (a) in said G2a PEDV S protein further the tyrosine residue at amino acid position 1377 is substituted by an amino acid residue other than a tyrosine residue and the residue at amino acid position 1384 is a histidine residue, or the amino acid residue at amino acid position 1377 is a tyrosine residue and the histidine residue at amino acid position 1384 is substituted by an amino acid residue other than a histidine residue, or the tyrosine residue at amino acid position 1377 is substituted by an amino acid residue other than a tyrosine residue and the histidine residue at amino acid position 1384 is substituted by an amino acid residue other than a histidine residue, or (b) in said G2b PEDV S protein further the tyrosine residue at amino acid position 1374 is substituted by an amino acid residue other than a tyrosine residue and the residue at amino acid position 1381 is a histidine residue, or the residue at amino acid position 1374 is a tyrosine residue and the histidine residue at amino acid position 1381 is substituted by an amino acid residue other than a histidine residue, or the tyrosine residue at amino acid position 1374 is substituted by an amino acid residue other than a tyrosine residue and the histidine residue at amino acid position 1381 is substituted by an amino acid residue other than a histidine residue.

In another specific aspect of the nucleic acid molecule according to the present invention, said amino acid residue other than a tyrosine residue is selected from the group consisting of alanine residue, glycine residue, leucine residue, isoleucine residue, methionine residue and valine residue, and/or said amino acid residue other than a histidine residue is an arginine residue.

In another specific aspect of the nucleic acid molecule according to the present invention, said amino acid residue other than a tyrosine residue is an alanine residue, and/or said amino acid residue other than a histidine residue is an arginine residue.

In another specific aspect of the nucleic acid molecule according to the present invention the numbering of the amino acid positions refers to the amino acid sequence YXXFXKXH (SEQ ID NO:7) of wild type G PEDV S protein, wherein Y and H are the amino acid positions 1377 and 1384 within the genotype 2a (G2a) PEDV S protein or Y and H are the amino acid positions 1374 and 1381 within the genotype 2b (G2b) PEDV S protein.

In another specific aspect of the nucleic acid molecule according to the present invention the nucleic acid molecule comprises a sequence encoding the amino acid sequence AXXFXKXR (SEQ ID NO:8), wherein A and R are the amino acid positions 1377 and 1384 within the genotype 2a (G2a) PEDV S protein or A and R are the amino acid positions 1374 and 1381 within the genotype 2b (G2b) PEDV S protein.

In another specific aspect of the nucleic acid molecule according to the present invention said PEDV S protein:

i) (a) comprises or consists of an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence of any one of SEQ ID NOS: 15, 16, 17, 18, 19, 20, 40, or (b) comprises or consists of an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence of any one of SEQ ID NOS: 9, 10, 11, 12, 13, 14; and/or ii) (a) is encoded by a nucleotide sequence encoding an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence of any one of SEQ ID NOS: 15, 16, 17, 18, 19, 20, 40, or (b) is encoded by a nucleotide sequence encoding an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence of any one of SEQ ID NOS: 9, 10, 11, 12, 13, 14.

The term "identity" or "sequence identity" is known in the art and refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The terms "identity", "sequence identity" and "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package (available at accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention can further be used as a "query sequence" to perform a search against public databases to, for example, to identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information at ncbi.nlm.nih.gov/.

As used herein, it is in particular understood that the term "identical to the sequence of SEQ ID NO:Y" is equivalent to the term "identical to the sequence of SEQ ID NO:Y over the length of SEQ ID NO:Y" or to the term "identical to the sequence of SEQ ID NO:Y over the whole length of SEQ ID NO:Y", respectively. In this context, "Y" is any integer selected from 1 to 40 so that "SEQ ID NO:Y" represents any of the SEQ ID NOs mentioned herein.

In another specific aspect of the nucleic acid molecule according to the present invention said PEDV S protein
(a) comprises the amino acid sequence of any one of SEQ ID NOS: 15, 16, 17, 18, 19, 20, 40, or
(b) comprises the amino acid sequence of any one of SEQ ID NOS: 9, 10, 11, 12, 13, 14.

In an exemplary and non-limiting example the nucleic acid molecule according to the present invention comprises a nucleotide sequence selected from the group consisting of SEQ ID NO:36, SEQ ID NO:37 and SEQ ID NO:38.

Further, the present invention provides a PEDV (S) protein encoded by the nucleic acid molecule as described herein.

In another specific aspect of the nucleic acid molecule or the PEDV S protein according to the present invention said nucleic acid molecule encoding the PEDV S protein or the PEDV S protein is recombinant.

The term "recombinant" as used herein relates to a polynucleotide (including DNA molecules, RNA molecules, cDNA molecules or derivatives) or polypeptide (or protein) having any modifications that do not naturally occur to the corresponding polynucleotide or polypeptide. For instance, a polynucleotide or polypeptide is considered "recombinant" if it contains an insertion, deletion, inversion, relocation or a point mutation introduced artificially, e.g., by human intervention. Therefore, the polynucleotide or polypeptide is not associated with all or a portion of the sequences (polynucleotide or polypeptide) with which it is associated in nature. The term "recombinant" as used with respect to a virus, means a virus produced by artificial manipulation of the viral genome. The term "recombinant virus" encompasses genetically modified viruses.

Preferably, the protein of the present invention is a non-naturally-occurring protein.

Preferably, said protein is an isolated polypeptide.

Further, the present invention provides a polynucleotide comprising the nucleic acid molecule as described herein.

Production of the nucleic acid molecule and polynucleotides described herein is within the skill in the art and can be carried out according to recombinant techniques described, among other places, in Sam brook et al., 2001, Molecular Cloning, A Laboratory Manual, Cold Spring Harbor Laboratory Press, Cold Spring Harbor, N.Y.; Amusable, et al., 2003, Current Protocols In Molecular Biology, Greene Publishing Associates & Wiley Interscience, NY; Innis et al. (eds), 1995, PCR Strategies, Academic Press, Inc., San Diego; and Erlich (ed), 1994, PCR Technology, Oxford University Press, New York, all of which are incorporated herein by reference.

Further, the present invention provides a vector comprising the nucleic acid molecule as described herein or the polynucleotide as described herein.

The term "vector" as it is known in the art refers to a polynucleotide construct, typically a plasmid or a bacterial artificial chromosome, used to transmit genetic material to a host cell. Vectors can be, for example, bacteria, viruses, phages, bacterial artificial chromosomes, cosmids, or plasmids. A vector as used herein can be composed of or contain either DNA or RNA. In some embodiments, a vector is composed of DNA. In some embodiments a vector is an infectious virus. Such a viral vector contains a viral genome which was manipulated in a way that it carries a foreign gene which has no function in the replication of the viral vector neither in cell culture nor in a host animal. According to specific aspects of the present disclosure a vector may be used for various aspects such as mere transmission of genetic material, for the transfection of host cells or organisms, for use as vaccines, e.g. DNA vaccines or for gene expression purposes. Gene expression is a term describing the biosynthesis of a protein in a cell as directed by a specific polynucleotide sequence called gene. In a specific aspect a vector may be an "expression vector", which is a vector that is capable of directing the expression of a protein encoded by one or more genes carried by the vector when it is present in the appropriate environment.

Vectors and methods for making and/or using vectors (or recombinants) for expression can be by or analogous to the methods disclosed in: U.S. Pat. Nos. 4,603,112, 4,769,330, 5,174,993, 5,505,941, 5,338,683, 5,494,807, 4,722,848, 5,942,235, 5,364,773, 5,762,938, 5,770,212, 5,942,235, 382, 425, PCT publications WO 94/16716, WO 96/39491, WO 95/30018; Paoletti, "Applications of pox virus vectors to vaccination: An update, "PNAS USA 93: 11349-11353, October 1996; Moss, "Genetically engineered poxviruses for recombinant gene expression, vaccination, and safety," PNAS USA 93: 11341-11348, October 1996; Smith et al., U.S. Pat. No. 4,745,051(recombinant baculovirus); Richardson, C. D. (Editor), Methods in Molecular Biology 39, "Baculovirus Expression Protocols" (1995 Humana Press Inc.); Smith et al., "Production of Human Beta Interferon in Insect Cells Infected with a Baculovirus Expression Vector", Molecular and Cellular Biology, December, 1983, Vol. 3, No. 12, p. 2156-2165; Pennock et al., "Strong and Regulated Expression of *Escherichia coli* B-Galactosidase in Infect Cells with a Baculovirus vector, "Molecular and Cellular Biology March 1984, Vol. 4, No. 3, p. 406; EPAO 370 573; U.S. application No. 920,197, filed Oct. 16, 1986; EP Patent publication No. 265785; U.S. Pat. No. 4,769,331 (recombinant herpesvirus); Roizman, "The function of herpes simplex virus genes: A primer for genetic engineering of novel vectors," PNAS USA 93:11307-11312, October 1996; Andreansky et al., "The application of genetically engineered herpes simplex viruses to the treatment of experimental brain tumors," PNAS USA 93: 11313-11318, October 1996; Robertson et al., "Epstein-Barr virus vectors for gene delivery to B lymphocytes", PNAS USA 93: 11334-11340, October 1996; Frolov et al., "Alphavirus-based expression vectors: Strategies and applications," PNAS USA 93: 11371-11377, October 1996; Kitson et al., J. Virol. 65, 3068-3075, 1991; U.S. Pat. Nos. 5,591,439, 5,552,143; WO 98/00166; allowed U.S. application Ser. No. 08/675, 556, and 08/675,566 both filed Jul. 3, 1996 (recombinant adenovirus); Grunhaus et al., 1992, "Adenovirus as cloning vectors," Seminars in Virology (Vol. 3) p. 237-52, 1993; Ballay et al. EMBO Journal, vol. 4, p. 3861-65, Graham, Tibtech 8, 85-87, April, 1990; Prevec et al., J. Gen Virol. 70, 42434; PCT WO 91/11525; Felgner et al. (1994), J. Biol. Chem. 269, 2550-2561, Science, 259: 1745-49, 1993; and McClements et al., "Immunization with DNA vaccines encoding glycoprotein D or glycoprotein B, alone or in combination, induces protective immunity in animal models of herpes simplex virus-2 disease", PNAS USA 93: 11414-11420, October 1996; and U.S. Pat. Nos. 5,591,639, 5,589, 466, and 5,580,859, as well as WO 90/11092, WO93/19183, WO94/21797, WO95/11307, WO95/20660; Tang et al., Nature, and Furth et al., Analytical Biochemistry, relating to DNA expression vectors, inter alia. See also WO 98/33510; Ju et al., Diabetologia, 41: 736-739, 1998 (lentiviral expression system); Sanford et al., U.S. Pat. No. 4,945,050; Fischbach al. (Intracel); WO 90/01543; Robinson et al., Seminars in Immunology vol. 9, pp. 271-283 (1997), (DNA vector systems); Szoka et al., U.S. Pat. No. 4,394,448 (method of inserting DNA into living cells); McCormick et al., U.S. Pat. No. 5,677,178 (use of cytopathic viruses); and U.S. Pat. No. 5,928,913 (vectors for gene delivery); as well as other documents cited herein.

Preferably, said vector is a viral vector.

The term "viral vector" describes a genetically modified virus which was manipulated by recombinant DNA technique in a way so that its entry into a host cell results in a specific biological activity, e.g. the expression of a transgene carried by the vector. In a specific aspect the transgene is an antigen. A viral vector may or may not be replication competent in the target cell, tissue, or organism. It is in particular understood, that the term "viral vector", as used herein, is equivalent to the term "virus vector".

Generation of a viral vector can be accomplished using any suitable genetic engineering techniques well known in the art, including, without limitation, the standard techniques of restriction endonuclease digestion, ligation, transformation, plasmid purification, DNA sequencing, transfection in cell cultures, for example as described in Sambrook et al. (Molecular Cloning: A Laboratory Manual. Cold Spring Harbor Laboratory Press, N.Y. (1989)) or K. Maramorosch and H. Koprowski (Methods in Virology Volume VIII, Academic Press Inc. London, UK (2014)).

A viral vector can incorporate sequences from the genome of any known organism. The sequences can be incorporated in their native form or can be modified in any way to obtain a desired activity. For example, the sequences can comprise insertions, deletions or substitutions.

In a specific aspect of the vector according to the present invention the vector is a CDV (Canine Distemper Virus), EHV (Equine Herpes Virus) or ORF virus (a parapox virus), PRV (pseudorabies virus), CAV (canine adenovirus), PCMV (porcine cytomegalovirus) or BoHV-4 (bovine herpesvirus-4).

In a specific aspect of the vector according to the present invention the vector is a CDV or EHV.

Further, the present invention provides an immunogenic composition comprising the nucleic acid molecule encoding the PEDV S protein as described herein and/or the PEDV S protein as described herein and/or the vector as described herein.

The term "immunogenic composition" refers to a composition that comprises at least one antigen, which elicits an immunological response in the host to which the immunogenic composition is administered. Such immunological response may be a cellular and/or antibody-mediated immune response to the immunogenic composition of the invention. Preferably, the immunogenic composition induces an immune response and, more preferably, confers protective immunity against one or more of the clinical signs of a PEDV infection. The host is also described as "subject". Preferably, any of the hosts or subjects described or mentioned herein is a piglet, pig or sow.

Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the immunogenic composition of the invention. Preferably, the host will display either a protective immunological response or a therapeutically response.

A "protective immunological response" or "protective immunity" will be demonstrated by either a reduction or lack of clinical signs normally displayed by an infected host, a quicker recovery time and/or a lowered duration of infectivity or lowered pathogen titer in the tissues or body fluids or excretions of the infected host.

In case where the host displays a protective immunological response such that resistance to new infection will be enhanced and/or the clinical severity of the disease reduced, the immunogenic composition is described as a "vaccine".

In another specific aspect of the immunogenic composition according to the present invention the immunogenic composition further comprises a pharmaceutically acceptable carrier.

The term "pharmaceutical-acceptable carrier" includes any and all solvents, dispersion media, coatings, stabilizing agents, diluents, preservatives, antibacterial and antifungal agents, isotonic agents, adsorption delaying agents, adjuvants, immune stimulants, and combinations thereof.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

In one aspect of the present invention the pharmaceutically acceptable carrier is phosphate buffered saline.

Preferably, the immunogenic composition further comprises sucrose gelatin stabilizer.

In one aspect of the present invention the pharmaceutically acceptable carrier is chitosan.

Chitosan is a natural deacetylated polysaccharide from chitin in crustaceans (e.g., shrimp, crab), insects, and other invertebrates. Recently, Rauw et al. 2009 (Vet Immunol Immunop 134:249-258) demonstrated that chitosan enhanced the cellular immune response of live Newcastle disease vaccine and promoted its protective effect. Further, Wang et al., 2012 (Arch Virol (2012) 157:1451-1461) have shown results revealing the potential of chitosan as an adjuvant for use in a live attenuated influenza vaccine.

Preferably, the immunogenic composition can further include one or more other immunomodulatory agents such as, e.g. interleukins, interferons, or other cytokines. The amounts and concentrations of adjuvants and additives useful in the context of the present invention can readily be determined by the skilled artisan.

In some aspects, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed.Stewart-Tull, D. E. S.), JohnWiley and Sons, NY, pp51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Carbopol 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIM adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from E. coli (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 µg to about 10 mg per dose, preferably in an amount of about 100 µg to about 10 mg per dose, more preferably in an amount of about 500 µg to about 5 mg per dose, even more preferably in an amount of about 750 µg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

In another specific aspect of the immunogenic composition according to the present invention the immunogenic composition is a vaccine. The term "vaccine" already has been described elsewhere herein. However, in case where the host displays a protective immunological response such that resistance to new infection will be enhanced and/or the clinical severity of the disease reduced, the immunogenic composition is described as a "vaccine.

Further, the present invention provides a cell comprising the nucleic acid molecule as described herein, the polynucleotide as described herein or the vector as described herein.

Further, the present invention provides a method of producing the nucleic acid molecule encoding the PEDV S protein as described herein and/or the PEDV S protein as described herein, comprising transfecting a cell with the vector as described herein.

Further, the present invention provides a method of preparing an immunogenic composition for the treatment and/or prophylaxis of PEDV infections in a subject comprising:

a.) infecting a cell with the vector as described herein;
b.) obtaining said vector; and
c.) addition of a pharmaceutically acceptable carrier.

The term "obtaining" comprises the harvest, isolation, purification and/or formulation (e.g. finishing, inactivation and/or blending) of the antigen.

The term "harvest" refers to collecting or recovering said vector from the transfected cell or cell line. Any conventional method known in the art can be used to recover said vector, e.g. any separation method. Well known methods in the art comprise centrifugation or filtration, such as using a semi-permeable membrane having a certain pore size.

The term "isolation" comprises an isolation step of said vector. Methods for the isolation of said vector from the infected cell or cell line are known to a person skilled in the art. Those methods comprise physical and/or chemical methods, including but are not limited to freeze thaw cycles, treatment with ultrasound and the alike.

Methods for the "purification" of said vector from the isolate are known to a person skilled in the art, for example by those methods described in Protein purification methods—a practical approach (E. L. V. Harris and S. Angel, eds., IRL Press at Oxford University Press). Those methods include, but are not limited to, separation by centrifugation and/or filtration, precipitation, size exclusion (gel filtration) chromatography, affinity chromatography, metal chelate chromatography, ion-exchange chromatography covalent chromatography, hydrophobic interaction chromatography, and the alike. The vector can be obtained in a purified pure form, or free or substantially free of other cellular materials or culture medium etc. After said isolation and/or purification the antigen exhibits a purity of at least 80%, preferably 80%-90%, more preferably 90%-97%, most preferred more than 97% up to an absolute pure form without any contamination.

According to a further aspect, "obtaining" as used herein may also include further finishing steps as part of the final formulation process, like the addition of buffer, inactivation, neutralization steps and the alike.

Preferably, the cell is from an eukaryotic cell line.

In a specific aspect of the method according to the present invention the cell is a Vero cell, ST cell or BHK-21, Ma104, MDBK, RK13, MDCK or PK15.

All mentioned cell lines are well known to the person skilled in the art and are public available. Vero cells are exemplarily deposited at the American Tissue Culture Collection under accession number ATCC CCL-81. ST cells are exemplarily deposited at the American Tissue Culture Collection under accession number CRL-1746. BHK-21 cells are exemplarily deposited at the American Tissue Culture Collection under accession number ATCC CCL-10. MDCK cells are exemplarily deposited at the American Tissue Culture Collection under accession number ATCC CCL-34 or ATCC CRL-2285.

In another specific aspect of the immunogenic composition or the method according to the present invention said pharmaceutically acceptable carrier is selected from the group consisting of solvents, dispersion media, coatings, stabilizing agents, diluents, preservatives, antibacterial and antifungal agents, isotonic agents, adsorption delaying agents, adjuvants, immune stimulants, and combinations thereof.

Further, the present invention provides a method of immunizing a subject comprising administering to such subject an immunogenic composition as described herein.

Advantageously, the immunogenic composition of the present invention has been proven to be safe and efficacious.

The term "immunizing" relates to an active immunization by the administration of an immunogenic composition to a subject to be immunized, thereby causing an immunological response against the antigen included in such immunogenic composition.

Preferably, immunization results in lessening of the incidence of the particular PEDV infection in a herd or in the reduction in the severity of clinical signs caused by or associated with the particular PEDV infection.

Further, the immunization of a subject in need with the immunogenic compositions as provided herewith, results in preventing infection of a subject by PEDV infection. Even more preferably, immunization results in an effective, long-lasting, immunological-response against PEDV infection. It will be understood that the said period of time will last more than 1 month, preferably more than 2 months, preferably more than 3 months, more preferably more than 4 months, more preferably more than 5 months, more preferably more than 6 months. It is to be understood that immunization may not be effective in all subjects immunized. However, the term requires that a significant portion of subjects in a herd are effectively immunized.

Preferably, a herd of subjects is envisaged in this context which normally, i.e. without immunization, would develop clinical signs normally caused by or associated with a PEDV infection. Whether the subjects of a herd are effectively immunized can be determined without further ado by the person skilled in the art. Preferably, the immunization shall be effective if clinical signs in at least 33%, at least 50%, at least 60%, at least 70%, at least 80%, at least 90%, still more preferably in at least 95% and most preferably in 100% of the subjects of a given herd are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not immunized or immunized with an immunogenic composition that was available prior to the present invention but subsequently infected by the particular PEDV.

Further, the present invention provides a method of treating and/or preventing clinical signs caused by PEDV infection in a subject of need, the method comprising administering to the subject a therapeutically effective amount of an immunogenic composition as described herein.

Advantageously, the immunogenic composition of the present invention has been proven to reduce the clinical signs caused by PEDV infection.

The term "treating and/or preventing" refers to the lessening of the incidence of the particular PEDV infection in a herd or the reduction in the severity of clinical signs caused by or associated with the particular PEDV infection. Thus, the term "treating and/or preventing" also refers to the reduction of the number of subjects in a herd that become infected with the particular PEDV (=lessening of the incidence of the particular PEDV infection) or to the reduction of the severity of clinical signs normally associated with or caused by a PEDV infection or the reduction of virus shedding after infection with the particular PEDV or preventing or reducing diarrhea after infection with the particular PEDV in a group of subjects which subjects have received an effective amount of the immunogenic composition as provided herein in comparison to a group of subjects which subjects have not received such immunogenic composition.

The "treating and/or preventing" generally involves the administration of an effective amount of the immunogenic composition of the present invention to a subject or herd of subjects in need of or that could benefit from such a treatment/prophylaxis. The term "treating" refers to the administration of the effective amount of the immunogenic composition once the subject or at least some subjects of the herd is/are already infected with such PEDV and wherein such subjects already show some clinical signs caused by or associated with such PEDV infection. The term "preventing" refers to the administration of a subject prior to any infection of such subject with PEDV or at least where such subject or none of the subjects in a group of subjects do not show any clinical signs caused by or associated with the infection by such PEDV. The terms "prophylaxis" and "preventing" are used interchangeable in this application.

The term "an effective amount" as used herein means, but is not limited to an amount of antigen, that elicits or is able to elicit an immune response in a subject. Such effective amount is able to lessen the incidence of the particular PEDV infection in a herd or to reduce the severity of clinical signs of the particular PEDV infection.

Preferably, clinical signs are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not treated or treated with an immunogenic composition that was available prior to the present invention but subsequently infected by the particular PEDV.

The term "clinical signs" as used herein refers to signs of infection of a subject from PEDV. Examples for such clinical signs include but are not limited to virus load, diarrhea, shedding, increased body temperature, mortality, gross pathological lesions in the intestine, depression, weight loss, reduced growth rates and reduced appetite. However, the clinical signs also include but are not limited to clinical signs that are directly observable from a live animal. Examples for clinical signs that are directly observable from a live animal include weight loss, reduced growth rates, reduced appetite, dehydration, watery diarrhea, vomiting, lameness, lethargy, wasting and unthriftiness and the like.

Preferably, the clinical signs lessened in incidence or severity in a treated subject compared to subjects that are either not treated or treated with an immunogenic composition that was available prior to the present invention but subsequently infected by the particular PEDV refer to a reduction in weight loss, a lower virus load, a reduction of diarrhea, a reduced shedding, a reduced rectal temperature, mortality, reduced gross pathological lesions in the intestine, or combinations thereof.

The term "in need" or "of need", as used herein means that the administration/treatment is associated with the boosting or improvement in health or clinical signs or any other positive medicinal effect on health of the subjects which receive the immunogenic composition in accordance with the present invention.

Further, the present invention provides a method of reducing the diarrhea in a subject in comparison to a subject of a non-immunized control group of the same species, the method comprising administering to the subject a therapeutically effective amount of an immunogenic composition as described herein.

Further, the present invention provides a method of reducing the mortality in a subject in comparison to a subject of a non-immunized control group of the same species, the method comprising administering to the subject a therapeutically effective amount of an immunogenic composition as described herein.

The term "reducing the mortality" means that the mortality is reduced by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, even more preferably by at least 90%, still more preferably by at least 95% most preferably by 100% in comparison to subjects that are not treated (not immunized) but subsequently infected by the particular PEDV.

Thus, it has to be understood that a subject can be vaccinated with the immunogenic composition according to the present invention for reducing or preventing clinical signs such as diarrhea or mortality in said subject. Preferably, said subject is a piglet, pig or sow.

Further, the present invention provides a method for inducing the production of antibodies specific for PEDV in a subject, wherein said method comprises administering the immunogenic composition as described herein to said subject. Preferably, said subject is a piglet, pig or sow.

Further, the present invention provides a method for inducing the production of antibodies specific for PEDV in a sow, wherein said method comprises administering the immunogenic composition as described herein to said sow.

The term "antibodies specific for PEDV" refers to detectable anti-PEDV antibodies. Further, the anti-PEDV antibodies in the sow have been developed in response to the vaccination with the PEDV vaccine according to the present invention. The term "antibodies specific for PEDV" or "antibodies specific for PEDV in a sow" shall further mean, but is not limited to, a sow that has a detectable anti-PEDV antibody titer, preferably of at least 1:10, more preferably of more than 1:20, even more preferably of more than 1:40, even more preferably of more than 1:80, even more preferably of 1:160, even more preferably of more than 1:320, and most preferably of more than 1:640. Preferably, that anti-PEDV antibody titer is detectable and quantifiable in a specific anti-PEDV immune assay.

Advantageously, the immunogenic composition of the present invention has been shown to induce the production of antibodies specific for PEDV in a sow.

It is well known by the person skilled in the art how to detect the production of antibodies specific for PEDV such as by an ELISA Assay (ELISAs are commercially available).

Further, the present invention provides a method of reducing the diarrhea in a piglet in comparison to a piglet of a non-immunized control group, the method comprising administering to the sow of the piglet a therapeutically effective amount of an immunogenic composition as described herein, wherein the piglet is to be suckled by said sow. The term "sow of the piglet", as used herein, is in particular understood to be equivalent to "mother sow of the piglet" or "nurse sow of the piglet", respectively.

Further, the present invention provides a method of reducing the mortality in a piglet in comparison to a piglet of a non-immunized control group, the method comprising administering to the sow of the piglet a therapeutically effective amount of an immunogenic composition as described herein, wherein the piglet is to be suckled by said sow.

Further, the present invention provides a method of reducing or preventing the clinical signs or disease caused by an infection with a PEDV in a piglet, wherein the piglet is to be suckled by a sow to which the immunogenic composition as described herein has been administered.

Preferably, the clinical sign that is reduced is mortality. Thus, the present invention also provides a method of reducing the mortality caused by an infection with a PEDV in a piglet, wherein the piglet is to be suckled by a sow to which the immunogenic composition as described herein has been administered.

Further, the present invention provides a method of reducing or preventing the clinical signs or disease caused by an infection with a PEDV in a piglet, wherein said method comprises
  administering the immunogenic composition as described herein to a sow, and
  allowing said piglet to be suckled by said sow or, respectively, allowing said piglet to suckle said sow.

Advantageously, the immunogenic composition of the present invention has been shown to reduce clinical signs in pigs when administered to sows during pregnancy.

In case piglets are vaccinated with the immunogenic composition of the present invention it has to be understood that time is needed for actual antibody production in said piglet. Therefore, in another aspect of the method present invention the sow being pregnant is vaccinated with the immunogenic composition of the present invention. Said vaccination results in the production of antibodies specific for PEDV in said sow. The maternally derived antibodies from said sow are then passively transferred to the newborn piglets via colostrum and/or milk.

In another specific aspect of the method according to the present invention said sow to which the immunogenic composition is administered is a sow being pregnant, in particular with said piglet. However, it is to be understood that the piglet can be suckled by any sow giving colostrum or milk, wherein said sow is in particular a sow to which said immunogenic has been administered.

In another specific aspect the method according to the present invention comprising the steps of
  administering the immunogenic composition as described herein to a sow being pregnant with said piglet,
  allowing said sow to give birth to said piglet, and
  allowing said piglet to be suckled by said sow.

In another specific aspect of the method according to the present invention said method results in an improvement in a clinical sign or efficacy parameter selected from the group consisting of: a reduction in weight loss, a lower virus load, a reduction of diarrhea, a reduced shedding, a reduced rectal temperature, reduced mortality, reduced gross pathological lesions in the intestine, or combinations thereof, in comparison to a subject of a non-immunized control group of the same species.

In another specific aspect of the method according to the present invention said subject is a piglet, pig or sow.

Preferably, the immunogenic composition is administered to the subject within the first two months of age, more preferably, within the first month of age.

In another specific aspect of the method according to the present invention the immunogenic composition is administered to the subject within the first month of age.

Thus, it has to be understood that the immunogenic composition can be administered to the subject exemplary within the first three weeks of age or within the first two weeks of age.

In another specific aspect of the method according to the present invention said immunogenic composition is administered to sows during pregnancy and lactation.

Advantageously, the immunogenic composition of the present invention has been proven to be safe when administered to sows during pregnancy.

Thus, there is provided a method of vaccinating pigs against PEDV by administering the PEDV vaccine according to the present invention to a pregnant sow at least two times before farrowing, preferably three times before farrowing, more preferably two times before farrowing ("repeated doses"). Preferably, the pregnant sow is vaccinated with the PEDV vaccine according to the present invention twice with a single dose of said vaccine before farrowing. However, when the vaccine is administered to the sow two times, the first administration should occur between 12 and 4 weeks before farrowing, more preferably between 9 and 5 weeks before farrowing. The second administration should occur between 8 and 1 week before farrowing, more preferably between 6 and 1 week before farrowing.

In another specific aspect of the method according to the present invention the immunogenic composition is administered at two or more doses.

Advantageously, the immunogenic composition of the present invention has been shown to induce the production of antibodies specific for PEDV after two doses.

In another specific aspect of the method according to the present invention said immunogenic composition is administered to sows two times, the first administration between 9 and 5 weeks before farrowing and the second administration between 6 and 1 week before farrowing.

The immunogenic composition is, preferably, administered topically or systemically. Suitable routes of administration conventionally used are oral or parenteral administration, such as intranasal, intravenous, intramuscular, intraperitoneal, subcutaneous, as well as inhalation. However, depending on the nature and mode of action of a compound, the immunogenic composition may be administered by other routes as well. However, most preferred the immunogenic composition is administered intranasal or oral.

In another specific aspect of the method according to the present invention said immunogenic composition is administered intranasal, mucosal, oral, intradermal or intramuscular.

Advantageously, the immunogenic composition of the present invention has been proven to be effective when administered intranasal.

In another specific aspect of the method according to the present invention said immunogenic composition is administered intranasal or oral.

Preferably, the immunogenic composition comprises between $1\times10^2$ to $1\times10^9$ $TCID_{50}$/ml, more preferably between $1\times10^3$ to $1\times10^7$ $TCID_{50}$/ml and most preferably between $1\times10^4$ to $1\times10^6$ $TCID_{50}$/ml.

In another specific aspect of the method according to the present invention the immunogenic composition comprises between $1\times10^3$ to $1\times10^7$ $TCID_{50}$/ml.

The term "$TCID_{50}$/ml" refers to the measure of infectious virus titer. Specifically the tissue culture infectious dose fifty per milliliter ($TCID_{50}$/ml) gives the dilution of a virus preparation at which 50% of a number of cell cultures inoculated in parallel with that dilution are infected.

In another specific aspect of the method according to the present invention the method results in a reduction of the shedding from day 2 after challenge or infection.

In another specific aspect of the method according to the present invention the method results in a reduction of the shedding from day 3 after challenge or infection.

In another specific aspect of the method according to the present invention the method results in a reduction of the shedding from day 4 after challenge or infection.

In another specific aspect of the method according to the present invention the method results in a reduction of the shedding from day 5 after challenge or infection.

In another specific aspect of the method according to the present invention the method results in a reduction of the shedding from day 7 after challenge or infection.

In another specific aspect of the method according to the present invention the method results in a reduction of the shedding from day 10 after challenge or infection.

In another specific aspect of the method according to the present invention the method results in a reduction of the shedding from day 5, 7 or 10 after challenge or infection.

Advantageously, the immunogenic composition of the present invention has been proven to reduce the shedding after infection or challenge.

The term "reduction of the shedding" means that the shedding is reduced by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, even more preferably by at least 90%, still more preferably by at least 95% most preferably by 100% in comparison to subjects that are not treated (not immunized) but subsequently infected by the particular PEDV. It is in the general knowledge of a person skilled in the art how to measure the viral shedding.

The term "shedding" refers to secretions of PEDV in fecal discharges or feces. Thus, shedding may be determined by examining the virus titer in fecal discharges, feces or rectal swaps. The term "shedding" further encompasses the transfer of virus to susceptible animals (i.e. sentinels). It is in the general knowledge of a person skilled in the art how to measure the viral shedding such as by PCR, qPCR or ELISA.

In another specific aspect of the method according to the present invention the method increases the protection against a homologous challenge.

Advantageously, the immunogenic composition of the present invention has been proven to be protective after challenge.

The invention provides the use of the nucleic acid molecule encoding a porcine epidemic diarrhea virus (PEDV) spike (S) protein, the PEDV (S) protein or the or immunogenic composition as described herein for the manufacture of a medicament.

The invention also provides the use of the nucleic acid molecule encoding a porcine epidemic diarrhea virus (PEDV) spike (S) protein, the PEDV (S) protein or the immunogenic composition as described herein for treating and/or preventing clinical signs caused by PEDV infection in a subject or for reducing diarrhea in a subject.

Sequence Overview

The following sequences are detailed and disclosed hereby in the present invention:
SEQ ID NO:1: RSXIEDXX,
SEQ ID NO:2: wild type G2a PEDV S amino acid sequence US,
SEQ ID NO:3: wild type G2b PEDV S amino acid sequence EU,
SEQ ID NO:4: RSXIEDLLF,
SEQ ID NO:5: RSXIEDAAF,
SEQ ID NO:6: XXXFXKXXXX,
SEQ ID NO:7: YXXFXKXH,
SEQ ID NO:8: AXXFXKXR,
SEQ ID NO:9: PEDV S European strain genotype 2b (G2b) sequence with mutation 897A,
SEQ ID NO:10: PEDV S European strain genotype 2b (G2b) sequence with mutation at amino acid position 898 to A,
SEQ ID NO:11: PEDV S European strain genotype 2b (G2b) sequence with mutation 897A and 898A,
SEQ ID NO:12: PEDV S European strain genotype 2b (G2b) sequence with mutation 897A and 1374A and 1381R,
SEQ ID NO:13: PEDV S European strain genotype 2b (G2b) sequence with mutation 898A and 1374A and 1381R,
SEQ ID NO:14: PEDV S European strain genotype 2b (G2b) sequence with mutation 897A, 898A and 1374A and 1381R,
SEQ ID NO:15: PEDV S US strain genotype 2a (G2a) sequence with mutation 900A,
SEQ ID NO:16: PEDV S US strain genotype 2a (G2a) sequence with mutation at amino acid position 901 to A,
SEQ ID NO:17: PEDV S US strain genotype 2a (G2a) sequence with mutation 900A and 901A,
SEQ ID NO:18: PEDV S US strain genotype 2a (G2a) sequence with mutation 900A and 1377A and 1384R,
SEQ ID NO:19: PEDV S US strain genotype 2a (G2a) sequence with mutation 901A and 1377A and 1384R,
SEQ ID NO:20: PEDV S US strain genotype 2a (G2a) sequence with mutation 900A, 901A and 1377A and 1384R,
SEQ ID NO:21: RSXIEDLX,
SEQ ID NO:22: RSXIEDXL,
SEQ ID NO:23: RSXIEDLA,
SEQ ID NO:24: RSXIEDAL,
SEQ ID NO:25: RSXIEDAA,
SEQ ID NO:26: XXXFXKXHXX,
SEQ ID NO:27: YXXFXKXXXX,
SEQ ID NO:28: AXXFXKXHXX,
SEQ ID NO:29: YXXFXKXRXX,
SEQ ID NO:30: AXXFXKXRXX,
SEQ ID NO:31: RSXIEDLG,
SEQ ID NO:32: RSXIEDGL,
SEQ ID NO:33: RSXIEDGG,
SEQ ID NO:34: RSXIEDGA,
SEQ ID NO:35: RSXIEDAG,
SEQ ID NO:36 comprises a cloning cassette of PEDV spike protein—including duplication of the UTR regions for the inserted gene,
SEQ ID NO:37 (RNA) corresponds to a sequence encoding the S protein of SEQ ID NO:14,
SEQ ID NO:38 (RNA) corresponds to a sequence comprising SEQ ID NO:37,
SEQ ID NO:39: wild type G2a PEDV S amino acid sequence CN,
SEQ ID NO:40: PEDV S CN strain genotype 2a (G2a) sequence with mutation 900A, 901A and 1377A and 1384R,
SEQ ID NOs:41-44: probe, primer, and ultramer sequences (Table 2).

As in the sequence listing amino acid sequences are presented in the three-letter code format using the symbol "Xaa" as equivalent for the variable "X", it is in particular understood that the wording "X at residue" provided in the sequence listing is equivalent to "Xaa at residue".

CLAUSES

The following Clauses are described herein:
The invention provides the following clauses:

1. A nucleic acid molecule encoding a porcine epidemic diarrhea virus (PEDV) spike (S) protein comprising the amino acid sequence $$RSX_1IEDX_2X_3, \quad \text{(SEQ ID NO: 1)}$$

wherein
(I) $X_2$ is an amino acid residue other than a leucine residue and $X_3$ is a leucine residue, or
(II) $X_2$ is a leucine residue and $X_3$ is an amino acid residue other than a leucine residue, or
(III) $X_2$ is an amino acid residue other than a leucine residue and $X_3$ is an amino acid residue other than a leucine residue.

2. The nucleic acid molecule of clause 1 comprising the amino acid sequence
$RSX_1IEDX_2X_3$ (SEQ ID NO:1), wherein
R is the arginine residue at amino acid position 894 if the PEDV S protein is a genotype 2a (G2a) PEDV S protein and wherein the numbering of the amino acid position refers to the amino acid sequence of wild type G2a PEDV S protein, or
R is the arginine residue at amino acid position 891 if the PEDV protein is a genotype 2b (G2b) PEDV S protein and wherein the numbering of the amino acid position refers to the amino acid sequence of wild type G2b PEDV S protein.

3. The nucleic acid molecule of clause 2, wherein
the amino acid sequence of wild type G2a PEDV S protein is the amino acid sequence of wild type G2a PEDV S protein of SEQ ID NO:2 or SEQ ID NO:39, and/or
the amino acid sequence of wild type G2b PEDV S protein is the amino acid sequence of wild type G2b PEDV S protein of SEQ ID NO:3.

4. A nucleic acid molecule encoding a porcine epidemic diarrhea virus (PEDV) spike (S) protein comprising the amino acid sequence $$RSX_1IEDX_2X_3, \quad \text{(SEQ ID NO: 1)}$$

wherein R is the conserved arginine residue of the S1/S2 cleavage site of said PEDV S protein, $X_1$ can be any amino acid residue and wherein
(I) $X_2$ is an amino acid residue other than a leucine residue and $X_3$ is a leucine residue, or
(II) $X_2$ is a leucine residue and $X_3$ is an amino acid residue other than a leucine residue, or
(III) $X_2$ is an amino acid residue other than a leucine residue and $X_3$ is an amino acid residue other than a leucine residue.

5. A nucleic acid molecule encoding a porcine epidemic diarrhea virus (PEDV) spike (S) protein selected from the group consisting of the following (a) and (b):
(a) a genotype 2a (G2a) PEDV S protein having at least one mutation, wherein
the leucine residue at amino acid position 900 is substituted by an amino acid residue other than a leucine residue, and/or
the leucine residue at amino acid position 901 is substituted by an amino acid residue other than a leucine residue,
wherein the numbering of the amino acid positions refers to the amino acid sequence of wild type G2a PEDV S protein of SEQ ID NO:2 or SEQ ID NO:39,
(b) a genotype 2b (G2b) PEDV S having at least one mutation, wherein
the leucine residue at amino acid position 897 is substituted by an amino acid residue other than a leucine residue, and/or
the leucine residue at amino acid position 898 is substituted by an amino acid residue other than a leucine residue,
wherein the numbering of the amino acid positions refers to the amino acid sequence of wild type G2b PEDV S protein of SEQ ID NO:3.

6. The nucleic acid molecule of any one of clauses 1 to 5, wherein said amino acid residue other than a leucine residue is selected from the group consisting of alanine residue, glycine residue, isoleucine residue, methionine residue and valine residue.

The nucleic acid molecule of any one of clauses 1 to 6, wherein said amino acid residue other than a leucine residue is an alanine residue.

8. The nucleic acid molecule of any one of clauses 5 to 7, wherein the numbering of the amino acid positions refer to the amino acid sequence RSXIEDLLF (SEQ ID NO:4) of wild type G PEDV S protein, wherein R is the conserved arginine residue of the S1/S2 cleavage site of said PEDV S protein and LL are the amino acid positions 900 and 901 within the genotype 2a (G2a) PEDV S protein or LL are the amino acid positions 897 and 898 within the genotype 2b (G2b) PEDV S protein.

9. The nucleic acid molecule of any one of clauses 5 to 8, wherein the numbering of the amino acid positions refer to the amino acid sequence RSXIEDLLF (SEQ ID NO:4) of wild type G PEDV S protein, wherein R is the arginine residue at amino acid position 894 and LL are the amino acid positions 900 and 901 within the genotype 2a (G2a) PEDV S protein, or R is the arginine residue at amino acid position 891 and LL are the amino acid positions 897 and 898 within the genotype 2b (G2b) PEDV S protein.

10. The nucleic acid molecule of any one of clauses 1 to 9, wherein said PEDV S protein comprises the amino acid sequence RSXIEDAAF (SEQ ID NO:5), wherein R is the conserved arginine residue of the S1/S2 cleavage site of said PEDV S protein and AA are the amino acid positions 900 and 901 within the genotype 2a (G2a) PEDV S protein or AA are the amino acid positions 897 and 898 within the genotype 2b (G2b) PEDV S protein.

11. The nucleic acid molecule of any one of clauses 1 to 10, wherein said PEDV S protein comprises the amino acid sequence RSXIEDAAF (SEQ ID NO:5), wherein R is the arginine residue at amino acid position 894 and AA are the amino acid positions 900 and 901 within the genotype 2a (G2a) PEDV S protein, or R is the arginine residue at amino acid position 891 and AA are the amino acid positions 897 and 898 within the genotype 2b (G2b) PEDV S protein.

12. The nucleic acid molecule of any one of clauses 1 to 11, wherein said PEDV S protein further comprises the amino acid sequence $$X_1X_2X_3FX_4KX_5X_6X_7X_8, \quad \text{(SEQ ID NO: 6)}$$

wherein $X_8$ is the C-terminal amino acid residue of said PEDV S protein or the amino acid residue at the −2 position relative to the C-terminal amino acid position of said PEDV S protein, $X_2$ to $X_5$, $X_7$ and $X_8$ can be any amino acid residue, and wherein (i) $X_1$ is an amino acid residue other than a tyrosine residue and $X_6$ is a histidine residue, or (ii) $X_1$ is a tyrosine residue and $X_6$ is an amino acid residue other than a histidine residue, or (iii) $X_1$ is an amino acid residue other than a tyrosine residue and $X_6$ is an amino acid residue other than a histidine residue.

13. The nucleic acid molecule of any one of clauses 5 to 13, wherein (a) in said G2a PEDV S protein further the tyrosine residue at amino acid position 1377 is substituted by an amino acid residue other than a tyrosine residue, and/or the histidine residue at amino acid position 1384 is substituted by an amino acid residue other than a histidine residue, or (b) in said G2b PEDV S protein further the tyrosine residue at amino acid position 1374 is substituted by an amino acid residue other than a tyrosine residue, and/or the histidine residue at amino acid position 1381 is substituted by an amino acid residue other than a histidine residue.

14. The nucleic acid molecule of clause 12 to 13, wherein said amino acid residue other than a tyrosine residue is selected from the group consisting of alanine residue, glycine residue, leucine residue, isoleucine residue, methionine residue and valine residue, and/or said amino acid residue other than a histidine residue is an arginine residue. 15. The nucleic acid molecule of any one of clauses 12 to 14, wherein said amino acid residue other than a tyrosine residue is an alanine residue, and/or said amino acid residue other than a histidine residue is an arginine residue.

16. The nucleic acid molecule of any one of clauses 13 to 15, wherein the numbering of the amino acid positions refers to the amino acid sequence YXXFXKXH (SEQ ID NO:7) of wild type G PEDV S protein, wherein Y and H are the amino acid positions 1377 and 1384 within the genotype 2a (G2a) PEDV S protein or Y and H are the amino acid positions 1374 and 1381 within the genotype 2b (G2b) PEDV S protein.

17. The nucleic acid molecule of any one of clauses 12 to 16, wherein the nucleic acid molecule comprises a sequence encoding the amino acid sequence AXXFXKXR (SEQ ID NO:8), wherein A and R are the amino acid positions 1377 and 1384 within the genotype 2a (G2a) PEDV S protein or A and R are the amino acid positions 1374 and 1381 within the genotype 2b (G2b) PEDV S protein.

18. The nucleic acid molecule of any one of clauses 1 to 17, wherein said PEDV S protein:

i) (a) comprises or consists of an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence of any one of SEQ ID NOS: 15, 16, 17, 18, 19, 20, 40, or (b) comprises or consists of an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence of any one of SEQ ID NOS: 9, 10, 11, 12, 13, 14; and/or ii) (a) is encoded by a nucleotide sequence encoding an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence any one of SEQ ID NOS: 15, 16, 17, 18, 19, 20, 40, or (b) is encoded by a nucleotide sequence encoding an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence of any one of SEQ ID NOS: 9, 10, 11, 12, 13, 14.

19. The nucleic acid molecule of any one of clauses 1 to 18, wherein said PEDV S protein (a) comprises the amino acid sequence of any one of SEQ ID NOS: 15, 16, 17, 18, 19, 20, 40, or (b) comprises the amino acid sequence of any one of SEQ ID NOS: 9, 10, 11, 12, 13, 14.

20. A PEDV (S) protein encoded by the nucleic acid molecule of any one of clauses 1 to 19.

21. The nucleic acid molecule of any one of clauses 1 to 19 or the PEDV S protein of clause 20, wherein said nucleic acid molecule encoding the PEDV S protein or the PEDV S protein is recombinant.

22. A polynucleotide comprising the nucleic acid molecule of any one of clauses 1 to 19.

23. A vector comprising the nucleic acid molecule of any one of clauses 1 to 19 or the polynucleotide of clause 22.

24. The vector of clause 23, wherein the vector is a CDV, EHV, ORF virus, PRV, CAV, PCMV or BoHV-4.

25. The vector of clause 23, wherein the vector is a CDV or EHV.

26. An immunogenic composition comprising the nucleic acid molecule encoding the PEDV S protein of any one of clauses 1 to 19 and/or the PEDV S protein of clause 20 and/or the vector of any one of clauses 23 to 25.

27. The immunogenic composition of clause 26, wherein the immunogenic composition further comprises a pharmaceutically acceptable carrier.

28. The immunogenic composition of clause 26 or 27, wherein the immunogenic composition is a vaccine.

29. A cell comprising the nucleic acid molecule of any one of clauses 1 to 19, the polynucleotide of clause 22 or the vector of any one of clauses 23 to 25.

30. A method of producing the nucleic acid molecule encoding the PEDV S protein of any one of clauses 1 to 19 and/or the PEDV S protein of clause 20, comprising transfecting a cell with the vector of any one of clauses 23 to 25.

31. A method of preparing an immunogenic composition for the treatment and/or prophylaxis of PEDV infections in a subject comprising:

a.) infecting a cell with the vector of any one of clauses 23 to 25;

b.) obtaining said vector; and c.) addition of a pharmaceutically acceptable carrier.

32. The cell of clause 29 or the method of clause 30 or 31, wherein the cell is a Vero cell, ST cell, BHK-21 cell, Ma104 cell, MDBK cell, RK13 cell, MDCK cell or PK15 cell.

33. The immunogenic composition of clause 27 or the method of clause 31, wherein said pharmaceutically acceptable carrier is selected from the group consisting of solvents, dispersion media, coatings, stabilizing agents, diluents, preservatives, antibacterial and antifungal agents, isotonic agents, adsorption delaying agents, adjuvants, immune stimulants, and combinations thereof.

34. A method of immunizing a subject comprising administering to the subject an immunogenic composition of any one of clauses 26 to 28.

35. The immunogenic composition of any one of clauses 26 to 28 for use in a method of immunizing a subject, the method comprising administering to the subject a therapeutically effective amount of said immunogenic composition.

36. A method of treating and/or preventing clinical signs caused by PEDV infection in a subject of need, the method comprising administering to the subject a therapeutically effective amount of an immunogenic composition according to any one of clauses 26 to 28.

37. The immunogenic composition of any one of clauses 26 to 28 for use in a method of treating and/or preventing clinical signs caused by PEDV infection in a subject of need, the method comprising administering to the subject a therapeutically effective amount of said immunogenic composition.

38. A method of reducing the mortality in a subject in comparison to a subject of a non-immunized control group of the same species, the method comprising administering to the subject a therapeutically effective amount of an immunogenic composition according to any one of clauses 26 to 28.

39. The immunogenic composition of any one of clauses 26 to 28 for use in a method of reducing the mortality in a subject in comparison to a subject of a non-immunized control group of the same species, the method comprising administering to the subject a therapeutically effective amount of said immunogenic composition.

40. A method for inducing the production of antibodies specific for PEDV in a sow, wherein said method comprising administering the immunogenic composition of any one of clauses 26 to 28 to said sow.

41. The immunogenic composition of any one of clauses 26 to 28 for use in a method for inducing the production of antibodies specific for PEDV in a sow, the method comprising administering to said sow a therapeutically effective amount of said immunogenic composition.

42. A method of reducing the mortality in a piglet in comparison to a piglet of a non-immunized control group, the method comprising administering to the sow of the piglet a therapeutically effective amount of an immunogenic composition according to any one of clauses 26 to 28, wherein the piglet is to be suckled by said sow.

43. The immunogenic composition of any one of clauses 26 to 28 for use in a method of reducing the mortality in a piglet in comparison to a piglet of a non-immunized control group, the method comprising administering to the sow of the piglet a therapeutically effective amount of said immunogenic composition, wherein the piglet is to be suckled by said sow.

44. A method of reducing or preventing the clinical signs or disease caused by an infection with a PEDV in a piglet, wherein the piglet is to be suckled by a sow to which the immunogenic composition of any one of clauses 26 to 28 has been administered.

45. The immunogenic composition of any one of clauses 26 to 28 for use in a method of reducing or preventing the clinical signs or disease caused by an infection with a PEDV in a piglet, wherein the piglet is to be suckled by a sow to which the said immunogenic composition has been administered.

46. A method of reducing or preventing the clinical signs or disease caused by an infection with a PEDV in a piglet, wherein said method comprises
administering the immunogenic composition of any one of clauses 26 to 28 to a sow, and
allowing said piglet to be suckled by said sow.

47. The immunogenic composition of any one of clauses 26 to 28 for use in a method of reducing or preventing the clinical signs or disease caused by an infection with a PEDV in a piglet, wherein said method comprises
administering said immunogenic composition to a sow, and
allowing said piglet to be suckled by said sow.

48. The method of any one of clauses 34 to 47, wherein said sow to which the immunogenic composition is administered is a sow being pregnant, in particular with said piglet.

49. The method of any one of clauses 34, and 46 to 48, comprising the steps of
administering the immunogenic composition of any one of clauses 26 to 28 to a sow being pregnant with said piglet,
allowing said sow to give birth to said piglet, and
allowing said piglet to be suckled by said sow.

50. The method of any one of clauses 36, 37, 40, 44, 45, 46, 47, 48 or 49, wherein said method results in an improvement in a clinical sign or efficacy parameter selected from the group consisting of: a reduction in weight loss, a lower virus load, a reduction of diarrhea, a reduced shedding, a reduced rectal temperature, reduced mortality, reduced gross pathological lesions in the intestine, or combinations thereof, in comparison to a subject of a non-immunized control group of the same species.

51. The method of any one of clauses 34 to 39, wherein said subject is a piglet, pig or sow.

52. The method of any one of clauses 34 to 39 or 51, wherein the immunogenic composition is administered to the subject within the first month of age.

53. The method of any one of clauses 34 to 52, wherein said immunogenic composition is administered to sows during pregnancy and lactation.

54. The method of any one of clauses 34 to 53, wherein the immunogenic composition is administered at two or more doses.

55. The method of any one of clauses 34 to 44, wherein said immunogenic composition is administered to sows two times, the first administration between 9 and 5 weeks before farrowing and the second administration between 6 and 1 week before farrowing.

56. The method of any one of clauses 34 to 55, wherein said immunogenic composition is administered intranasally, mucosally, orally, intradermally or intramuscularly.

57. The method of any one of clauses 34 to 56, wherein said immunogenic composition is administered intranasally or orally.

58. The method of any one of clauses 34 to 57, wherein the immunogenic composition comprises between $1 \times 10^3$ to $1 \times 10^7$ $TCID_{50}$/ml, in particular of a vector according to any one of clauses 23 to 25.

59. The method of any one of clauses of 34 to 58, wherein the method results in a reduction of the shedding from day 5, 7 or 10 after challenge or infection.

60. The method of any one of clauses 34 to 59, wherein the method increases the protection against a homologous challenge.

DETAILED DESCRIPTION OF THE PREFERRED EMBODIMENTS

The following examples set forth preferred materials and procedures in accordance with the present invention. Although any methods and materials similar or equivalent to those described herein can be used in the practice or testing of the present invention, the preferred methods, devices, and materials are now described. It is to be understood, however, that these examples are provided by way of illustration only, and nothing therein should be deemed a limitation upon the overall scope of the invention.

Example 1

Preparation of the Spike Modifications

A) PEDV-S Expression by Recombinant CDV Vectors

In an in vitro experiment, a full plasmid (pBR322) encoding fully CDV genome derived from Lederle vaccine strain (Lederle; ATCC VR-128) was digested using SacII endonuclease followed by cloning PEDV spike (S) protein encoding cassette between the P gene and the M gene (resulting in a sequence comprising SEQ ID NO:36). Upon cloning and rescue of recombinant CDV-PEDV-S, it was possible to show expression of Porcine Epidemic Diarrhea Virus spike protein of a 2b genotype in CDV associated fluorescent focuses. Respective results are also achieved for a corresponding CDV vector (i.e. only differing in the sequence encoding the Porcine Epidemic Diarrhea Virus spike protein of a 2a genotype SEQ ID NO:20). Results obtained for both vectors by immunofluorescence indicate strong expression of spike protein of PEDV in all CDV infected syncytia (data not shown).

B) Preparation of EHV Expressing PEDV Spike

For generating EHV1 recombinants expressing spike proteins PEDV-52b-wt and PEDV-S2b-mut synthetic sequence SEQ ID NO:3 and SEQ ID NO:14 was used. Its sequence was synthesized and subcloned in the transfer vector pUC19-ORF1/3-PEDV-52b-wt and pUC19-ORF1/3-PEDV-S2b-mut respectively.

By en-passant mutagenesis using the RED recombination system (Tischer et al. 2006) the expression cassette of PEDV-S2b-wt or PEDV-S2b-mut was inserted in orf1/3 region of pRacH-SE to produce final BAC DNA pRacH-SE-PEDV-S2b-wt and pRacH-SE- PEDV-S2b-mut.

RK13 cells were transfected with generated BAC DNA, recombinant viruses rEHV-1 were rescued and plaque-purified. Correct insertion of the expression cassette was verified by sequencing of a high-fidelity PCR product of the insertion region. Expression of the transgene in infected cells was analyzed and confirmed by indirect immunofluorescence assay (IFA) (data not shown). Furthermore, the virus was passaged for 20 cell passages in RK-13 cells to confirm in vitro stability of the constructs.

Example 2

Localization of Spike in Plasma Membrane

EHV-1 recombinant vector encoding wild type (naturally occurring) PEDV-S protein of 2b genotype (EHV1-PEDV-S2b-wt) was compared with EHV-1 recombinant vector encoding mutated spike protein (on amino acid positions 897/898/1374/1381 (SEQ ID NO:14)—designated as EHV1-PEDV-S2b-mut).

Briefly, RK13 cells were plated in the 6-wells cell culture plates at the density of $2\times10^5$ of the cells to one well of the six well plate. On the next day (24 h post seeding), the cells were infected with either EHV1-PEDV-S2b-wt or EHV1-PEDV-S2b-mut at MOI of 0.01. Two days post infection (48 hours) the cells were fixed using 3% paraformaldehyde solution for one hour. Fixed cell monolayers, were than permabilized using 0.1% Tween20 and then stained for 1 hour using mouse anti-PEDV monoclonal antibodies clone 7D7_G1 (Abpro-Labs 2.4.16) using 1:200 dilution in PBS. After one hour the cells were washed twice with room temperature PBS (1000 μl per well). Add 750 μl of 1:500 dilution of commercial secondary antibody (Goat anti Mouse-FITC (Life Technology cat:A11029 lot:1705900) per well and incubated for 60 minutes in the dark (protected from light). After the incubation, secondary antibody solution was aspirated by vacuum, followed by twice Wash with room temperature PBS (1000 μl per well). The results were obtained using Olimpus inverted fluorescent microscope (mod.IX81), using FITC filter to detect specific fluorescence of PEDV spike protein in the cells (FIG. 1). The spike protein expressed from EHV1-PEDV-S2b-wt recombinant vector is primarily localized in the cytoplasm, while spike protein expressed from EHV1-PEDV-S2b-mut is localized primarily within the cellular membrane.

Example 3

Growth Kinetics in Vero Cells

Introduction: Efficient growth of recombinant viral vector is one of the essential features regarding the efficient production of the vaccine. Canine distemper virus (CDV) vaccines are produced on Vero cells (ATCC® CCL-81™) and very often using a roller bottle production system. We compared the growth kinetics of two CDV recombinants, that were: _(i) a CDV backbone derived from Lederle vaccine strain (c.f. Example 1) with an insert of the sequence of SEQ ID NO:39 (encoding the PEDV Spike protein of SEQ ID NO:20) between the P gene and the M gene, named "CDV-PEDV-spike-MUT" or "CDV-PEDV-spike mut" herein, and (ii) a respective vector encoding the corresponding wild type protein (the PEDV Spike protein of SEQ ID NO:2), named "CDV-PEDV-spike-WT" or "CDV-PEDV-spike wt" herein.

Experimental setup: Roller bottles (490 cm$^3$) were seeded with $2\times10^7$ of Vero cells. On the next day, CDV-PEDV-spike-MUT or CDV-PEDV-spike-WT virus stocks were used to infect the Vero cells in roller bottles at the MOI of 0.01. In the following 7 days, 1 ml aliquots we sampled from each roller bottle in triplicates. All samples were stored in −80° C. freezers until analysis. On the day of analysis, the samples were thawed on ice and virus titration was performed following the protocol:

CDV Titration Protocol

Material

Cells: VeroDogSLAM BI seeded 24 hrs before in 96 well plates, $6\times10^3$ cells/well Media: MEM (SAFC, SLBX3503)

48 well plate for dilution

Procedure

Use 48 well plate for dilution
Fill wells with 1080µl of MEM
Pipet 120 µl of each sample in the first row
Mix program, make a 10-fold dilution from 10^A-1 to 10^-8 of each sample.
For each dilution one 96well plate of cells is used.
Transfer the dilution on the pre-seeded cells (100 µl/well)
Make 8× replicates of for each sample
Incubation for 3 days at 37° C. cell incubators
Readout using microscopy by detecting the typical CDV syncytia formation on cells Results and discussion: CDV-PEDV-spike-MUT recombinant showed higher infectious virus titers on day 1, 2, 3, 4, 5 and 6 after infection of Vero cells. Furthermore, both recombinants reached peak supernatant titers on day 4 post infection, but CDV-PEDV-spike-MUT reached 2-fold higher infection titers than CDV-PEDV-spike-WT recombinant (see FIG. 2), indicating the benefits of the mutation of the spike to the fitness of the CDV vector.

All those virus titers were measured in cell free supernatants. Based on empirical data (data not shown) it is expected that the titers in the cell fractions are at least 100 times higher, and that thus in a production setup (as the roller bottles would be harvested including the cell fraction in the production setup) the titer differences between the two recombinants are proportionally even higher.

Example 4

Vaccine Animal Data

Vaccine Efficacy Study

Porcine epidemic diarrhea (PED) is a highly contagious swine disease that can have tremendous economic impact. While all age classes of pigs are susceptible to infection, severe clinical signs and mortality are mainly seen in suckling piglets. The causative agent is PED virus (PEDV), an enveloped, single positive-stranded RNA-virus of the genus *Alphacoronavirus* within the Coronaviridae virus family. In Europe, PEDV first occurred in the late 1970ies in England. Afterwards it spread through whole Europe causing sporadic outbreaks. In the late 1990ies, PEDV had disappeared from the European pig farms as evidenced by very low seroprevalence and non-existent disease reporting. Outbreaks and endemic infections were still reported from Asia where the disease has high impact on the productivity of industrialized pig farms. Starting from 2005, PED cases were again reported from Europe, i.e. Italy. After the introduction of an apparently highly virulent PEDV into the United States in 2013, cases were also reported from Central Europe, including Germany and neighboring countries. The latter cases were caused by related but distinct PEDV strains (so-called S-INDEL strains). In Germany, cases were reported starting from May 2014 with high morbidity and variable lethality in suckling pigs.

This study, in which a CDV backbone derived from Lederle vaccine strain (c.f. Example 1) with an insert of the sequence of SEQ ID NO:37 (encoding a PEDV Spike protein) between the P gene and the M gene (the vector thus comprising the sequence of SEQ ID NO:38) was tested as vector vaccine (named hereinafter "CDV_PEDV-Spike vaccine" or "CDV PEDV-Spike vector vaccine", respectively), included six sows and their offspring.

All animals were checked for PEDV by RT-qPCR targeting the S-gene, and PEDV-specific antibodies. Only negative animals were enrolled in the study.

Three treatment groups (see below) received randomly assigned animals:

Group 1 (negative control): Two sows (designated #1 and #2), unvaccinated;

Group 2 (positive control): Two sows (designated #3 and #4), unvaccinated;

Group 3 (CDV_PEDV-Spike): Two sows (designated #5 and #6), vaccinated with CDV PEDV-Spike vector vaccine.

The vaccination of the two sows of group 3 was done according to the following scheme, wherein the stock titer of the CDV_PEDV-Spike vaccine, defined by endpoint titration, was $7.94 \times 10^4$ TCID$_{50}$/ml:

9 weeks prior to expected farrowing date: each of the two sows received 4 ml of the vaccine intranasally (2 ml in each nostril);

6 weeks prior to expected farrowing date: each of the two sows received 4 ml of the vaccine intranasally (2 ml in each nostril);

3 weeks prior to expected farrowing date: each of the two sows received 4 ml of the respective vaccine intranasally (2 ml in each nostril) and additionally 2 ml intramuscularly.

Piglets born to sows of group 1 (13 piglets of sow #1 and 12 piglets of sow #2) were orally mock-inoculated. Piglets born to sows of group 2 (12 piglets of sow #3 and 14 piglets of sow #4), and group 3 (5 piglets of sow #5 and 15 piglets of sow #6) were orally challenged with a PEDV field strain (named "PEDV EU" hereinafter) at an age of 4 days of life.

For inoculation of piglets of groups 2 and 3, cell culture adapted PEDV EU was used. The titer was $2.15 \times 10^5$ TCID$_{50}$/ml. Piglets of groups 2 and 3 were orally inoculated. In this case, each piglet received 1 ml of a 1:10 diluted viral stock (titer $2.15 \times 10^4$ TCID$_{50}$) using 2 ml syringes.

Piglets of group 1 were orally mock-inoculated using 1 ml cell culture medium in 2 ml syringes.

During the whole trial, rectal swabs (COPAN plain swabs without medium) were taken at the day of inoculation and on day 1 to 10 post inoculation (pi) as well as day 14, 17 and 20/21 pi of all animals for RT-qPCR analyses. Additional rectal swabs were taken from 4 piglets of each sow prior to inoculation and two days post challenge for bacteriological examination. Moreover, clinical signs indicative for PED were recorded daily using the established standardized cumulative score system (see below). Blood samples were taken at the day of inoculation and day 14 and 20/21 pi (end of trial) or the day of euthanasia or death of the respective animal.

Clinical Monitoring

The established cumulative clinical score was used for daily monitoring for clinical signs indicative for PED (see table below).

TABLE 1

Cumulative clinical score for clinical signs indicative for PED

| Score | General behaviour | Feed intake/suckling | Gastrointestinal symptoms |
|---|---|---|---|
| 0 | Agile, attentive, no abnormalities | Greedy suckling, good filled stomach, intake of piglet feed | Physiological feces |
| 1 | Slight depression | Slow suckling, hardly interested in piglet feed | Pasty feces, vomiting |
| 2 | Depression, isolaton from group, vocalisation (moaning) | Reluctant feed intake, hardly interested in suckling/piglet feed, sunken flanks | Watery feces, reddened anal region, vomiting |
| 3 | Lateral position, signs of severe dehydration, low body temperature | Total anorexia, decreasing of milk production of sow | Watery feces with blood or fibrin added, highly reddened anal region, vomiting |

Sample Preparation and Nucleic Acid Extraction

Rectal swabs were submerged in 1 ml Dulbecco's Modified Eagle Medium and incubated for 1 hour at room temperature. Viral RNA was extracted using either the QIAmp ViralRNA Mini Kit (Qiagen) or the NucleoMagVet-Kit in combination with the KingFisher extraction platform. The RNA was stored at −20° degree until further use.

Blood samples were centrifuged at 2031×g for 20 min at room temperature to obtain serum. The resulting serum was aliquoted and stored at −20° C.

Virus Detection

To detect PEDV shedding, RT-qPCR-systems targeting the S-gene of PEDV were used as previously described (Stadler et al., BMC Vet Res. 11:142 (2015)). Samples taken at days 0 to 7 dpi (days post challenge virus inoculation) and at 10 and 20/21 dpi were tested for PEDV-genome. The amount of genome copies/µl was calculated using an in-house standard.

Antibody Detection

A commercial indirect ELISA (INgezim PEDV, INGE-NASA, Madrid, Spain) was performed with all sera according to the producer's manual.

Bacteriology

Fecal swabs of four piglets per litter were taken at 0 and 2 dpi for differential bacteriology.

Statistics

Shapiro-Wilk test was used for normality testing and a Mann-Whitney rank sum test was conducted as implemented in the software package. Statistical significance was tested using SigmaPlot software.

Results

Antibody Detection in Serum

All piglets of the CDV group showed positive results in the ELISA (detecting antibodies against PEDV Spike protein) prior to challenge inoculation due to antibody positive colostrum intake, while all animals of the positive and negative control group showed clearly negative results.

At 14 dpi all but three piglets in the positive control group seroconverted, while all animals in the vaccine group showed still high amounts of PEDV specific IgG in serum samples.

At the end of the study all piglets of the CDV group and of the positive control group showed strongly positive results in the ELISA. None of the animals in the negative control seroconverted during the whole trial.

In a further study it was also seen that respective antibody results were likewise achieved when the mother sows were only vaccinated twice via the intranasal route.

Bacteriology

Fecal swabs taken at 0 and 2 dpi did not show any pathogenic bacteria. The bacterial flora did not undergo significant changes upon infection.

Clinical Signs

Piglets of the positive control group (group 2) clearly showed clinical signs indicative for PEDV over 7 days starting with vomiting 24 hpi followed by diarrhea. 8 of 26 of the piglets had to be euthanized due to severe dehydration and clinical score values over 6 (humane endpoint). First clinical signs indicative for PEDV were detectable at 36 hpi.

In total, the clinical signs of the CDV vector vaccinated and PEDV challenged piglets (group 3) were better regarding the general behavior and only 2 of 20 (10%) of the pigs of group 3 had to be euthanized due to severe dehydration and clinical score values over 6 (as compared to 31% of the piglets of group 2).

Animals in the negative control stayed healthy during the whole trial.

Shedding of Virus

A clear difference in virus shedding could be detected between the challenged groups. At 1 dpi all challenged piglets were positive for virus genome in rectal swabs, but animals in the CDV-PEDV vaccinated group showed significantly lower PEDV genome copy numbers (mean CT value 32.79), then in challenge group (mean CT value 26.65).

Also, while for the next five days pi, the genome load in rectal swabs of the CDV group was quite similar to the positive control, beginning at 7 dpi the detectable amount of virus genome declined below the cutoff level in piglets protected by the vaccinated sows, while all animals in the positive control group still shed PEDV.

No PEDV genome could be detected in swabs of the negative control group.

In conclusion, the outcome of the study was that piglets born to sows vaccinated with the CDV PEDV-Spike recombinant vaccine showed a reduction of clinical signs, as compared to the positive control, and in particular, a great improvement was seen with regard to the mortality/letality of the piglets. Furthermore, virus shedding after the PEDV challenge was significantly reduced.

Besides, an animal study corresponding to the above described vaccine efficacy study is performed, wherein a CDV backbone derived from Lederle vaccine strain (c.f. Example 1) with an insert encoding the PEDV Spike protein of SEQ ID NO:40 between the P gene and the M gene is administered twice (5 weeks prior to farrowing and 2 weeks prior to farrowing), and wherein a highly virulent genotype 2a PEDV field strain is used for the challenge. Piglets born to sows vaccinated with this recombinant vaccine show reduced mortality or a reduction of clinical signs, as compared to the challenge control.

EXAMPLE 5

This animal study, in which a CDV backbone derived from Lederle vaccine strain (c.f. Examples 1 and 4) with an insert encoding the PEDV Spike protein of SEQ ID NO:20 between the P gene and the M gene was tested as vector vaccine (named hereinafter "CDV PEDV-G2a vaccine" or "CDV PEDV-G2a Spike vector vaccine", respectively), included twenty (20) sows and their offspring.

Only animals which were considered negative for PEDV by qRT-PCR and ELISA were enrolled in the study.

Three treatment groups (see below) received randomly assigned animals:

Group 1 (Strict negative control): Four sows (designated 1-4), unvaccinated;

Group 2 (Challenge control): Eight sows (designated 5-12), unvaccinated;

Group 3 (CDV_PEDV-G2a-Spike): Eight sows (designated 13-20), vaccinated with CDV PEDV-G2a-Spike vector vaccine.

The vaccination of the 8 sows of group 3 was done at 5 weeks pre-farrow (DO) and 2 weeks pre-farrow (D21) of the study, wherein the stock titer of the CDV PEDV-G2a Spike vaccine, defined by endpoint titration, was $2.57\times10^5$ TCID50/ml. At each vaccination, the sows received 4 mL of the vaccine intranasally (2 mL in each nostril).

Piglets born to sows of group 1 (41 piglets in total) were not challenged (strict controls). Piglets born to sows of group 2 (81 piglets in total), and group 3 (83 piglets in total) were orally challenged with a highly virulent PEDV field strain belonging to G2a genotype with the dose $2.0\times10^3$ $TCID_{50}$/2 mL dose (1 mL intranasal+1 mL oral) at an age of 3-7 days of life.

During the whole trial, rectal swabs were taken at the day prior to inoculation and on day 1, 3, 7 and 14 pi (post challenge virus inoculation).

Sample Preparation and Nucleic Acid Extraction

Rectal swabs were submerged in 2 ml Minimum Essential Medium (MEM) upon collection and stored at −70° C. prior to processing. Sample were processed by vortexing for 10 seconds followed by centrifugation for 10 minutes at 1,500×g at 4° C. Following processing, 100 µl/sample was used for viral RNA extraction using the BS96 Vet 100 BioSprint extraction platform with the BioSprint One-For-All Vet Kit (Qiagen) The RNA was stored at −20° degree until further use.

Blood samples were centrifuged at 1960×g for 10 min at room temperature to obtain serum. The resulting serum was aliquoted and stored at −70° C.

Virus Detection

To detect PEDV shedding, an internally derived RT-qPCR-system targeting the S-gene of PEDV was used: The quantitative one-step RT-PCR kit (iTaq Universal One-Step RT-PCR kit; BioRad, cat no. 1725140) was used for the assay. Real-time RT-PCR was carried out in a 25 µl reaction containing 2 µl of extracted total nucleic acid, 0.75 µl of probe (4 µM), 0.5 µl of each primer (10 µM), 12.5 µl of 2X RT-PCR mix, 0.5 µl iScript reverse transcriptase and 8.25 µl of DEPC-treated water. See Table 2 below for primer, probe and ultramer sequences. The reaction took place using a CFX96 real-time PCR detection system (BioRad) under the following conditions: initial reverse transcription at 50° C. for 30 min, followed by initial denaturation at 95° C. for 5 min, 40 cycles of denaturation at 95° C. for 15 s and annealing and extension at 57° C. for 30 s. To generate quantitative data, a PEDV ultramer was included in each run (Integrated DNA Technologies). The lyophilized ultramer (4 nmol) was resuspended in DEPC-treated, nuclease-free sterile water to generate a stock concentration of 1.0E+10 genomic copies per µl (gc/µl). From the stock ultramer, 10 fold serial dilutions from 1.0E+08 to 1.0E+01 were made in the DEPC-treated water. The concentration was confirmed by qubit dsDNA HS Assay prior to use. The optical data were analyzed using CFX Manager software. For each determination, the threshold lines were automatically calculated using the regression setting for cycle threshold (Ct) determination mode. Baseline subtraction was done automatically using the baseline subtracted mode. Curves with baseline end values of less than 10 were manually corrected.

TABLE 2

Probe (Pr), primer (F/R), and ultramer sequences used for the internally derived RT-qPCR-system.

| Probe/primer name | Sequence |
|---|---|
| 0086-001-1 Pr | 56-FAM/ACAGAGCCTGTGTTGGTGTATAGTAACAT/3BHQ_1 (SEQ ID NO: 41) |
| 0089-065-1 F | TATAGTGGGTGTTATTTCTAGTT (SEQ ID NO: 42) |
| 0086-001-2 R | GCCAATACTGCCAGATTTACA (SEQ ID NO: 43) |

TABLE 2-continued Probe (Pr), primer (F/R), and ultramer sequences used for the
internally derived RT-qPCR-system.

| Probe/primer name | Sequence |
|---|---|
| PEDV-ultramer | 5'/TGATGATATAGTGGGTGTTATTTCTAGTTTGTCTAGCTCCACTT TTAACAGTACTAGGGAGTTGCCTGGTTTCTTCTACCATTCTAATG ATGGCTCTAATTGTACAGAGCCTGTGTTGGTGTATAGTAACATAG GTGTTTGTAAATCTGGCAGTATTGGCTATGTCCCAT/3' (SEQ ID NO: 44) |

Antibody Detection

An in house developed CCIF assay was used to test serum and milk samples from this study: A wild-type PEDV isolate (Genogroup 2a) was diluted 1:100 into PEDV growth media (MEM+2.5% HEPES+0.3% Tryptose phosphate broth+ 0.02% yeast+10 μg/mL trypsin). The diluted virus (100 μL/well) was inoculated onto two-day old 96-well plates planted with VERO cells. Prior to infection, cell growth media was removed from the plates and they were washed twice with 100 μL of PEDV growth media. Plates were incubated for 24 hours at 37±2° C.+CO2 (4-6%). Following incubation, the supernatant was discarded and plates were washed twice with 200 μL/well 1×PBS. For fixation, 200 μL/well of Ethanol was added. Plates were incubated at room temperature for 30 minutes, air-dried, then stored at −20° C. until use. Prior to use in the assay, plates were rehydrated with 200 μl well 1×PBS (Gibco) for 10 min at room temperature and blocked with 100 μl/well buffer (1×PBS+1% normal goat serum+0.1% triton X) for 15 minutes at 37° C. Serial two-fold dilutions of serum samples were prepared in a dilution buffer (1×PBS+5% BSA+1% normal goat serum+0.1% titron-X 100) containing a 1:1000 dilution of PEDV Mab antibody (Median diagnostics). Diluted samples (50 μl/well) were added to the prepared plates and incubated at 37° C. for 1 hour. Following incubation, plates were washed three times with 200 μl/well 1×PBS. A total of 50 μl/well of diluted secondary antibodies [Alexa594 goat anti-mouse IgG (Fisher, 1:500 dilution); FITC labeled, goat anti-pig IgG (BioRad, 1:500 dilution); Hoechst 33342 (Fisher, 1:1000 dilution)] was then added to each plate and incubated at 37° C. for 1 hour. Following incubation, plates were washed three times with 200 μl/well 1×PBS. Fluorescence was observed where PEDV-infected cells bound by Mab3F12 showed specific red fluorescence. Co-localization of green fluorescence indicated binding of pig IgG. The highest dilution where specific green fluorescence was detected was equivalent to the IgG titer.

Results

Mortalities

In group 1 (strict control) 40 pigs survived, in group 2 (challenge control) 16 pigs survived, and in group 3 (CDV-PEDV-G2a spike vaccinated) 34 pigs survived, resulting in an average mortality of 2% (group 1), 80% (group 2), and 59% (group 3), respectively.

Antibody Response

Specific PEDV antibody response after challenge revealed that the mean levels of CCIF IgG antibody titers in the sow sera and milk were higher in the CDV-PEDV-G2a spike vaccinated group than in group 2 (challenge control). This indicates that the vaccinated sows were strongly responding by boosting the IgG levels in milk and sera after contracting the virus from infected piglets post challenge. In comparison to this, the antibody titers of the sows of the challenge control, merely resulting from PEDV infection through contact with the challenged piglets (and their feces), were significantly lower.

Shedding of Virus

On day 3 post challenge virus inoculation, relatively similar mean RNA loads were detected in the vaccinated and non-vaccinated group, reaching 9,2 and 9,8 group mean log 10 PEDV genomic copies for the CDV-PEDV-G2a spike vaccinated group and the challenge control group, respectively. On D48 (7 dpi) and D55 (14 dpi), the mean log 10 PEDV genomic copy number in the CDV-PEDV-G2a spike vaccinated group were 3.2 and 2.0 logs 10, respectively, while in the challenge control group were 5.5 and 3.9 logs 10, respectively, indicating the reduction of 2.3 and 1.9 logs on days 7 and 14 pi, respectively. Although no longer term monitoring of shedding has been performed, the tendency of dynamics of shedding observed on days 7 and 14 post challenge virus inoculation clearly indicates a shortened shedding time in the vaccinated animals in accordance with the results as described above under Example 4.

No PEDV genome could be detected in swabs of the strict negative control group.

In conclusion, the outcome of the study was that piglets born by or, respectively, suckled by sows vaccinated with the CDV PEDV-G2a spike recombinant vaccine showed a significant reduction of mortality, as compared to the piglets of the control group, when challenged with a highly virulent PEDV strain. Also, these piglets receiving PEDV protective IgG antibodies from milk, via transfer of maternal antibodies in the initial days post partum, revealed a significant reduction of virus shedding post challenge, which is an important epidemiological parameter, on days 7 and 14 post infection.

What is claimed is:

1. A nucleic acid molecule encoding a porcine epidemic diarrhea virus (PEDV) spike (S) protein selected from the group consisting of the following (a) and (b):
  (a) a genotype 2a (G2a) PEDV S protein having at least one mutation, wherein
    the leucine residue at amino acid position 900 is substituted by an amino acid residue other than a leucine residue, and/or
    the leucine residue at amino acid position 901 is substituted by an amino acid residue other than a leucine residue,
    the tyrosine residue at amino acid position 1377 is substituted by an amino acid residue other than a tyrosine residue, and/or
    the histidine residue at amino acid position 1384 is substituted by an amino acid residue other than a histidine residue,
  wherein the numbering of the amino acid positions refers to the amino acid sequence of wild type G2a PEDV S protein of SEQ ID NO:2 or SEQ ID NO:39,
  (b) a genotype 2b (G2b) PEDV S protein having at least one mutation, wherein
    the leucine residue at amino acid position 897 is substituted by an amino acid residue other than a leucine residue, and/or
    the leucine residue at amino acid position 898 is substituted by an amino acid residue other than a leucine residue,
    the tyrosine residue at amino acid position 1374 is substituted by an amino acid residue other than a tyrosine residue, and/or
    the histidine residue at amino acid position 1381 is substituted by an amino acid residue other than a histidine residue,
  wherein the numbering of the amino acid positions refers to the amino acid sequence of wild type G2b PEDV S protein of SEQ ID NO:3.

2. The nucleic acid molecule of claim 1, wherein said amino acid residue other than a leucine residue is selected from the group consisting of alanine residue, glycine residue, isoleucine residue, methionine residue and valine residue.

3. The nucleic acid molecule of claim 1, wherein the numbering of the amino acid positions refer to the amino acid sequence RSXIEDLLF (SEQ ID NO:4) of wild type G PEDV S protein, wherein R is the conserved arginine residue of the S 1/S2 cleavage site and LL are the amino acid positions 900 and 901 within the genotype 2a (G2a) PEDV S protein or LL are the amino acid positions 897 and 898 within the genotype 2b (G2b) PEDV S protein.

4. A nucleic acid molecule encoding a porcine epidemic diarrhea virus (PEDV) spike (S) protein comprising the amino acid sequence $$RSX_1IEDX_2X_3, \quad (SEQ\ ID\ NO:\ 1)$$

wherein R is the conserved arginine residue of the S1/S2 cleavage site of said PEDV S protein, $X_1$ can be any amino acid residue, and wherein
  $X_2$ is an amino acid residue other than a leucine residue and $X_3$ is an amino acid residue other than a leucine residue;
wherein said PEDV S protein further comprises the amino acid sequence $$X_1X_2X_3FX_4KX_5X_6X_7X_8, \quad (SEQ\ ID\ NO:\ 6)$$

wherein $X_8$ is the C-terminal amino acid residue of said PEDV S protein or the amino acid residue at the −2 position relative to the C-terminal amino acid position of said PEDV S protein,
$X_2$ to $X_5$, $X_7$ and $X_8$ can be any amino acid residue, and wherein
$X_1$ is an amino acid residue other than a tyrosine residue and $X_6$ is a histidine residue.

5. The nucleic acid molecule of claim 1 or 4, wherein said PEDV S protein comprises the amino acid sequence RSX-IEDAAF (SEQ ID NO:5), wherein R is the conserved arginine residue of the S1/S2 cleavage site of said PEDV S protein and AA are the amino acid positions 900 and 901 within the genotype 2a (G2a) PEDV S protein or AA are the amino acid positions 897 and 898 within the genotype 2b (G2b) PEDV S protein.

6. The nucleic acid molecule of claim 5 wherein
  said amino acid residue other than a tyrosine residue is selected from the group consisting of alanine residue, glycine residue, leucine residue, isoleucine residue, methionine residue and valine residue, and/or
  said amino acid residue other than a histidine residue is an arginine residue.

7. The nucleic acid molecule of claim 1 or 4, wherein said PEDV S protein:
  i) (a) comprises or consists of an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence of any one of SEQ ID NO's: 15, 16, 17, 18, 19, 20, 40, or
  (b) comprises or consists of an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence of any one of SEQ ID NO's: 9, 10, 11, 12, 13, 14; and/or
  ii) (a) is encoded by a nucleotide sequence encoding an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence any one of SEQ ID NO's: 15, 16, 17, 18, 19, 20, 40, or (b) is encoded by a nucleotide sequence encoding an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence of any one of SEQ ID NO's: 9, 10, 11, 12, 13, 14.

8. A PEDV (S) protein encoded by the nucleic acid molecule of claim 1 or 4.

9. The nucleic acid molecule of claim 1 or 4, wherein said nucleic acid molecule encoding the PEDV S protein is recombinant.

10. A vector comprising the nucleic acid molecule of claim 1 or 4.

11. An immunogenic composition comprising the nucleic acid molecule encoding the PEDV S protein of claim 1 or 4.

12. A method of immunizing a subject comprising administering to the subject an immunogenic composition of claim 11.

13. A method of reducing or preventing the clinical signs or disease caused by an infection with a PEDV in a piglet, the method comprising suckling the piglet to a sow to which the immunogenic composition of claim 11 has been administered.

14. A method of reducing the mortality caused by an infection with a PEDV in a piglet, the method comprising suckling the piglet to a sow to which the immunogenic composition of claim 11 has been administered.

15. The method of claim 12, wherein said immunogenic composition is administered intranasal, mucosal, oral, intradermal or intramuscular.

* * * * *

SEQUENCE LISTING

<160> NUMBER OF SEQ ID NOS: 44

<210> SEQ ID NO 1

```
<211> LENGTH: 8
<212> TYPE: PRT
<213> ORGANISM: Artificial Sequence
<220> FEATURE:
<223> OTHER INFORMATION: sequence of fusion domain including X1, X2, and
      X3
<220> FEATURE:
<221> NAME/KEY: VARIANT
<222> LOCATION: (3)..(3)
<223> OTHER INFORMATION: X at residue 3 can be any amino acid residue
<220> FEATURE:
<221> NAME/KEY: VARIANT
<222> LOCATION: (7)..(7)
<223> OTHER INFORMATION: X at residue 7 is a leucine residue, or X at
      residue 7 is an amino acid residue other than a leucine residue
<220> FEATURE:
<221> NAME/KEY: VARIANT
<222> LOCATION: (8)..(8)
<223> OTHER INFORMATION: X at residue 8 is a leucine residue, or X at
      residue 8 is an amino acid residue other than a leucine residue

<400> SEQUENCE: 1

Arg Ser Xaa Ile Glu Asp Xaa Xaa
1               5

<210> SEQ ID NO 2
<211> LENGTH: 1388
<212> TYPE: PRT
<213> ORGANISM: porcine epidemic diarrhea virus

<400> SEQUENCE: 2

Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Asn Thr Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ile Gly Glu Asn Gln Gly Val Asn Ser Thr
    50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
            100                 105                 110

Thr Asn Gly Asn Thr Asn Ala Thr Ala Arg Leu Arg Ile Cys Gln Phe
        115                 120                 125

Pro Ser Ile Lys Thr Leu Gly Pro Thr Ala Asn Asn Asp Val Thr Thr
    130                 135                 140

Gly Arg Asn Cys Leu Phe Asn Lys Ala Ile Pro Ala His Met Ser Glu
145                 150                 155                 160

His Ser Val Val Gly Ile Thr Trp Asp Asn Asp Arg Val Thr Val Phe
                165                 170                 175

Ser Asp Lys Ile Tyr Tyr Phe Tyr Phe Lys Asn Asp Trp Ser Arg Val
            180                 185                 190

Ala Thr Lys Cys Tyr Asn Ser Gly Gly Cys Ala Met Gln Tyr Val Tyr
        195                 200                 205

Glu Pro Thr Tyr Tyr Met Leu Asn Val Thr Ser Ala Gly Glu Asp Gly
    210                 215                 220

Ile Ser Tyr Gln Pro Cys Thr Ala Asn Cys Ile Gly Tyr Ala Ala Asn
225                 230                 235                 240
```

```
Val Phe Ala Thr Glu Pro Asn Gly His Ile Pro Glu Gly Phe Ser Phe
                245                 250                 255

Asn Asn Trp Phe Leu Leu Ser Asn Asp Ser Thr Leu Val His Gly Lys
            260                 265                 270

Val Val Ser Asn Gln Pro Leu Leu Val Asn Cys Leu Leu Ala Ile Pro
        275                 280                 285

Lys Ile Tyr Gly Leu Gly Gln Phe Phe Ser Phe Asn Gln Thr Ile Asp
    290                 295                 300

Gly Val Cys Asn Gly Ala Val Gln Arg Ala Pro Glu Ala Leu Arg
305                 310                 315                 320

Phe Asn Ile Asn Asp Thr Ser Val Ile Leu Ala Glu Gly Ser Ile Val
                325                 330                 335

Leu His Thr Ala Leu Gly Thr Asn Phe Ser Phe Val Cys Ser Asn Ser
            340                 345                 350

Ser Asn Pro His Leu Ala Thr Phe Ala Ile Pro Leu Gly Ala Thr Gln
        355                 360                 365

Val Pro Tyr Tyr Cys Phe Leu Lys Val Asp Thr Tyr Asn Ser Thr Val
    370                 375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
                405                 410                 415

Gly Leu Leu Asp Ala Val Thr Ile Asn Phe Thr Gly His Gly Thr Asp
            420                 425                 430

Asp Asp Val Ser Gly Phe Trp Thr Ile Ala Ser Thr Asn Phe Val Asp
        435                 440                 445

Ala Leu Ile Glu Val Gln Gly Thr Ala Ile Gln Arg Ile Leu Tyr Cys
    450                 455                 460

Asp Asp Pro Val Ser Gln Leu Lys Cys Ser Gln Val Ala Phe Asp Leu
465                 470                 475                 480

Asp Asp Gly Phe Tyr Pro Ile Ser Ser Arg Asn Leu Leu Ser His Glu
                485                 490                 495

Gln Pro Ile Ser Phe Val Thr Leu Pro Ser Phe Asn Asp His Ser Phe
            500                 505                 510

Val Asn Ile Thr Val Ser Ala Ser Phe Gly Gly His Ser Gly Ala Asn
        515                 520                 525

Leu Ile Ala Ser Asp Thr Thr Ile Asn Gly Phe Ser Ser Phe Cys Val
    530                 535                 540

Asp Thr Arg Gln Phe Thr Ile Ser Leu Phe Tyr Asn Val Thr Asn Ser
545                 550                 555                 560

Tyr Gly Tyr Val Ser Lys Ser Gln Asp Ser Asn Cys Pro Phe Thr Leu
                565                 570                 575

Gln Ser Val Asn Asp Tyr Leu Ser Phe Ser Lys Phe Cys Val Ser Thr
            580                 585                 590

Ser Leu Leu Ala Ser Ala Cys Thr Ile Asp Leu Phe Gly Tyr Pro Glu
        595                 600                 605

Phe Gly Ser Gly Val Lys Phe Thr Ser Leu Tyr Phe Gln Phe Thr Lys
    610                 615                 620

Gly Glu Leu Ile Thr Gly Thr Pro Lys Pro Leu Glu Gly Val Thr Asp
625                 630                 635                 640

Val Ser Phe Met Thr Leu Asp Val Cys Thr Lys Tyr Thr Ile Tyr Gly
                645                 650                 655

Phe Lys Gly Glu Gly Ile Ile Thr Leu Thr Asn Ser Ser Phe Leu Ala
```

-continued

```
                660                 665                 670
Gly Val Tyr Tyr Thr Ser Asp Ser Gly Gln Leu Leu Ala Phe Lys Asn
            675                 680                 685

Val Thr Ser Gly Ala Val Tyr Ser Val Thr Pro Cys Ser Phe Ser Glu
690                 695                 700

Gln Ala Ala Tyr Val Asp Asp Ile Val Gly Val Ile Ser Ser Leu
705                 710                 715                 720

Ser Ser Ser Thr Phe Asn Ser Thr Arg Glu Leu Pro Gly Phe Phe Tyr
                725                 730                 735

His Ser Asn Asp Gly Ser Asn Cys Thr Glu Pro Val Leu Val Tyr Ser
                740                 745                 750

Asn Ile Gly Val Cys Lys Ser Gly Ser Ile Gly Tyr Val Pro Ser Gln
            755                 760                 765

Ser Gly Gln Val Lys Ile Ala Pro Thr Val Thr Gly Asn Ile Ser Ile
770                 775                 780

Pro Thr Asn Phe Ser Met Ser Ile Arg Thr Glu Tyr Leu Gln Leu Tyr
785                 790                 795                 800

Asn Thr Pro Val Ser Val Asp Cys Ala Thr Tyr Val Cys Asn Gly Asn
                805                 810                 815

Ser Arg Cys Lys Gln Leu Leu Thr Gln Tyr Thr Ala Ala Cys Lys Thr
                820                 825                 830

Ile Glu Ser Ala Leu Gln Leu Ser Ala Arg Leu Glu Ser Val Glu Val
            835                 840                 845

Asn Ser Met Leu Thr Ile Ser Glu Glu Ala Leu Gln Leu Ala Thr Ile
850                 855                 860

Ser Ser Phe Asn Gly Asp Gly Tyr Asn Phe Thr Asn Val Leu Gly Val
865                 870                 875                 880

Ser Val Tyr Asp Pro Ala Ser Gly Arg Val Val Gln Lys Arg Ser Phe
                885                 890                 895

Ile Glu Asp Leu Leu Phe Asn Lys Val Val Thr Asn Gly Leu Gly Thr
            900                 905                 910

Val Asp Glu Asp Tyr Lys Arg Cys Ser Asn Gly Arg Ser Val Ala Asp
            915                 920                 925

Leu Val Cys Ala Gln Tyr Tyr Ser Gly Val Met Val Leu Pro Gly Val
930                 935                 940

Val Asp Ala Glu Lys Leu His Met Tyr Ser Ala Ser Leu Ile Gly Gly
945                 950                 955                 960

Met Val Leu Gly Gly Phe Thr Ser Ala Ala Leu Pro Phe Ser Tyr
            965                 970                 975

Ala Val Gln Ala Arg Leu Asn Tyr Leu Ala Leu Gln Thr Asp Val Leu
            980                 985                 990

Gln Arg Asn Gln Gln Leu Leu Ala Glu Ser Phe Asn Ser Ala Ile Gly
            995                 1000                1005

Asn Ile Thr Ser Ala Phe Glu Ser Val Lys Glu Ala Ile Ser Gln
    1010                1015                1020

Thr Ser Lys Gly Leu Asn Thr Val Ala His Ala Leu Thr Lys Val
    1025                1030                1035

Gln Glu Val Val Asn Ser Gln Gly Ala Ala Leu Thr Gln Leu Thr
    1040                1045                1050

Val Gln Leu Gln His Asn Phe Gln Ala Ile Ser Ser Ser Ile Asp
    1055                1060                1065

Asp Ile Tyr Ser Arg Leu Asp Ile Leu Ser Ala Asp Val Gln Val
    1070                1075                1080
```

```
Asp Arg Leu Ile Thr Gly Arg Leu Ser Ala Leu Asn Ala Phe Val
    1085            1090                1095

Ala Gln Thr Leu Thr Lys Tyr Thr Glu Val Gln Ala Ser Arg Lys
    1100            1105                1110

Leu Ala Gln Gln Lys Val Asn Glu Cys Val Lys Ser Gln Ser Gln
    1115            1120                1125

Arg Tyr Gly Phe Cys Gly Gly Asp Gly Glu His Ile Phe Ser Leu
    1130            1135                1140

Val Gln Ala Ala Pro Gln Gly Leu Leu Phe Leu His Thr Val Leu
    1145            1150                1155

Val Pro Ser Asp Phe Val Asp Val Ile Ala Ile Ala Gly Leu Cys
    1160            1165                1170

Val Asn Asp Glu Ile Ala Leu Thr Leu Arg Glu Pro Gly Leu Val
    1175            1180                1185

Leu Phe Thr His Glu Leu Gln Asn His Thr Ala Thr Glu Tyr Phe
    1190            1195                1200

Val Ser Ser Arg Arg Met Phe Glu Pro Arg Lys Pro Thr Val Ser
    1205            1210                1215

Asp Phe Val Gln Ile Glu Ser Cys Val Val Thr Tyr Val Asn Leu
    1220            1225                1230

Thr Arg Asp Gln Leu Pro Asp Val Ile Pro Asp Tyr Ile Asp Val
    1235            1240                1245

Asn Lys Thr Leu Asp Glu Ile Leu Ala Ser Leu Pro Asn Arg Thr
    1250            1255                1260

Gly Pro Ser Leu Pro Leu Asp Val Phe Asn Ala Thr Tyr Leu Asn
    1265            1270                1275

Leu Thr Gly Glu Ile Ala Asp Leu Glu Gln Arg Ser Glu Ser Leu
    1280            1285                1290

Arg Asn Thr Thr Glu Glu Leu Gln Ser Leu Ile Tyr Asn Ile Asn
    1295            1300                1305

Asn Thr Leu Val Asp Leu Glu Trp Leu Asn Arg Val Glu Thr Tyr
    1310            1315                1320

Ile Lys Trp Pro Trp Trp Val Trp Leu Ile Ile Phe Ile Val Leu
    1325            1330                1335

Ile Phe Val Val Ser Leu Leu Val Phe Cys Cys Ile Ser Thr Gly
    1340            1345                1350

Cys Cys Gly Cys Cys Gly Cys Cys Cys Ala Cys Phe Ser Gly Cys
    1355            1360                1365

Cys Arg Gly Pro Arg Leu Gln Pro Tyr Glu Val Phe Glu Lys Val
    1370            1375                1380

His Val Gln Cys Gly
    1385

<210> SEQ ID NO 3
<211> LENGTH: 1383
<212> TYPE: PRT
<213> ORGANISM: porcine epidemic diarrhea virus

<400> SEQUENCE: 3

Met Lys Ser Leu Asn Tyr Phe Trp Leu Phe Leu Pro Val Leu Ser Thr
1               5                   10                  15

Leu Ser Leu Pro Gln Asp Val Thr Arg Cys Gln Ser Thr Ile Asn Phe
                20                  25                  30

Arg Arg Phe Phe Ser Lys Phe Asn Val Gln Ala Pro Ala Val Val Val
```

-continued

```
                35                  40                  45
Leu Gly Gly Tyr Leu Pro Ser Met Asn Ser Ser Trp Tyr Cys Gly
            50                  55                  60
Thr Gly Leu Glu Thr Ala Ser Gly Val His Gly Ile Phe Leu Ser Tyr
65                  70                  75                  80
Ile Asp Ala Gly Gln Gly Phe Glu Ile Gly Ile Ser Gln Glu Pro Phe
                85                  90                  95
Asp Pro Ser Gly Tyr Gln Leu Tyr Leu His Lys Ala Thr Asn Gly Asn
                100                 105                 110
His Asn Ala Ile Ala Arg Leu Arg Ile Cys Gln Phe Pro Asn Asn Lys
            115                 120                 125
Thr Leu Gly Pro Thr Val Asn Asp Val Thr Thr Gly Arg Asn Cys Leu
        130                 135                 140
Phe Asn Lys Ala Ile Pro Ala Tyr Met Gln Asp Gly Lys Asn Ile Val
145                 150                 155                 160
Val Gly Ile Thr Trp Asp Asn Asp Arg Val Thr Val Phe Ala Asp Lys
                165                 170                 175
Ile Tyr His Phe Tyr Leu Lys Asn Asp Trp Ser Arg Val Ala Thr Arg
            180                 185                 190
Cys Tyr Asn Lys Arg Ser Cys Ala Met Gln Tyr Val Tyr Thr Pro Thr
        195                 200                 205
Tyr Tyr Met Leu Asn Val Thr Ser Ala Gly Glu Asp Gly Ile Tyr Tyr
    210                 215                 220
Glu Pro Cys Thr Ala Asn Cys Ser Gly Tyr Ala Val Asn Val Phe Ala
225                 230                 235                 240
Thr Asp Ser Asn Gly His Ile Pro Glu Gly Phe Ser Phe Asn Asn Trp
                245                 250                 255
Phe Leu Leu Ser Asn Asp Ser Thr Leu Leu His Gly Lys Val Val Ser
            260                 265                 270
Asn Gln Pro Leu Leu Val Asn Cys Leu Leu Ala Ile Pro Lys Ile Tyr
        275                 280                 285
Gly Leu Gly Gln Phe Phe Ser Phe Asn Gln Thr Met Asp Gly Val Cys
    290                 295                 300
Asn Gly Ala Ala Ala Gln Arg Ala Pro Glu Ala Leu Arg Phe Asn Ile
305                 310                 315                 320
Asn Asp Thr Ser Val Ile Leu Ala Glu Gly Ser Ile Val Leu His Thr
                325                 330                 335
Ala Leu Gly Thr Asn Leu Ser Phe Val Cys Ser Asn Ser Ser Asp Pro
            340                 345                 350
His Leu Ala Thr Phe Thr Ile Pro Leu Gly Ala Thr Gln Val Pro Tyr
        355                 360                 365
Tyr Cys Phe Leu Lys Val Asp Thr Tyr Asn Ser Asn Val Tyr Lys Phe
    370                 375                 380
Leu Ala Val Leu Pro Pro Thr Val Arg Glu Ile Val Ile Thr Lys Tyr
385                 390                 395                 400
Gly Asp Val Tyr Val Asn Gly Phe Gly Tyr Leu His Leu Gly Leu Leu
                405                 410                 415
Asp Ala Val Thr Ile Asn Phe Thr Gly His Gly Thr Asp Asp Asp Val
            420                 425                 430
Ser Gly Phe Trp Thr Ile Ala Ser Thr Asn Phe Val Asp Ala Leu Ile
        435                 440                 445
Glu Val Gln Gly Thr Ala Ile Gln Arg Ile Leu Tyr Cys Asp Asp Pro
    450                 455                 460
```

```
Val Ser Gln Leu Lys Cys Ser Gln Val Ala Phe Asp Leu Asp Asp Gly
465                 470                 475                 480

Phe Tyr Pro Ile Ser Ser Arg Asn Leu Leu Ser His Glu Gln Pro Ile
            485                 490                 495

Ser Phe Val Thr Leu Pro Ser Phe Asn Asp His Ser Phe Val Asn Ile
            500                 505                 510

Thr Val Ser Ala Ser Phe Gly Gly His Ser Gly Ala Asn Leu Ile Ala
            515                 520                 525

Ser Asp Thr Thr Ile Asn Gly Phe Ser Ser Phe Cys Val Asp Thr Arg
530                 535                 540

Gln Phe Thr Ile Ser Leu Phe Tyr Asn Val Thr Asn Ser Tyr Gly Tyr
545                 550                 555                 560

Val Ser Lys Ser Gln Asp Ser Asn Cys Pro Phe Thr Leu Gln Ser Val
                565                 570                 575

Asn Asp Tyr Leu Ser Phe Ser Lys Phe Cys Val Ser Thr Ser Leu Leu
            580                 585                 590

Ala Ser Ala Cys Thr Ile Asp Leu Phe Gly Tyr Pro Glu Phe Gly Ser
            595                 600                 605

Gly Val Lys Phe Thr Ser Leu Tyr Phe Gln Phe Thr Glu Gly Glu Leu
            610                 615                 620

Ile Thr Gly Thr Pro Lys Pro Leu Glu Gly Val Thr Asp Val Ser Phe
625                 630                 635                 640

Met Thr Leu Asp Val Cys Thr Lys Tyr Thr Ile Tyr Gly Phe Lys Gly
                645                 650                 655

Glu Gly Ile Ile Thr Leu Thr Asn Ser Ser Phe Leu Ala Gly Val Tyr
            660                 665                 670

Tyr Thr Ser Asp Ser Gly Gln Leu Leu Ala Phe Lys Asn Val Thr Ser
            675                 680                 685

Gly Ala Val Tyr Ser Val Thr Pro Cys Ser Phe Ser Glu Gln Ala Ala
            690                 695                 700

Tyr Val Asp Asp Asp Ile Val Gly Val Ile Ser Ser Leu Ser Ser Ser
705                 710                 715                 720

Thr Phe Asn Ser Thr Arg Glu Leu Pro Gly Phe Phe Tyr His Ser Asn
                725                 730                 735

Asp Gly Ser Asn Cys Thr Glu Pro Val Leu Val Tyr Ser Asn Ile Gly
            740                 745                 750

Val Cys Lys Ser Gly Ser Ile Gly Tyr Val Pro Ser Gln Ser Gly Gln
            755                 760                 765

Val Lys Ile Ala Pro Thr Val Thr Gly Asn Ile Ser Ile Pro Thr Asn
            770                 775                 780

Phe Ser Met Ser Ile Arg Thr Glu Tyr Leu Gln Leu Tyr Asn Thr Pro
785                 790                 795                 800

Val Ser Val Asp Cys Ala Thr Tyr Val Cys Asn Gly Asn Ser Arg Cys
                805                 810                 815

Lys Gln Leu Leu Thr Gln Tyr Thr Ala Ala Cys Lys Thr Ile Glu Ser
            820                 825                 830

Ala Leu Gln Leu Ser Ala Arg Leu Glu Ser Val Glu Val Asn Ser Met
            835                 840                 845

Leu Thr Ile Ser Glu Glu Ala Leu Gln Leu Ala Thr Ile Ser Ser Phe
            850                 855                 860

Asn Gly Asp Gly Tyr Asn Phe Thr Asn Val Leu Gly Val Ser Val Tyr
865                 870                 875                 880
```

```
Asp Pro Ala Ser Gly Arg Val Val Gln Lys Arg Ser Phe Ile Glu Asp
                885                 890                 895

Leu Leu Phe Asn Lys Val Val Thr Asn Gly Leu Gly Thr Val Asp Glu
            900                 905                 910

Asp Tyr Lys Arg Cys Ser Asn Gly Arg Ser Val Ala Asp Leu Val Cys
        915                 920                 925

Ala Gln Tyr Tyr Ser Gly Val Met Val Leu Pro Gly Val Val Asp Ala
    930                 935                 940

Glu Lys Leu His Met Tyr Ser Ala Ser Leu Ile Gly Gly Met Val Leu
945                 950                 955                 960

Gly Gly Phe Thr Ser Ala Ala Ala Leu Pro Phe Ser Tyr Ala Val Gln
                965                 970                 975

Ala Arg Leu Asn Tyr Leu Ala Leu Gln Thr Asp Val Leu Gln Arg Asn
            980                 985                 990

Gln Gln Leu Leu Ala Glu Ser Phe Asn Ser Ala Ile Gly Asn Ile Thr
        995                 1000                1005

Ser Ala Phe Glu Ser Val Lys Glu Ala Ile Ser Gln Thr Ser Lys
    1010                1015                1020

Gly Leu Asn Thr Val Ala His Ala Leu Thr Lys Val Gln Glu Val
    1025                1030                1035

Val Asn Ser Gln Gly Ala Ala Leu Thr Gln Leu Thr Val Gln Leu
    1040                1045                1050

Gln His Asn Phe Gln Ala Ile Ser Ser Ser Ile Asp Asp Ile Tyr
    1055                1060                1065

Ser Arg Leu Asp Ile Leu Ser Ala Asp Val Gln Val Asp Arg Leu
    1070                1075                1080

Ile Thr Gly Arg Leu Ser Ala Leu Asn Ala Phe Val Ala Gln Thr
    1085                1090                1095

Leu Thr Lys Tyr Thr Glu Val Gln Ala Ser Arg Lys Leu Ala Gln
    1100                1105                1110

Gln Lys Val Asn Glu Cys Val Lys Ser Gln Ser Gln Arg Tyr Gly
    1115                1120                1125

Phe Cys Gly Gly Asp Gly Glu His Ile Phe Ser Leu Val Gln Ala
    1130                1135                1140

Ala Pro Gln Gly Leu Leu Phe Leu His Thr Val Leu Val Pro Gly
    1145                1150                1155

Asp Phe Ile Asp Val Ile Ala Ile Ala Gly Leu Cys Val Asn Asp
    1160                1165                1170

Glu Ile Ala Leu Thr Leu Arg Glu Pro Gly Leu Val Leu Phe Thr
    1175                1180                1185

His Glu Leu Gln Asn His Thr Ala Thr Glu Tyr Phe Val Ser Ser
    1190                1195                1200

Arg Arg Met Phe Glu Pro Arg Lys Pro Thr Val Ser Asp Phe Val
    1205                1210                1215

Gln Ile Glu Ser Cys Val Val Thr Tyr Val Asn Leu Thr Arg Asp
    1220                1225                1230

Gln Leu Pro Asp Val Ile Pro Asp Tyr Ile Asp Val Asn Lys Thr
    1235                1240                1245

Leu Asp Glu Ile Leu Ala Ser Leu Pro Asn Arg Thr Gly Pro Ser
    1250                1255                1260

Leu Pro Leu Asp Val Phe Asn Ala Thr Tyr Leu Asn Leu Thr Gly
    1265                1270                1275

Glu Ile Ala Asp Leu Glu Gln Arg Ser Glu Ser Leu Arg Asn Thr
```

```
                   1280            1285            1290
Thr Glu Glu Leu Gln Ser Leu Ile Tyr Asn Ile Asn Asn Thr Leu
       1295            1300            1305

Val Asp Leu Glu Trp Leu Asn Arg Val Glu Thr Tyr Ile Lys Trp
       1310            1315            1320

Pro Trp Trp Val Trp Leu Ile Val Phe Ile Val Leu Ile Phe Val
       1325            1330            1335

Val Ser Leu Leu Val Phe Cys Cys Ile Ser Thr Gly Cys Cys Gly
       1340            1345            1350

Cys Cys Gly Cys Cys Cys Ala Cys Phe Ser Gly Cys Cys Arg Gly
       1355            1360            1365

Pro Arg Leu Gln Pro Tyr Glu Val Phe Glu Lys Val His Val Gln
       1370            1375            1380

<210> SEQ ID NO 4
<211> LENGTH: 9
<212> TYPE: PRT
<213> ORGANISM: Artificial Sequence
<220> FEATURE:
<223> OTHER INFORMATION: sequence of fusion domain including X1
<220> FEATURE:
<221> NAME/KEY: VARIANT
<222> LOCATION: (3)..(3)
<223> OTHER INFORMATION: X at residue 3 can be any amino acid residue

<400> SEQUENCE: 4

Arg Ser Xaa Ile Glu Asp Leu Leu Phe
1               5

<210> SEQ ID NO 5
<211> LENGTH: 9
<212> TYPE: PRT
<213> ORGANISM: Artificial Sequence
<220> FEATURE:
<223> OTHER INFORMATION: sequence of fusion domain including X1
<220> FEATURE:
<221> NAME/KEY: VARIANT
<222> LOCATION: (3)..(3)
<223> OTHER INFORMATION: X at residue 3 can be any amino acid residue

<400> SEQUENCE: 5

Arg Ser Xaa Ile Glu Asp Ala Ala Phe
1               5

<210> SEQ ID NO 6
<211> LENGTH: 10
<212> TYPE: PRT
<213> ORGANISM: Artificial Sequence
<220> FEATURE:
<223> OTHER INFORMATION: sequence of fusion domain including X1, X2, X3,
      X4, X5, X6, X7, and X8
<220> FEATURE:
<221> NAME/KEY: VARIANT
<222> LOCATION: (1)..(1)
<223> OTHER INFORMATION: X at residue 1 is a tyrosine residue, or X at
      residue 1 is an amino acid residue other than a tyrosine residue
<220> FEATURE:
<221> NAME/KEY: VARIANT
<222> LOCATION: (2)..(2)
<223> OTHER INFORMATION: X at residue 2 can be any amino acid residue
<220> FEATURE:
<221> NAME/KEY: VARIANT
<222> LOCATION: (3)..(3)
<223> OTHER INFORMATION: X at residue 3 can be any amino acid residue
<220> FEATURE:
<221> NAME/KEY: VARIANT
<222> LOCATION: (5)..(5)
<223> OTHER INFORMATION: X at residue 5 can be any amino acid residue
```

```
<220> FEATURE:
<221> NAME/KEY: VARIANT
<222> LOCATION: (7)..(7)
<223> OTHER INFORMATION: X at residue 7 can be any amino acid residue
<220> FEATURE:
<221> NAME/KEY: VARIANT
<222> LOCATION: (8)..(8)
<223> OTHER INFORMATION: X at residue 8 is a histidine residue, or X at
      residue 8 is an amino acid residue other than a histidine residue
<220> FEATURE:
<221> NAME/KEY: VARIANT
<222> LOCATION: (9)..(9)
<223> OTHER INFORMATION: X at residue 9 can be any amino acid residue
<220> FEATURE:
<221> NAME/KEY: VARIANT
<222> LOCATION: (10)..(10)
<223> OTHER INFORMATION: X at residue 10 can be any amino acid residue

<400> SEQUENCE: 6

Xaa Xaa Xaa Phe Xaa Lys Xaa Xaa Xaa Xaa
1               5                   10

<210> SEQ ID NO 7
<211> LENGTH: 8
<212> TYPE: PRT
<213> ORGANISM: Artificial Sequence
<220> FEATURE:
<223> OTHER INFORMATION: sequence of retention domain
<220> FEATURE:
<221> NAME/KEY: VARIANT
<222> LOCATION: (2)..(2)
<223> OTHER INFORMATION: X at residue 2 can be any amino acid residue
<220> FEATURE:
<221> NAME/KEY: VARIANT
<222> LOCATION: (3)..(3)
<223> OTHER INFORMATION: X at residue 3 can be any amino acid residue
<220> FEATURE:
<221> NAME/KEY: VARIANT
<222> LOCATION: (5)..(5)
<223> OTHER INFORMATION: X at residue 5 can be any amino acid residue
<220> FEATURE:
<221> NAME/KEY: VARIANT
<222> LOCATION: (7)..(7)
<223> OTHER INFORMATION: X at residue 7 can be any amino acid residue

<400> SEQUENCE: 7

Tyr Xaa Xaa Phe Xaa Lys Xaa His
1               5

<210> SEQ ID NO 8
<211> LENGTH: 8
<212> TYPE: PRT
<213> ORGANISM: Artificial Sequence
<220> FEATURE:
<223> OTHER INFORMATION: sequence of retention domain
<220> FEATURE:
<221> NAME/KEY: VARIANT
<222> LOCATION: (2)..(2)
<223> OTHER INFORMATION: X at residue 2 can be any amino acid residue
<220> FEATURE:
<221> NAME/KEY: VARIANT
<222> LOCATION: (3)..(3)
<223> OTHER INFORMATION: X at residue 3 can be any amino acid residue
<220> FEATURE:
<221> NAME/KEY: VARIANT
<222> LOCATION: (5)..(5)
<223> OTHER INFORMATION: X at residue 5 can be any amino acid residue
<220> FEATURE:
<221> NAME/KEY: VARIANT
<222> LOCATION: (7)..(7)
<223> OTHER INFORMATION: X at residue 7 can be any amino acid residue

<400> SEQUENCE: 8

Ala Xaa Xaa Phe Xaa Lys Xaa Arg
```

<210> SEQ ID NO 9
<211> LENGTH: 1383
<212> TYPE: PRT
<213> ORGANISM: porcine epidemic diarrhea virus

<400> SEQUENCE: 9

```
Met Lys Ser Leu Asn Tyr Phe Trp Leu Phe Leu Pro Val Leu Ser Thr
1               5                   10                  15

Leu Ser Leu Pro Gln Asp Val Thr Arg Cys Gln Ser Thr Ile Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ser Met Asn Ser Ser Trp Tyr Cys Gly
    50                  55                  60

Thr Gly Leu Glu Thr Ala Ser Gly Val His Gly Ile Phe Leu Ser Tyr
65                  70                  75                  80

Ile Asp Ala Gly Gln Gly Phe Glu Ile Gly Ile Ser Gln Glu Pro Phe
                85                  90                  95

Asp Pro Ser Gly Tyr Gln Leu Tyr Leu His Lys Ala Thr Asn Gly Asn
            100                 105                 110

His Asn Ala Ile Ala Arg Leu Arg Ile Cys Gln Phe Pro Asn Asn Lys
        115                 120                 125

Thr Leu Gly Pro Thr Val Asn Asp Val Thr Thr Gly Arg Asn Cys Leu
    130                 135                 140

Phe Asn Lys Ala Ile Pro Ala Tyr Met Gln Asp Gly Lys Asn Ile Val
145                 150                 155                 160

Val Gly Ile Thr Trp Asp Asn Asp Arg Val Thr Val Phe Ala Asp Lys
                165                 170                 175

Ile Tyr His Phe Tyr Leu Lys Asn Asp Trp Ser Arg Val Ala Thr Arg
            180                 185                 190

Cys Tyr Asn Lys Arg Ser Cys Ala Met Gln Tyr Val Tyr Thr Pro Thr
        195                 200                 205

Tyr Tyr Met Leu Asn Val Thr Ser Ala Gly Asp Gly Ile Tyr Tyr
    210                 215                 220

Glu Pro Cys Thr Ala Asn Cys Ser Gly Tyr Ala Val Asn Val Phe Ala
225                 230                 235                 240

Thr Asp Ser Asn Gly His Ile Pro Glu Gly Phe Ser Phe Asn Asn Trp
                245                 250                 255

Phe Leu Leu Ser Asn Asp Ser Thr Leu Leu His Gly Lys Val Val Ser
            260                 265                 270

Asn Gln Pro Leu Leu Val Asn Cys Leu Leu Ala Ile Pro Lys Ile Tyr
        275                 280                 285

Gly Leu Gly Gln Phe Phe Ser Phe Asn Gln Thr Met Asp Gly Val Cys
    290                 295                 300

Asn Gly Ala Ala Ala Gln Arg Ala Pro Glu Ala Leu Arg Phe Asn Ile
305                 310                 315                 320

Asn Asp Thr Ser Val Ile Leu Ala Glu Gly Ser Ile Val Leu His Thr
                325                 330                 335

Ala Leu Gly Thr Asn Leu Ser Phe Val Cys Ser Asn Ser Ser Asp Pro
            340                 345                 350

His Leu Ala Thr Phe Thr Ile Pro Leu Gly Ala Thr Gln Val Pro Tyr
        355                 360                 365
```

```
Tyr Cys Phe Leu Lys Val Asp Thr Tyr Asn Ser Asn Val Tyr Lys Phe
    370                 375                 380

Leu Ala Val Leu Pro Pro Thr Val Arg Glu Ile Val Ile Thr Lys Tyr
385                 390                 395                 400

Gly Asp Val Tyr Val Asn Gly Phe Gly Tyr Leu His Leu Gly Leu Leu
                405                 410                 415

Asp Ala Val Thr Ile Asn Phe Thr Gly His Gly Thr Asp Asp Asp Val
                420                 425                 430

Ser Gly Phe Trp Thr Ile Ala Ser Thr Asn Phe Val Asp Ala Leu Ile
            435                 440                 445

Glu Val Gln Gly Thr Ala Ile Gln Arg Ile Leu Tyr Cys Asp Asp Pro
450                 455                 460

Val Ser Gln Leu Lys Cys Ser Gln Val Ala Phe Asp Leu Asp Asp Gly
465                 470                 475                 480

Phe Tyr Pro Ile Ser Ser Arg Asn Leu Leu Ser His Glu Gln Pro Ile
                485                 490                 495

Ser Phe Val Thr Leu Pro Ser Phe Asn Asp His Ser Phe Val Asn Ile
                500                 505                 510

Thr Val Ser Ala Ser Phe Gly Gly His Ser Gly Ala Asn Leu Ile Ala
            515                 520                 525

Ser Asp Thr Thr Ile Asn Gly Phe Ser Ser Phe Cys Val Asp Thr Arg
530                 535                 540

Gln Phe Thr Ile Ser Leu Phe Tyr Asn Val Thr Asn Ser Tyr Gly Tyr
545                 550                 555                 560

Val Ser Lys Ser Gln Asp Ser Asn Cys Pro Phe Thr Leu Gln Ser Val
                565                 570                 575

Asn Asp Tyr Leu Ser Phe Ser Lys Phe Cys Val Ser Thr Ser Leu Leu
                580                 585                 590

Ala Ser Ala Cys Thr Ile Asp Leu Phe Gly Tyr Pro Glu Phe Gly Ser
            595                 600                 605

Gly Val Lys Phe Thr Ser Leu Tyr Phe Gln Phe Thr Glu Gly Glu Leu
            610                 615                 620

Ile Thr Gly Thr Pro Lys Pro Leu Glu Gly Val Thr Asp Val Ser Phe
625                 630                 635                 640

Met Thr Leu Asp Val Cys Thr Lys Tyr Thr Ile Tyr Gly Phe Lys Gly
                645                 650                 655

Glu Gly Ile Ile Thr Leu Thr Asn Ser Ser Phe Leu Ala Gly Val Tyr
            660                 665                 670

Tyr Thr Ser Asp Ser Gly Gln Leu Leu Ala Phe Lys Asn Val Thr Ser
            675                 680                 685

Gly Ala Val Tyr Ser Val Thr Pro Cys Ser Phe Ser Glu Gln Ala Ala
690                 695                 700

Tyr Val Asp Asp Asp Ile Val Gly Val Ile Ser Ser Leu Ser Ser Ser
705                 710                 715                 720

Thr Phe Asn Ser Thr Arg Glu Leu Pro Gly Phe Phe Tyr His Ser Asn
                725                 730                 735

Asp Gly Ser Asn Cys Thr Glu Pro Val Leu Val Tyr Ser Asn Ile Gly
                740                 745                 750

Val Cys Lys Ser Gly Ser Ile Gly Tyr Val Pro Ser Gln Ser Gly Gln
                755                 760                 765

Val Lys Ile Ala Pro Thr Val Thr Gly Asn Ile Ser Ile Pro Thr Asn
770                 775                 780

Phe Ser Met Ser Ile Arg Thr Glu Tyr Leu Gln Leu Tyr Asn Thr Pro
```

```
                785                 790                 795                 800
        Val Ser Val Asp Cys Ala Thr Tyr Val Cys Asn Gly Asn Ser Arg Cys
                        805                 810                 815

Lys Gln Leu Leu Thr Gln Tyr Thr Ala Ala Cys Lys Thr Ile Glu Ser
                        820                 825                 830

Ala Leu Gln Leu Ser Ala Arg Leu Glu Ser Val Glu Val Asn Ser Met
                        835                 840                 845

Leu Thr Ile Ser Glu Glu Ala Leu Gln Leu Ala Thr Ile Ser Ser Phe
                        850                 855                 860

Asn Gly Asp Gly Tyr Asn Phe Thr Asn Val Leu Gly Val Ser Val Tyr
        865                 870                 875                 880

Asp Pro Ala Ser Gly Arg Val Val Gln Lys Arg Ser Phe Ile Glu Asp
                        885                 890                 895

Ala Leu Phe Asn Lys Val Val Thr Asn Gly Leu Gly Thr Val Asp Glu
                        900                 905                 910

Asp Tyr Lys Arg Cys Ser Asn Gly Arg Ser Val Ala Asp Leu Val Cys
                        915                 920                 925

Ala Gln Tyr Tyr Ser Gly Val Met Val Leu Pro Gly Val Val Asp Ala
                        930                 935                 940

Glu Lys Leu His Met Tyr Ser Ala Ser Leu Ile Gly Gly Met Val Leu
        945                 950                 955                 960

Gly Gly Phe Thr Ser Ala Ala Ala Leu Pro Phe Ser Tyr Ala Val Gln
                        965                 970                 975

Ala Arg Leu Asn Tyr Leu Ala Leu Gln Thr Asp Val Leu Gln Arg Asn
                        980                 985                 990

Gln Gln Leu Leu Ala Glu Ser Phe  Asn Ser Ala Ile Gly  Asn Ile Thr
                        995                 1000                1005

Ser Ala  Phe Glu Ser Val Lys  Glu Ala Ile Ser Gln  Thr Ser Lys
                 1010                1015                1020

Gly Leu Asn Thr Val Ala  His Ala Leu Thr Lys Val  Gln Glu Val
                 1025                1030                1035

Val Asn  Ser Gln Gly Ala Ala  Leu Thr Gln Leu Thr  Val Gln Leu
                 1040                1045                1050

Gln His  Asn Phe Gln Ala Ile  Ser Ser Ser Ile Asp  Asp Ile Tyr
                 1055                1060                1065

Ser Arg  Leu Asp Ile Leu Ser  Ala Asp Val Gln Val  Asp Arg Leu
                 1070                1075                1080

Ile Thr  Gly Arg Leu Ser Ala  Leu Asn Ala Phe Val  Ala Gln Thr
                 1085                1090                1095

Leu Thr  Lys Tyr Thr Glu Val  Gln Ala Ser Arg Lys  Leu Ala Gln
                 1100                1105                1110

Gln Lys  Val Asn Glu Cys Val  Lys Ser Gln Ser Gln  Arg Tyr Gly
                 1115                1120                1125

Phe Cys  Gly Gly Asp Gly Glu  His Ile Phe Ser Leu  Val Gln Ala
                 1130                1135                1140

Ala Pro  Gln Gly Leu Leu Phe  Leu His Thr Val Leu  Val Pro Gly
                 1145                1150                1155

Asp Phe  Ile Asp Val Ile Ala  Ile Ala Gly Leu Cys  Val Asn Asp
                 1160                1165                1170

Glu Ile  Ala Leu Thr Leu Arg  Glu Pro Gly Leu Val  Leu Phe Thr
                 1175                1180                1185

His Glu  Leu Gln Asn His Thr  Ala Thr Glu Tyr Phe  Val Ser Ser
                 1190                1195                1200
```

```
Arg Arg Met Phe Glu Pro Arg Lys Pro Thr Val Ser Asp Phe Val
1205                1210                1215

Gln Ile Glu Ser Cys Val Val Thr Tyr Val Asn Leu Thr Arg Asp
1220                1225                1230

Gln Leu Pro Asp Val Ile Pro Asp Tyr Ile Asp Val Asn Lys Thr
1235                1240                1245

Leu Asp Glu Ile Leu Ala Ser Leu Pro Asn Arg Thr Gly Pro Ser
1250                1255                1260

Leu Pro Leu Asp Val Phe Asn Ala Thr Tyr Leu Asn Leu Thr Gly
1265                1270                1275

Glu Ile Ala Asp Leu Glu Gln Arg Ser Glu Ser Leu Arg Asn Thr
1280                1285                1290

Thr Glu Glu Leu Gln Ser Leu Ile Tyr Asn Ile Asn Asn Thr Leu
1295                1300                1305

Val Asp Leu Glu Trp Leu Asn Arg Val Glu Thr Tyr Ile Lys Trp
1310                1315                1320

Pro Trp Trp Val Trp Leu Ile Val Phe Ile Val Leu Ile Phe Val
1325                1330                1335

Val Ser Leu Leu Val Phe Cys Cys Ile Ser Thr Gly Cys Cys Gly
1340                1345                1350

Cys Cys Gly Cys Cys Cys Ala Cys Phe Ser Gly Cys Cys Arg Gly
1355                1360                1365

Pro Arg Leu Gln Pro Tyr Glu Val Phe Glu Lys Val His Val Gln
1370                1375                1380

<210> SEQ ID NO 10
<211> LENGTH: 1383
<212> TYPE: PRT
<213> ORGANISM: porcine epidemic diarrhea virus

<400> SEQUENCE: 10

Met Lys Ser Leu Asn Tyr Phe Trp Leu Phe Leu Pro Val Leu Ser Thr
1                5                  10                  15

Leu Ser Leu Pro Gln Asp Val Thr Arg Cys Gln Ser Thr Ile Asn Phe
                20                  25                  30

Arg Arg Phe Phe Ser Lys Phe Asn Val Gln Ala Pro Ala Val Val Val
            35                  40                  45

Leu Gly Gly Tyr Leu Pro Ser Met Asn Ser Ser Trp Tyr Cys Gly
    50                  55                  60

Thr Gly Leu Glu Thr Ala Ser Gly Val His Gly Ile Phe Leu Ser Tyr
65                  70                  75                  80

Ile Asp Ala Gly Gln Gly Phe Glu Ile Gly Ile Ser Gln Glu Pro Phe
                85                  90                  95

Asp Pro Ser Gly Tyr Gln Leu Tyr Leu His Lys Ala Thr Asn Gly Asn
            100                 105                 110

His Asn Ala Ile Ala Arg Leu Arg Ile Cys Gln Phe Pro Asn Asn Lys
        115                 120                 125

Thr Leu Gly Pro Thr Val Asn Asp Val Thr Thr Gly Arg Asn Cys Leu
    130                 135                 140

Phe Asn Lys Ala Ile Pro Ala Tyr Met Gln Asp Gly Lys Asn Ile Val
145                 150                 155                 160

Val Gly Ile Thr Trp Asp Asn Asp Arg Val Thr Val Phe Ala Asp Lys
                165                 170                 175

Ile Tyr His Phe Tyr Leu Lys Asn Asp Trp Ser Arg Val Ala Thr Arg
```

```
            180              185             190
  Cys Tyr Asn Lys Arg Ser Cys Ala Met Gln Tyr Val Tyr Thr Pro Thr
          195                 200                 205
  Tyr Tyr Met Leu Asn Val Thr Ser Ala Gly Glu Asp Gly Ile Tyr Tyr
          210                 215                 220
  Glu Pro Cys Thr Ala Asn Cys Ser Gly Tyr Ala Val Asn Val Phe Ala
  225                 230                 235                 240
  Thr Asp Ser Asn Gly His Ile Pro Glu Gly Phe Ser Phe Asn Asn Trp
                  245                 250                 255
  Phe Leu Leu Ser Asn Asp Ser Thr Leu Leu His Gly Lys Val Val Ser
                  260                 265                 270
  Asn Gln Pro Leu Leu Val Asn Cys Leu Leu Ala Ile Pro Lys Ile Tyr
                  275                 280                 285
  Gly Leu Gly Gln Phe Phe Ser Phe Asn Gln Thr Met Asp Gly Val Cys
                  290                 295                 300
  Asn Gly Ala Ala Ala Gln Arg Ala Pro Glu Ala Leu Arg Phe Asn Ile
  305                 310                 315                 320
  Asn Asp Thr Ser Val Ile Leu Ala Glu Gly Ser Ile Val Leu His Thr
                  325                 330                 335
  Ala Leu Gly Thr Asn Leu Ser Phe Val Cys Ser Asn Ser Ser Asp Pro
                  340                 345                 350
  His Leu Ala Thr Phe Thr Ile Pro Leu Gly Ala Thr Gln Val Pro Tyr
                  355                 360                 365
  Tyr Cys Phe Leu Lys Val Asp Thr Tyr Asn Ser Asn Val Tyr Lys Phe
          370                 375                 380
  Leu Ala Val Leu Pro Pro Thr Val Arg Glu Ile Val Ile Thr Lys Tyr
  385                 390                 395                 400
  Gly Asp Val Tyr Val Asn Gly Phe Gly Tyr Leu His Leu Gly Leu Leu
                  405                 410                 415
  Asp Ala Val Thr Ile Asn Phe Thr Gly His Gly Thr Asp Asp Asp Val
                  420                 425                 430
  Ser Gly Phe Trp Thr Ile Ala Ser Thr Asn Phe Val Asp Ala Leu Ile
                  435                 440                 445
  Glu Val Gln Gly Thr Ala Ile Gln Arg Ile Leu Tyr Cys Asp Asp Pro
          450                 455                 460
  Val Ser Gln Leu Lys Cys Ser Gln Val Ala Phe Asp Leu Asp Asp Gly
  465                 470                 475                 480
  Phe Tyr Pro Ile Ser Ser Arg Asn Leu Leu Ser His Glu Gln Pro Ile
                  485                 490                 495
  Ser Phe Val Thr Leu Pro Ser Phe Asn Asp His Ser Phe Val Asn Ile
                  500                 505                 510
  Thr Val Ser Ala Ser Phe Gly Gly His Ser Gly Ala Asn Leu Ile Ala
                  515                 520                 525
  Ser Asp Thr Thr Ile Asn Gly Phe Ser Ser Phe Cys Val Asp Thr Arg
                  530                 535                 540
  Gln Phe Thr Ile Ser Leu Phe Tyr Asn Val Thr Asn Ser Tyr Gly Tyr
  545                 550                 555                 560
  Val Ser Lys Ser Gln Asp Ser Asn Cys Pro Phe Thr Leu Gln Ser Val
                  565                 570                 575
  Asn Asp Tyr Leu Ser Phe Ser Lys Phe Cys Val Ser Thr Ser Leu Leu
                  580                 585                 590
  Ala Ser Ala Cys Thr Ile Asp Leu Phe Gly Tyr Pro Glu Phe Gly Ser
                  595                 600                 605
```

-continued

Gly Val Lys Phe Thr Ser Leu Tyr Phe Gln Phe Thr Glu Gly Glu Leu
    610             615             620

Ile Thr Gly Thr Pro Lys Pro Leu Glu Gly Val Thr Asp Val Ser Phe
625             630             635             640

Met Thr Leu Asp Val Cys Thr Lys Tyr Thr Ile Tyr Gly Phe Lys Gly
            645             650             655

Glu Gly Ile Ile Thr Leu Thr Asn Ser Ser Phe Leu Ala Gly Val Tyr
            660             665             670

Tyr Thr Ser Asp Ser Gly Gln Leu Leu Ala Phe Lys Asn Val Thr Ser
        675             680             685

Gly Ala Val Tyr Ser Val Thr Pro Cys Ser Phe Ser Glu Gln Ala Ala
    690             695             700

Tyr Val Asp Asp Ile Val Gly Val Ile Ser Ser Leu Ser Ser Ser
705             710             715             720

Thr Phe Asn Ser Thr Arg Glu Leu Pro Gly Phe Phe Tyr His Ser Asn
                725             730             735

Asp Gly Ser Asn Cys Thr Glu Pro Val Leu Val Tyr Ser Asn Ile Gly
            740             745             750

Val Cys Lys Ser Gly Ser Ile Gly Tyr Val Pro Ser Gln Ser Gly Gln
    755             760             765

Val Lys Ile Ala Pro Thr Val Thr Gly Asn Ile Ser Ile Pro Thr Asn
770             775             780

Phe Ser Met Ser Ile Arg Thr Glu Tyr Leu Gln Leu Tyr Asn Thr Pro
785             790             795             800

Val Ser Val Asp Cys Ala Thr Tyr Val Cys Asn Gly Asn Ser Arg Cys
            805             810             815

Lys Gln Leu Leu Thr Gln Tyr Thr Ala Ala Cys Lys Thr Ile Glu Ser
        820             825             830

Ala Leu Gln Leu Ser Ala Arg Leu Glu Ser Val Glu Val Asn Ser Met
    835             840             845

Leu Thr Ile Ser Glu Glu Ala Leu Gln Leu Ala Thr Ile Ser Ser Phe
850             855             860

Asn Gly Asp Gly Tyr Asn Phe Thr Asn Val Leu Gly Val Ser Val Tyr
865             870             875             880

Asp Pro Ala Ser Gly Arg Val Val Gln Lys Arg Ser Phe Ile Glu Asp
            885             890             895

Leu Ala Phe Asn Lys Val Val Thr Asn Gly Leu Gly Thr Val Asp Glu
        900             905             910

Asp Tyr Lys Arg Cys Ser Asn Gly Arg Ser Val Ala Asp Leu Val Cys
    915             920             925

Ala Gln Tyr Tyr Ser Gly Val Met Val Leu Pro Gly Val Val Asp Ala
930             935             940

Glu Lys Leu His Met Tyr Ser Ala Ser Leu Ile Gly Gly Met Val Leu
945             950             955             960

Gly Gly Phe Thr Ser Ala Ala Ala Leu Pro Phe Ser Tyr Ala Val Gln
            965             970             975

Ala Arg Leu Asn Tyr Leu Ala Leu Gln Thr Asp Val Leu Gln Arg Asn
        980             985             990

Gln Gln Leu Leu Ala Glu Ser Phe Asn Ser Ala Ile Gly Asn Ile Thr
    995             1000            1005

Ser Ala Phe Glu Ser Val Lys Glu Ala Ile Ser Gln Thr Ser Lys
    1010            1015            1020

```
Gly  Leu  Asn  Thr  Val  Ala  His  Ala  Leu  Thr  Lys  Val  Gln  Glu  Val
     1025                ￼    1030                    1035

Val  Asn  Ser  Gln  Gly  Ala  Ala  Leu  Thr  Gln  Leu  Thr  Val  Gln  Leu
     1040                     1045                    1050

Gln  His  Asn  Phe  Gln  Ala  Ile  Ser  Ser  Ser  Ile  Asp  Asp  Ile  Tyr
     1055                     1060                    1065

Ser  Arg  Leu  Asp  Ile  Leu  Ser  Ala  Asp  Val  Gln  Val  Asp  Arg  Leu
     1070                     1075                    1080

Ile  Thr  Gly  Arg  Leu  Ser  Ala  Leu  Asn  Ala  Phe  Val  Ala  Gln  Thr
     1085                     1090                    1095

Leu  Thr  Lys  Tyr  Thr  Glu  Val  Gln  Ala  Ser  Arg  Lys  Leu  Ala  Gln
     1100                     1105                    1110

Gln  Lys  Val  Asn  Glu  Cys  Val  Lys  Ser  Gln  Ser  Gln  Arg  Tyr  Gly
     1115                     1120                    1125

Phe  Cys  Gly  Gly  Asp  Gly  Glu  His  Ile  Phe  Ser  Leu  Val  Gln  Ala
     1130                     1135                    1140

Ala  Pro  Gln  Gly  Leu  Leu  Phe  Leu  His  Thr  Val  Leu  Val  Pro  Gly
     1145                     1150                    1155

Asp  Phe  Ile  Asp  Val  Ile  Ala  Ile  Ala  Gly  Leu  Cys  Val  Asn  Asp
     1160                     1165                    1170

Glu  Ile  Ala  Leu  Thr  Leu  Arg  Glu  Pro  Gly  Leu  Val  Leu  Phe  Thr
     1175                     1180                    1185

His  Glu  Leu  Gln  Asn  His  Thr  Ala  Thr  Glu  Tyr  Phe  Val  Ser  Ser
     1190                     1195                    1200

Arg  Arg  Met  Phe  Glu  Pro  Arg  Lys  Pro  Thr  Val  Ser  Asp  Phe  Val
     1205                     1210                    1215

Gln  Ile  Glu  Ser  Cys  Val  Val  Thr  Tyr  Val  Asn  Leu  Thr  Arg  Asp
     1220                     1225                    1230

Gln  Leu  Pro  Asp  Val  Ile  Pro  Asp  Tyr  Ile  Asp  Val  Asn  Lys  Thr
     1235                     1240                    1245

Leu  Asp  Glu  Ile  Leu  Ala  Ser  Leu  Pro  Asn  Arg  Thr  Gly  Pro  Ser
     1250                     1255                    1260

Leu  Pro  Leu  Asp  Val  Phe  Asn  Ala  Thr  Tyr  Leu  Asn  Leu  Thr  Gly
     1265                     1270                    1275

Glu  Ile  Ala  Asp  Leu  Glu  Gln  Arg  Ser  Glu  Ser  Leu  Arg  Asn  Thr
     1280                     1285                    1290

Thr  Glu  Glu  Leu  Gln  Ser  Leu  Ile  Tyr  Asn  Ile  Asn  Asn  Thr  Leu
     1295                     1300                    1305

Val  Asp  Leu  Glu  Trp  Leu  Asn  Arg  Val  Glu  Thr  Tyr  Ile  Lys  Trp
     1310                     1315                    1320

Pro  Trp  Trp  Val  Trp  Leu  Ile  Val  Phe  Ile  Val  Leu  Ile  Phe  Val
     1325                     1330                    1335

Val  Ser  Leu  Leu  Val  Phe  Cys  Cys  Ile  Ser  Thr  Gly  Cys  Cys  Gly
     1340                     1345                    1350

Cys  Cys  Gly  Cys  Cys  Cys  Ala  Cys  Phe  Ser  Gly  Cys  Cys  Arg  Gly
     1355                     1360                    1365

Pro  Arg  Leu  Gln  Pro  Tyr  Glu  Val  Phe  Glu  Lys  Val  His  Val  Gln
     1370                     1375                    1380

<210> SEQ ID NO 11
<211> LENGTH: 1383
<212> TYPE: PRT
<213> ORGANISM: porcine epidemic diarrhea virus

<400> SEQUENCE: 11
```

```
Met Lys Ser Leu Asn Tyr Phe Trp Leu Phe Leu Pro Val Leu Ser Thr
  1               5                  10                  15

Leu Ser Leu Pro Gln Asp Val Thr Arg Cys Gln Ser Thr Ile Asn Phe
                 20                  25                  30

Arg Arg Phe Phe Ser Lys Phe Asn Val Gln Ala Pro Ala Val Val Val
             35                  40                  45

Leu Gly Gly Tyr Leu Pro Ser Met Asn Ser Ser Trp Tyr Cys Gly
 50                  55                  60

Thr Gly Leu Glu Thr Ala Ser Gly Val His Gly Ile Phe Leu Ser Tyr
 65                  70                  75                  80

Ile Asp Ala Gly Gln Gly Phe Glu Ile Gly Ile Ser Gln Glu Pro Phe
                 85                  90                  95

Asp Pro Ser Gly Tyr Gln Leu Tyr Leu His Lys Ala Thr Asn Gly Asn
                100                 105                 110

His Asn Ala Ile Ala Arg Leu Arg Ile Cys Gln Phe Pro Asn Asn Lys
            115                 120                 125

Thr Leu Gly Pro Thr Val Asn Asp Val Thr Thr Gly Arg Asn Cys Leu
        130                 135                 140

Phe Asn Lys Ala Ile Pro Ala Tyr Met Gln Asp Gly Lys Asn Ile Val
145                 150                 155                 160

Val Gly Ile Thr Trp Asp Asn Asp Arg Val Thr Val Phe Ala Asp Lys
                165                 170                 175

Ile Tyr His Phe Tyr Leu Lys Asn Asp Trp Ser Arg Val Ala Thr Arg
                180                 185                 190

Cys Tyr Asn Lys Arg Ser Cys Ala Met Gln Tyr Val Tyr Thr Pro Thr
            195                 200                 205

Tyr Tyr Met Leu Asn Val Thr Ser Ala Gly Glu Asp Gly Ile Tyr Tyr
        210                 215                 220

Glu Pro Cys Thr Ala Asn Cys Ser Gly Tyr Ala Val Asn Val Phe Ala
225                 230                 235                 240

Thr Asp Ser Asn Gly His Ile Pro Glu Gly Phe Ser Phe Asn Asn Trp
                245                 250                 255

Phe Leu Leu Ser Asn Asp Ser Thr Leu Leu His Gly Lys Val Val Ser
            260                 265                 270

Asn Gln Pro Leu Leu Val Asn Cys Leu Leu Ala Ile Pro Lys Ile Tyr
        275                 280                 285

Gly Leu Gly Gln Phe Phe Ser Phe Asn Gln Thr Met Asp Gly Val Cys
290                 295                 300

Asn Gly Ala Ala Ala Gln Arg Ala Pro Glu Ala Leu Arg Phe Asn Ile
305                 310                 315                 320

Asn Asp Thr Ser Val Ile Leu Ala Glu Gly Ser Ile Val Leu His Thr
                325                 330                 335

Ala Leu Gly Thr Asn Leu Ser Phe Val Cys Ser Asn Ser Ser Asp Pro
            340                 345                 350

His Leu Ala Thr Phe Thr Ile Pro Leu Gly Ala Thr Gln Val Pro Tyr
        355                 360                 365

Tyr Cys Phe Leu Lys Val Asp Thr Tyr Asn Ser Asn Val Tyr Lys Phe
370                 375                 380

Leu Ala Val Leu Pro Pro Thr Val Arg Glu Ile Val Ile Thr Lys Tyr
385                 390                 395                 400

Gly Asp Val Tyr Val Asn Gly Phe Gly Tyr Leu His Leu Gly Leu Leu
                405                 410                 415
```

-continued

Asp Ala Val Thr Ile Asn Phe Thr Gly His Thr Asp Asp Val
            420                 425                 430

Ser Gly Phe Trp Thr Ile Ala Ser Thr Asn Phe Val Asp Ala Leu Ile
        435                 440                 445

Glu Val Gln Gly Thr Ala Ile Gln Arg Ile Leu Tyr Cys Asp Asp Pro
    450                 455                 460

Val Ser Gln Leu Lys Cys Ser Gln Val Ala Phe Asp Leu Asp Asp Gly
465                 470                 475                 480

Phe Tyr Pro Ile Ser Ser Arg Asn Leu Leu Ser His Glu Gln Pro Ile
            485                 490                 495

Ser Phe Val Thr Leu Pro Ser Phe Asn Asp His Ser Phe Val Asn Ile
            500                 505                 510

Thr Val Ser Ala Ser Phe Gly Gly His Ser Gly Ala Asn Leu Ile Ala
        515                 520                 525

Ser Asp Thr Thr Ile Asn Gly Phe Ser Ser Phe Cys Val Asp Thr Arg
        530                 535                 540

Gln Phe Thr Ile Ser Leu Phe Tyr Asn Val Thr Asn Ser Tyr Gly Tyr
545                 550                 555                 560

Val Ser Lys Ser Gln Asp Ser Asn Cys Pro Phe Thr Leu Gln Ser Val
            565                 570                 575

Asn Asp Tyr Leu Ser Phe Ser Lys Phe Cys Val Ser Thr Ser Leu Leu
            580                 585                 590

Ala Ser Ala Cys Thr Ile Asp Leu Phe Gly Tyr Pro Glu Phe Gly Ser
        595                 600                 605

Gly Val Lys Phe Thr Ser Leu Tyr Phe Gln Phe Thr Glu Gly Glu Leu
    610                 615                 620

Ile Thr Gly Thr Pro Lys Pro Leu Glu Gly Val Thr Asp Val Ser Phe
625                 630                 635                 640

Met Thr Leu Asp Val Cys Thr Lys Tyr Thr Ile Tyr Gly Phe Lys Gly
            645                 650                 655

Glu Gly Ile Ile Thr Leu Thr Asn Ser Ser Phe Leu Ala Gly Val Tyr
            660                 665                 670

Tyr Thr Ser Asp Ser Gly Gln Leu Leu Ala Phe Lys Asn Val Thr Ser
        675                 680                 685

Gly Ala Val Tyr Ser Val Thr Pro Cys Ser Phe Ser Glu Gln Ala Ala
    690                 695                 700

Tyr Val Asp Asp Asp Ile Val Gly Val Ile Ser Ser Leu Ser Ser Ser
705                 710                 715                 720

Thr Phe Asn Ser Thr Arg Glu Leu Pro Gly Phe Phe Tyr His Ser Asn
            725                 730                 735

Asp Gly Ser Asn Cys Thr Glu Pro Val Leu Val Tyr Ser Asn Ile Gly
            740                 745                 750

Val Cys Lys Ser Gly Ser Ile Gly Tyr Val Pro Ser Gln Ser Gly Gln
        755                 760                 765

Val Lys Ile Ala Pro Thr Val Thr Gly Asn Ile Ser Ile Pro Thr Asn
    770                 775                 780

Phe Ser Met Ser Ile Arg Thr Glu Tyr Leu Gln Leu Tyr Asn Thr Pro
785                 790                 795                 800

Val Ser Val Asp Cys Ala Thr Tyr Val Cys Asn Gly Asn Ser Arg Cys
            805                 810                 815

Lys Gln Leu Leu Thr Gln Tyr Thr Ala Ala Cys Lys Thr Ile Glu Ser
            820                 825                 830

Ala Leu Gln Leu Ser Ala Arg Leu Glu Ser Val Glu Val Asn Ser Met

-continued

```
            835                 840                 845
Leu Thr Ile Ser Glu Glu Ala Leu Gln Leu Ala Thr Ile Ser Ser Phe
    850                 855                 860
Asn Gly Asp Gly Tyr Asn Phe Thr Asn Val Leu Gly Val Ser Val Tyr
865                 870                 875                 880
Asp Pro Ala Ser Gly Arg Val Val Gln Lys Arg Ser Phe Ile Glu Asp
                885                 890                 895
Ala Ala Phe Asn Lys Val Val Thr Asn Gly Leu Gly Thr Val Asp Glu
            900                 905                 910
Asp Tyr Lys Arg Cys Ser Asn Gly Arg Ser Val Ala Asp Leu Val Cys
                915                 920                 925
Ala Gln Tyr Tyr Ser Gly Val Met Val Leu Pro Gly Val Val Asp Ala
            930                 935                 940
Glu Lys Leu His Met Tyr Ser Ala Ser Leu Ile Gly Gly Met Val Leu
945                 950                 955                 960
Gly Gly Phe Thr Ser Ala Ala Ala Leu Pro Phe Ser Tyr Ala Val Gln
                965                 970                 975
Ala Arg Leu Asn Tyr Leu Ala Leu Gln Thr Asp Val Leu Gln Arg Asn
            980                 985                 990
Gln Gln Leu Leu Ala Glu Ser Phe  Asn Ser Ala Ile Gly  Asn Ile Thr
                995                 1000                1005
Ser Ala  Phe Glu Ser Val Lys  Glu Ala Ile Ser Gln  Thr Ser Lys
        1010                1015                1020
Gly Leu  Asn Thr Val Ala His  Ala Leu Thr Lys Val  Gln Glu Val
        1025                1030                1035
Val Asn  Ser Gln Gly Ala Ala  Leu Thr Gln Leu Thr  Val Gln Leu
        1040                1045                1050
Gln His  Asn Phe Gln Ala Ile  Ser Ser Ser Ile Asp  Asp Ile Tyr
        1055                1060                1065
Ser Arg  Leu Asp Ile Leu Ser  Ala Asp Val Gln Val  Asp Arg Leu
        1070                1075                1080
Ile Thr  Gly Arg Leu Ser Ala  Leu Asn Ala Phe Val  Ala Gln Thr
        1085                1090                1095
Leu Thr Lys Tyr Thr Glu Val  Gln Ala Ser Arg Lys  Leu Ala Gln
        1100                1105                1110
Gln Lys  Val Asn Glu Cys Val  Lys Ser Gln Ser Gln  Arg Tyr Gly
        1115                1120                1125
Phe Cys  Gly Gly Asp Gly Glu  His Ile Phe Ser Leu  Val Gln Ala
        1130                1135                1140
Ala Pro  Gln Gly Leu Leu Phe  Leu His Thr Val Leu  Val Pro Gly
        1145                1150                1155
Asp Phe  Ile Asp Val Ile Ala  Ile Ala Gly Leu Cys  Val Asn Asp
        1160                1165                1170
Glu Ile  Ala Leu Thr Leu Arg  Glu Pro Gly Leu Val  Leu Phe Thr
        1175                1180                1185
His Glu  Leu Gln Asn His Thr  Ala Thr Glu Tyr Phe  Val Ser Ser
        1190                1195                1200
Arg Arg  Met Phe Glu Pro Arg  Lys Pro Thr Val Ser  Asp Phe Val
        1205                1210                1215
Gln Ile  Glu Ser Cys Val Val  Thr Tyr Val Asn Leu  Thr Arg Asp
        1220                1225                1230
Gln Leu  Pro Asp Val Ile Pro  Asp Tyr Ile Asp Val  Asn Lys Thr
        1235                1240                1245
```

```
Leu Asp Glu Ile Leu Ala Ser Leu Pro Asn Arg Thr Gly Pro Ser
    1250                1255                1260

Leu Pro Leu Asp Val Phe Asn Ala Thr Tyr Leu Asn Leu Thr Gly
    1265                1270                1275

Glu Ile Ala Asp Leu Glu Gln Arg Ser Glu Ser Leu Arg Asn Thr
    1280                1285                1290

Thr Glu Glu Leu Gln Ser Leu Ile Tyr Asn Ile Asn Asn Thr Leu
    1295                1300                1305

Val Asp Leu Glu Trp Leu Asn Arg Val Glu Thr Tyr Ile Lys Trp
    1310                1315                1320

Pro Trp Trp Val Trp Leu Ile Val Phe Ile Val Leu Ile Phe Val
    1325                1330                1335

Val Ser Leu Leu Val Phe Cys Cys Ile Ser Thr Gly Cys Cys Gly
    1340                1345                1350

Cys Cys Gly Cys Cys Cys Ala Cys Phe Ser Gly Cys Cys Arg Gly
    1355                1360                1365

Pro Arg Leu Gln Pro Tyr Glu Val Phe Glu Lys Val His Val Gln
    1370                1375                1380
```

<210> SEQ ID NO 12
<211> LENGTH: 1383
<212> TYPE: PRT
<213> ORGANISM: porcine epidemic diarrhea virus

<400> SEQUENCE: 12

```
Met Lys Ser Leu Asn Tyr Phe Trp Leu Phe Leu Pro Val Leu Ser Thr
1               5                   10                  15

Leu Ser Leu Pro Gln Asp Val Thr Arg Cys Gln Ser Thr Ile Asn Phe
                20                  25                  30

Arg Arg Phe Phe Ser Lys Phe Asn Val Gln Ala Pro Ala Val Val Val
            35                  40                  45

Leu Gly Gly Tyr Leu Pro Ser Met Asn Ser Ser Trp Tyr Cys Gly
    50                  55                  60

Thr Gly Leu Glu Thr Ala Ser Gly Val His Gly Ile Phe Leu Ser Tyr
65                  70                  75                  80

Ile Asp Ala Gly Gln Gly Phe Glu Ile Gly Ile Ser Gln Glu Pro Phe
                85                  90                  95

Asp Pro Ser Gly Tyr Gln Leu Tyr Leu His Lys Ala Thr Asn Gly Asn
            100                 105                 110

His Asn Ala Ile Ala Arg Leu Arg Ile Cys Gln Phe Pro Asn Asn Lys
        115                 120                 125

Thr Leu Gly Pro Thr Val Asn Asp Val Thr Thr Gly Arg Asn Cys Leu
    130                 135                 140

Phe Asn Lys Ala Ile Pro Ala Tyr Met Gln Asp Gly Lys Asn Ile Val
145                 150                 155                 160

Val Gly Ile Thr Trp Asp Asn Asp Arg Val Thr Val Phe Ala Asp Lys
                165                 170                 175

Ile Tyr His Phe Tyr Leu Lys Asn Asp Trp Ser Arg Val Ala Thr Arg
            180                 185                 190

Cys Tyr Asn Lys Arg Ser Cys Ala Met Gln Tyr Val Tyr Thr Pro Thr
        195                 200                 205

Tyr Tyr Met Leu Asn Val Thr Ser Ala Gly Glu Asp Gly Ile Tyr Tyr
    210                 215                 220

Glu Pro Cys Thr Ala Asn Cys Ser Gly Tyr Ala Val Asn Val Phe Ala
```

```
                    225                 230                 235                 240

Thr Asp Ser Asn Gly His Ile Pro Glu Gly Phe Ser Phe Asn Asn Trp
                            245                 250                 255

Phe Leu Leu Ser Asn Asp Ser Thr Leu Leu His Gly Lys Val Val Ser
                            260                 265                 270

Asn Gln Pro Leu Leu Val Asn Cys Leu Leu Ala Ile Pro Lys Ile Tyr
                        275                 280                 285

Gly Leu Gly Gln Phe Phe Ser Phe Asn Gln Thr Met Asp Gly Val Cys
                        290                 295                 300

Asn Gly Ala Ala Ala Gln Arg Ala Pro Glu Ala Leu Arg Phe Asn Ile
            305                 310                 315                 320

Asn Asp Thr Ser Val Ile Leu Ala Glu Gly Ser Ile Val Leu His Thr
                            325                 330                 335

Ala Leu Gly Thr Asn Leu Ser Phe Val Cys Ser Asn Ser Ser Asp Pro
                        340                 345                 350

His Leu Ala Thr Phe Thr Ile Pro Leu Gly Ala Thr Gln Val Pro Tyr
                        355                 360                 365

Tyr Cys Phe Leu Lys Val Asp Thr Tyr Asn Ser Asn Val Tyr Lys Phe
                    370                 375                 380

Leu Ala Val Leu Pro Pro Thr Val Arg Glu Ile Val Ile Thr Lys Tyr
            385                 390                 395                 400

Gly Asp Val Tyr Val Asn Gly Phe Gly Tyr Leu His Leu Gly Leu Leu
                            405                 410                 415

Asp Ala Val Thr Ile Asn Phe Thr Gly His Gly Thr Asp Asp Asp Val
                        420                 425                 430

Ser Gly Phe Trp Thr Ile Ala Ser Thr Asn Phe Val Asp Ala Leu Ile
                    435                 440                 445

Glu Val Gln Gly Thr Ala Ile Gln Arg Ile Leu Tyr Cys Asp Asp Pro
                450                 455                 460

Val Ser Gln Leu Lys Cys Ser Gln Val Ala Phe Asp Leu Asp Asp Gly
            465                 470                 475                 480

Phe Tyr Pro Ile Ser Ser Arg Asn Leu Leu Ser His Glu Gln Pro Ile
                        485                 490                 495

Ser Phe Val Thr Leu Pro Ser Phe Asn Asp His Ser Phe Val Asn Ile
                        500                 505                 510

Thr Val Ser Ala Ser Phe Gly Gly His Ser Gly Ala Asn Leu Ile Ala
                    515                 520                 525

Ser Asp Thr Thr Ile Asn Gly Phe Ser Ser Phe Cys Val Asp Thr Arg
            530                 535                 540

Gln Phe Thr Ile Ser Leu Phe Tyr Asn Val Thr Asn Ser Tyr Gly Tyr
            545                 550                 555                 560

Val Ser Lys Ser Gln Asp Ser Asn Cys Pro Phe Thr Leu Gln Ser Val
                        565                 570                 575

Asn Asp Tyr Leu Ser Phe Ser Lys Phe Cys Val Ser Thr Ser Leu Leu
                        580                 585                 590

Ala Ser Ala Cys Thr Ile Asp Leu Phe Gly Tyr Pro Glu Phe Gly Ser
                    595                 600                 605

Gly Val Lys Phe Thr Ser Leu Tyr Phe Gln Phe Thr Glu Gly Glu Leu
                610                 615                 620

Ile Thr Gly Thr Pro Lys Pro Leu Glu Gly Val Thr Asp Val Ser Phe
            625                 630                 635                 640

Met Thr Leu Asp Val Cys Thr Lys Tyr Thr Ile Tyr Gly Phe Lys Gly
                        645                 650                 655
```

-continued

Glu Gly Ile Ile Thr Leu Thr Asn Ser Ser Phe Leu Ala Gly Val Tyr
            660                 665                 670

Tyr Thr Ser Asp Ser Gly Gln Leu Leu Ala Phe Lys Asn Val Thr Ser
        675                 680                 685

Gly Ala Val Tyr Ser Val Thr Pro Cys Ser Phe Ser Glu Gln Ala Ala
690                 695                 700

Tyr Val Asp Asp Ile Val Gly Val Ile Ser Ser Leu Ser Ser Ser
705                 710                 715                 720

Thr Phe Asn Ser Thr Arg Glu Leu Pro Gly Phe Phe Tyr His Ser Asn
                725                 730                 735

Asp Gly Ser Asn Cys Thr Glu Pro Val Leu Val Tyr Ser Asn Ile Gly
            740                 745                 750

Val Cys Lys Ser Gly Ser Ile Gly Tyr Val Pro Ser Gln Ser Gly Gln
        755                 760                 765

Val Lys Ile Ala Pro Thr Val Thr Gly Asn Ile Ser Ile Pro Thr Asn
770                 775                 780

Phe Ser Met Ser Ile Arg Thr Glu Tyr Leu Gln Leu Tyr Asn Thr Pro
785                 790                 795                 800

Val Ser Val Asp Cys Ala Thr Tyr Val Cys Asn Gly Asn Ser Arg Cys
                805                 810                 815

Lys Gln Leu Leu Thr Gln Tyr Thr Ala Ala Cys Lys Thr Ile Glu Ser
            820                 825                 830

Ala Leu Gln Leu Ser Ala Arg Leu Glu Ser Val Glu Val Asn Ser Met
        835                 840                 845

Leu Thr Ile Ser Glu Glu Ala Leu Gln Leu Ala Thr Ile Ser Ser Phe
    850                 855                 860

Asn Gly Asp Gly Tyr Asn Phe Thr Asn Val Leu Gly Val Ser Val Tyr
865                 870                 875                 880

Asp Pro Ala Ser Gly Arg Val Val Gln Lys Arg Ser Phe Ile Glu Asp
                885                 890                 895

Ala Leu Phe Asn Lys Val Val Thr Asn Gly Leu Gly Thr Val Asp Glu
            900                 905                 910

Asp Tyr Lys Arg Cys Ser Asn Gly Arg Ser Val Ala Asp Leu Val Cys
        915                 920                 925

Ala Gln Tyr Tyr Ser Gly Val Met Val Leu Pro Gly Val Val Asp Ala
    930                 935                 940

Glu Lys Leu His Met Tyr Ser Ala Ser Leu Ile Gly Gly Met Val Leu
945                 950                 955                 960

Gly Gly Phe Thr Ser Ala Ala Ala Leu Pro Phe Ser Tyr Ala Val Gln
                965                 970                 975

Ala Arg Leu Asn Tyr Leu Ala Leu Gln Thr Asp Val Leu Gln Arg Asn
            980                 985                 990

Gln Gln Leu Leu Ala Glu Ser Phe Asn Ser Ala Ile Gly Asn Ile Thr
        995                 1000                1005

Ser Ala Phe Glu Ser Val Lys Glu Ala Ile Ser Gln Thr Ser Lys
    1010                1015                1020

Gly Leu Asn Thr Val Ala His Ala Leu Thr Lys Val Gln Glu Val
    1025                1030                1035

Val Asn Ser Gln Gly Ala Ala Leu Thr Gln Leu Thr Val Gln Leu
    1040                1045                1050

Gln His Asn Phe Gln Ala Ile Ser Ser Ser Ile Asp Asp Ile Tyr
    1055                1060                1065

```
Ser Arg Leu Asp Ile Leu Ser Ala Asp Val Gln Val Asp Arg Leu
    1070                1075                1080

Ile Thr Gly Arg Leu Ser Ala Leu Asn Ala Phe Val Ala Gln Thr
    1085                1090                1095

Leu Thr Lys Tyr Thr Glu Val Gln Ala Ser Arg Lys Leu Ala Gln
    1100                1105                1110

Gln Lys Val Asn Glu Cys Val Lys Ser Gln Ser Gln Arg Tyr Gly
    1115                1120                1125

Phe Cys Gly Gly Asp Gly Glu His Ile Phe Ser Leu Val Gln Ala
    1130                1135                1140

Ala Pro Gln Gly Leu Leu Phe Leu His Thr Val Leu Val Pro Gly
    1145                1150                1155

Asp Phe Ile Asp Val Ile Ala Ile Ala Gly Leu Cys Val Asn Asp
    1160                1165                1170

Glu Ile Ala Leu Thr Leu Arg Glu Pro Gly Leu Val Leu Phe Thr
    1175                1180                1185

His Glu Leu Gln Asn His Thr Ala Thr Glu Tyr Phe Val Ser Ser
    1190                1195                1200

Arg Arg Met Phe Glu Pro Arg Lys Pro Thr Val Ser Asp Phe Val
    1205                1210                1215

Gln Ile Glu Ser Cys Val Val Thr Tyr Val Asn Leu Thr Arg Asp
    1220                1225                1230

Gln Leu Pro Asp Val Ile Pro Asp Tyr Ile Asp Val Asn Lys Thr
    1235                1240                1245

Leu Asp Glu Ile Leu Ala Ser Leu Pro Asn Arg Thr Gly Pro Ser
    1250                1255                1260

Leu Pro Leu Asp Val Phe Asn Ala Thr Tyr Leu Asn Leu Thr Gly
    1265                1270                1275

Glu Ile Ala Asp Leu Glu Gln Arg Ser Glu Ser Leu Arg Asn Thr
    1280                1285                1290

Thr Glu Glu Leu Gln Ser Leu Ile Tyr Asn Ile Asn Asn Thr Leu
    1295                1300                1305

Val Asp Leu Glu Trp Leu Asn Arg Val Glu Thr Tyr Ile Lys Trp
    1310                1315                1320

Pro Trp Trp Val Trp Leu Ile Val Phe Ile Val Leu Ile Phe Val
    1325                1330                1335

Val Ser Leu Leu Val Phe Cys Cys Ile Ser Thr Gly Cys Cys Gly
    1340                1345                1350

Cys Cys Gly Cys Cys Ala Cys Phe Ser Gly Cys Cys Arg Gly
    1355                1360                1365

Pro Arg Leu Gln Pro Ala Glu Val Phe Glu Lys Val Arg Val Gln
    1370                1375                1380

<210> SEQ ID NO 13
<211> LENGTH: 1383
<212> TYPE: PRT
<213> ORGANISM: porcine epidemic diarrhea virus

<400> SEQUENCE: 13

Met Lys Ser Leu Asn Tyr Phe Trp Leu Phe Leu Pro Val Leu Ser Thr
1               5                   10                  15

Leu Ser Leu Pro Gln Asp Val Thr Arg Cys Gln Ser Thr Ile Asn Phe
                20                  25                  30

Arg Arg Phe Phe Ser Lys Phe Asn Val Gln Ala Pro Ala Val Val Val
            35                  40                  45
```

-continued

```
Leu Gly Gly Tyr Leu Pro Ser Met Asn Ser Ser Trp Tyr Cys Gly
     50                  55                  60
Thr Gly Leu Glu Thr Ala Ser Gly Val His Gly Ile Phe Leu Ser Tyr
 65                  70                  75                  80
Ile Asp Ala Gly Gln Gly Phe Glu Ile Gly Ile Ser Gln Glu Pro Phe
                 85                  90                  95
Asp Pro Ser Gly Tyr Gln Leu Tyr Leu His Lys Ala Thr Asn Gly Asn
                100                 105                 110
His Asn Ala Ile Ala Arg Leu Arg Ile Cys Gln Phe Pro Asn Asn Lys
            115                 120                 125
Thr Leu Gly Pro Thr Val Asn Asp Val Thr Thr Gly Arg Asn Cys Leu
    130                 135                 140
Phe Asn Lys Ala Ile Pro Ala Tyr Met Gln Asp Gly Lys Asn Ile Val
145                 150                 155                 160
Val Gly Ile Thr Trp Asp Asn Asp Arg Val Thr Val Phe Ala Asp Lys
                165                 170                 175
Ile Tyr His Phe Tyr Leu Lys Asn Asp Trp Ser Arg Val Ala Thr Arg
            180                 185                 190
Cys Tyr Asn Lys Arg Ser Cys Ala Met Gln Tyr Val Tyr Thr Pro Thr
    195                 200                 205
Tyr Tyr Met Leu Asn Val Thr Ser Ala Gly Glu Asp Gly Ile Tyr Tyr
210                 215                 220
Glu Pro Cys Thr Ala Asn Cys Ser Gly Tyr Ala Val Asn Val Phe Ala
225                 230                 235                 240
Thr Asp Ser Asn Gly His Ile Pro Glu Gly Phe Ser Phe Asn Asn Trp
                245                 250                 255
Phe Leu Leu Ser Asn Asp Ser Thr Leu Leu His Gly Lys Val Val Ser
            260                 265                 270
Asn Gln Pro Leu Leu Val Asn Cys Leu Leu Ala Ile Pro Lys Ile Tyr
    275                 280                 285
Gly Leu Gly Gln Phe Phe Ser Phe Asn Gln Thr Met Asp Gly Val Cys
    290                 295                 300
Asn Gly Ala Ala Ala Gln Arg Ala Pro Glu Ala Leu Arg Phe Asn Ile
305                 310                 315                 320
Asn Asp Thr Ser Val Ile Leu Ala Glu Gly Ser Ile Val Leu His Thr
                325                 330                 335
Ala Leu Gly Thr Asn Leu Ser Phe Val Cys Ser Asn Ser Ser Asp Pro
            340                 345                 350
His Leu Ala Thr Phe Thr Ile Pro Leu Gly Ala Thr Gln Val Pro Tyr
    355                 360                 365
Tyr Cys Phe Leu Lys Val Asp Thr Tyr Asn Ser Asn Val Tyr Lys Phe
370                 375                 380
Leu Ala Val Leu Pro Pro Thr Val Arg Glu Ile Val Ile Thr Lys Tyr
385                 390                 395                 400
Gly Asp Val Tyr Val Asn Gly Phe Gly Tyr Leu His Leu Gly Leu Leu
                405                 410                 415
Asp Ala Val Thr Ile Asn Phe Thr Gly His Gly Thr Asp Asp Asp Val
            420                 425                 430
Ser Gly Phe Trp Thr Ile Ala Ser Thr Asn Phe Val Asp Ala Leu Ile
    435                 440                 445
Glu Val Gln Gly Thr Ala Ile Gln Arg Ile Leu Tyr Cys Asp Asp Pro
    450                 455                 460
```

```
Val Ser Gln Leu Lys Cys Ser Gln Val Ala Phe Asp Leu Asp Asp Gly
465                 470                 475                 480

Phe Tyr Pro Ile Ser Ser Arg Asn Leu Leu Ser His Glu Gln Pro Ile
            485                 490                 495

Ser Phe Val Thr Leu Pro Ser Phe Asn Asp His Ser Phe Val Asn Ile
                500                 505                 510

Thr Val Ser Ala Ser Phe Gly Gly His Ser Gly Ala Asn Leu Ile Ala
            515                 520                 525

Ser Asp Thr Thr Ile Asn Gly Phe Ser Ser Phe Cys Val Asp Thr Arg
530                 535                 540

Gln Phe Thr Ile Ser Leu Phe Tyr Asn Val Thr Asn Ser Tyr Gly Tyr
545                 550                 555                 560

Val Ser Lys Ser Gln Asp Ser Asn Cys Pro Phe Thr Leu Gln Ser Val
                565                 570                 575

Asn Asp Tyr Leu Ser Phe Ser Lys Phe Cys Val Ser Thr Ser Leu Leu
            580                 585                 590

Ala Ser Ala Cys Thr Ile Asp Leu Phe Gly Tyr Pro Glu Phe Gly Ser
            595                 600                 605

Gly Val Lys Phe Thr Ser Leu Tyr Phe Gln Phe Thr Glu Gly Glu Leu
    610                 615                 620

Ile Thr Gly Thr Pro Lys Pro Leu Glu Gly Val Thr Asp Val Ser Phe
625                 630                 635                 640

Met Thr Leu Asp Val Cys Thr Lys Tyr Thr Ile Tyr Gly Phe Lys Gly
                645                 650                 655

Glu Gly Ile Ile Thr Leu Thr Asn Ser Ser Phe Leu Ala Gly Val Tyr
            660                 665                 670

Tyr Thr Ser Asp Ser Gly Gln Leu Leu Ala Phe Lys Asn Val Thr Ser
            675                 680                 685

Gly Ala Val Tyr Ser Val Thr Pro Cys Ser Phe Ser Glu Gln Ala Ala
    690                 695                 700

Tyr Val Asp Asp Asp Ile Val Gly Val Ile Ser Ser Leu Ser Ser Ser
705                 710                 715                 720

Thr Phe Asn Ser Thr Arg Glu Leu Pro Gly Phe Phe Tyr His Ser Asn
                725                 730                 735

Asp Gly Ser Asn Cys Thr Glu Pro Val Leu Val Tyr Ser Asn Ile Gly
            740                 745                 750

Val Cys Lys Ser Gly Ser Ile Gly Tyr Val Pro Ser Gln Ser Gly Gln
            755                 760                 765

Val Lys Ile Ala Pro Thr Val Thr Gly Asn Ile Ser Ile Pro Thr Asn
    770                 775                 780

Phe Ser Met Ser Ile Arg Thr Glu Tyr Leu Gln Leu Tyr Asn Thr Pro
785                 790                 795                 800

Val Ser Val Asp Cys Ala Thr Tyr Val Cys Asn Gly Asn Ser Arg Cys
                805                 810                 815

Lys Gln Leu Leu Thr Gln Tyr Thr Ala Ala Cys Lys Thr Ile Glu Ser
            820                 825                 830

Ala Leu Gln Leu Ser Ala Arg Leu Glu Ser Val Glu Val Asn Ser Met
            835                 840                 845

Leu Thr Ile Ser Glu Glu Ala Leu Gln Leu Ala Thr Ile Ser Ser Phe
            850                 855                 860

Asn Gly Asp Gly Tyr Asn Phe Thr Asn Val Leu Gly Val Ser Val Tyr
865                 870                 875                 880

Asp Pro Ala Ser Gly Arg Val Val Gln Lys Arg Ser Phe Ile Glu Asp
```

```
                885                 890                 895
Leu Ala Phe Asn Lys Val Val Thr Asn Gly Leu Gly Thr Val Asp Glu
                900                 905                 910

Asp Tyr Lys Arg Cys Ser Asn Gly Arg Ser Val Ala Asp Leu Val Cys
                915                 920                 925

Ala Gln Tyr Tyr Ser Gly Val Met Val Leu Pro Gly Val Val Asp Ala
            930                 935                 940

Glu Lys Leu His Met Tyr Ser Ala Ser Leu Ile Gly Gly Met Val Leu
945                 950                 955                 960

Gly Gly Phe Thr Ser Ala Ala Ala Leu Pro Phe Ser Tyr Ala Val Gln
                    965                 970                 975

Ala Arg Leu Asn Tyr Leu Ala Leu Gln Thr Asp Val Leu Gln Arg Asn
                980                 985                 990

Gln Gln Leu Leu Ala Glu Ser Phe Asn Ser Ala Ile Gly Asn Ile Thr
                995                 1000                1005

Ser Ala Phe Glu Ser Val Lys Glu Ala Ile Ser Gln Thr Ser Lys
    1010                1015                1020

Gly Leu Asn Thr Val Ala His Ala Leu Thr Lys Val Gln Glu Val
    1025                1030                1035

Val Asn Ser Gln Gly Ala Ala Leu Thr Gln Leu Thr Val Gln Leu
    1040                1045                1050

Gln His Asn Phe Gln Ala Ile Ser Ser Ser Ile Asp Asp Ile Tyr
    1055                1060                1065

Ser Arg Leu Asp Ile Leu Ser Ala Asp Val Gln Val Asp Arg Leu
    1070                1075                1080

Ile Thr Gly Arg Leu Ser Ala Leu Asn Ala Phe Val Ala Gln Thr
    1085                1090                1095

Leu Thr Lys Tyr Thr Glu Val Gln Ala Ser Arg Lys Leu Ala Gln
    1100                1105                1110

Gln Lys Val Asn Glu Cys Val Lys Ser Gln Ser Gln Arg Tyr Gly
    1115                1120                1125

Phe Cys Gly Gly Asp Gly Glu His Ile Phe Ser Leu Val Gln Ala
    1130                1135                1140

Ala Pro Gln Gly Leu Leu Phe Leu His Thr Val Leu Val Pro Gly
    1145                1150                1155

Asp Phe Ile Asp Val Ile Ala Ile Ala Gly Leu Cys Val Asn Asp
    1160                1165                1170

Glu Ile Ala Leu Thr Leu Arg Glu Pro Gly Leu Val Leu Phe Thr
    1175                1180                1185

His Glu Leu Gln Asn His Thr Ala Thr Glu Tyr Phe Val Ser Ser
    1190                1195                1200

Arg Arg Met Phe Glu Pro Arg Lys Pro Thr Val Ser Asp Phe Val
    1205                1210                1215

Gln Ile Glu Ser Cys Val Val Thr Tyr Val Asn Leu Thr Arg Asp
    1220                1225                1230

Gln Leu Pro Asp Val Ile Pro Asp Tyr Ile Asp Val Asn Lys Thr
    1235                1240                1245

Leu Asp Glu Ile Leu Ala Ser Leu Pro Asn Arg Thr Gly Pro Ser
    1250                1255                1260

Leu Pro Leu Asp Val Phe Asn Ala Thr Tyr Leu Asn Leu Thr Gly
    1265                1270                1275

Glu Ile Ala Asp Leu Glu Gln Arg Ser Glu Ser Leu Arg Asn Thr
    1280                1285                1290
```

Thr Glu Glu Leu Gln Ser Leu Ile Tyr Asn Ile Asn Asn Thr Leu
       1295                1300                1305

Val Asp Leu Glu Trp Leu Asn Arg Val Glu Thr Tyr Ile Lys Trp
       1310                1315                1320

Pro Trp Trp Val Trp Leu Ile Val Phe Ile Val Leu Ile Phe Val
       1325                1330                1335

Val Ser Leu Leu Val Phe Cys Cys Ile Ser Thr Gly Cys Cys Gly
       1340                1345                1350

Cys Cys Gly Cys Cys Cys Ala Cys Phe Ser Gly Cys Cys Arg Gly
       1355                1360                1365

Pro Arg Leu Gln Pro Ala Glu Val Phe Glu Lys Val Arg Val Gln
       1370                1375                1380

<210> SEQ ID NO 14
<211> LENGTH: 1383
<212> TYPE: PRT
<213> ORGANISM: porcine epidemic diarrhea virus

<400> SEQUENCE: 14

Met Lys Ser Leu Asn Tyr Phe Trp Leu Phe Leu Pro Val Leu Ser Thr
 1               5                  10                  15

Leu Ser Leu Pro Gln Asp Val Thr Arg Cys Gln Ser Thr Ile Asn Phe
                20                  25                  30

Arg Arg Phe Phe Ser Lys Phe Asn Val Gln Ala Pro Ala Val Val Val
                35                  40                  45

Leu Gly Gly Tyr Leu Pro Ser Met Asn Ser Ser Trp Tyr Cys Gly
        50                  55                  60

Thr Gly Leu Glu Thr Ala Ser Gly Val His Gly Ile Phe Leu Ser Tyr
 65                  70                  75                  80

Ile Asp Ala Gly Gln Gly Phe Glu Ile Gly Ile Ser Gln Glu Pro Phe
                85                  90                  95

Asp Pro Ser Gly Tyr Gln Leu Tyr Leu His Lys Ala Thr Asn Gly Asn
                100                 105                 110

His Asn Ala Ile Ala Arg Leu Arg Ile Cys Gln Phe Pro Asn Asn Lys
                115                 120                 125

Thr Leu Gly Pro Thr Val Asn Asp Val Thr Thr Gly Arg Asn Cys Leu
        130                 135                 140

Phe Asn Lys Ala Ile Pro Ala Tyr Met Gln Asp Gly Lys Asn Ile Val
145                 150                 155                 160

Val Gly Ile Thr Trp Asp Asn Asp Arg Val Thr Val Phe Ala Asp Lys
                165                 170                 175

Ile Tyr His Phe Tyr Leu Lys Asn Asp Trp Ser Arg Val Ala Thr Arg
                180                 185                 190

Cys Tyr Asn Lys Arg Ser Cys Ala Met Gln Tyr Val Tyr Thr Pro Thr
                195                 200                 205

Tyr Tyr Met Leu Asn Val Thr Ser Ala Gly Glu Asp Gly Ile Tyr Tyr
        210                 215                 220

Glu Pro Cys Thr Ala Asn Cys Ser Gly Tyr Ala Val Asn Val Phe Ala
225                 230                 235                 240

Thr Asp Ser Asn Gly His Ile Pro Glu Gly Phe Ser Phe Asn Asn Trp
                245                 250                 255

Phe Leu Leu Ser Asn Asp Ser Thr Leu Leu His Gly Lys Val Val Ser
                260                 265                 270

Asn Gln Pro Leu Leu Val Asn Cys Leu Leu Ala Ile Pro Lys Ile Tyr

```
                275                 280                 285
Gly Leu Gly Gln Phe Phe Ser Phe Asn Gln Thr Met Asp Gly Val Cys
290                 295                 300
Asn Gly Ala Ala Ala Gln Arg Ala Pro Glu Ala Leu Arg Phe Asn Ile
305                 310                 315                 320
Asn Asp Thr Ser Val Ile Leu Ala Glu Gly Ser Ile Val Leu His Thr
                325                 330                 335
Ala Leu Gly Thr Asn Leu Ser Phe Val Cys Ser Asn Ser Ser Asp Pro
                340                 345                 350
His Leu Ala Thr Phe Thr Ile Pro Leu Gly Ala Thr Gln Val Pro Tyr
                355                 360                 365
Tyr Cys Phe Leu Lys Val Asp Thr Tyr Asn Ser Asn Val Tyr Lys Phe
370                 375                 380
Leu Ala Val Leu Pro Pro Thr Val Arg Glu Ile Val Ile Thr Lys Tyr
385                 390                 395                 400
Gly Asp Val Tyr Val Asn Gly Phe Gly Tyr Leu His Leu Gly Leu Leu
                405                 410                 415
Asp Ala Val Thr Ile Asn Phe Thr Gly His Gly Thr Asp Asp Asp Val
                420                 425                 430
Ser Gly Phe Trp Thr Ile Ala Ser Thr Asn Phe Val Asp Ala Leu Ile
                435                 440                 445
Glu Val Gln Gly Thr Ala Ile Gln Arg Ile Leu Tyr Cys Asp Asp Pro
450                 455                 460
Val Ser Gln Leu Lys Cys Ser Gln Val Ala Phe Asp Leu Asp Asp Gly
465                 470                 475                 480
Phe Tyr Pro Ile Ser Ser Arg Asn Leu Leu Ser His Glu Gln Pro Ile
                485                 490                 495
Ser Phe Val Thr Leu Pro Ser Phe Asn Asp His Ser Phe Val Asn Ile
                500                 505                 510
Thr Val Ser Ala Ser Phe Gly Gly His Ser Gly Ala Asn Leu Ile Ala
                515                 520                 525
Ser Asp Thr Thr Ile Asn Gly Phe Ser Ser Phe Cys Val Asp Thr Arg
530                 535                 540
Gln Phe Thr Ile Ser Leu Phe Tyr Asn Val Thr Asn Ser Tyr Gly Tyr
545                 550                 555                 560
Val Ser Lys Ser Gln Asp Ser Asn Cys Pro Phe Thr Leu Gln Ser Val
                565                 570                 575
Asn Asp Tyr Leu Ser Phe Ser Lys Phe Cys Val Ser Thr Ser Leu Leu
                580                 585                 590
Ala Ser Ala Cys Thr Ile Asp Leu Phe Gly Tyr Pro Glu Phe Gly Ser
                595                 600                 605
Gly Val Lys Phe Thr Ser Leu Tyr Phe Gln Phe Thr Glu Gly Glu Leu
610                 615                 620
Ile Thr Gly Thr Pro Lys Pro Leu Glu Gly Val Thr Asp Val Ser Phe
625                 630                 635                 640
Met Thr Leu Asp Val Cys Thr Lys Tyr Thr Ile Tyr Gly Phe Lys Gly
                645                 650                 655
Glu Gly Ile Ile Thr Leu Thr Asn Ser Ser Phe Leu Ala Gly Val Tyr
                660                 665                 670
Tyr Thr Ser Asp Ser Gly Gln Leu Leu Ala Phe Lys Asn Val Thr Ser
                675                 680                 685
Gly Ala Val Tyr Ser Val Thr Pro Cys Ser Phe Ser Glu Gln Ala Ala
690                 695                 700
```

-continued

Tyr Val Asp Asp Ile Val Gly Val Ile Ser Ser Leu Ser Ser
705                 710                 715                 720

Thr Phe Asn Ser Thr Arg Glu Leu Pro Gly Phe Tyr His Ser Asn
            725                 730                 735

Asp Gly Ser Asn Cys Thr Glu Pro Val Leu Val Tyr Ser Asn Ile Gly
            740                 745                 750

Val Cys Lys Ser Gly Ser Ile Gly Tyr Val Pro Ser Gln Ser Gly Gln
            755                 760                 765

Val Lys Ile Ala Pro Thr Val Thr Gly Asn Ile Ser Ile Pro Thr Asn
770                 775                 780

Phe Ser Met Ser Ile Arg Thr Glu Tyr Leu Gln Leu Tyr Asn Thr Pro
785                 790                 795                 800

Val Ser Val Asp Cys Ala Thr Tyr Val Cys Asn Gly Asn Ser Arg Cys
            805                 810                 815

Lys Gln Leu Leu Thr Gln Tyr Thr Ala Ala Cys Lys Thr Ile Glu Ser
            820                 825                 830

Ala Leu Gln Leu Ser Ala Arg Leu Glu Ser Val Glu Val Asn Ser Met
            835                 840                 845

Leu Thr Ile Ser Glu Glu Ala Leu Gln Leu Ala Thr Ile Ser Ser Phe
850                 855                 860

Asn Gly Asp Gly Tyr Asn Phe Thr Asn Val Leu Gly Val Ser Val Tyr
865                 870                 875                 880

Asp Pro Ala Ser Gly Arg Val Val Gln Lys Arg Ser Phe Ile Glu Asp
            885                 890                 895

Ala Ala Phe Asn Lys Val Val Thr Asn Gly Leu Gly Thr Val Asp Glu
            900                 905                 910

Asp Tyr Lys Arg Cys Ser Asn Gly Arg Ser Val Ala Asp Leu Val Cys
            915                 920                 925

Ala Gln Tyr Tyr Ser Gly Val Met Val Leu Pro Gly Val Val Asp Ala
930                 935                 940

Glu Lys Leu His Met Tyr Ser Ala Ser Leu Ile Gly Gly Met Val Leu
945                 950                 955                 960

Gly Gly Phe Thr Ser Ala Ala Ala Leu Pro Phe Ser Tyr Ala Val Gln
            965                 970                 975

Ala Arg Leu Asn Tyr Leu Ala Leu Gln Thr Asp Val Leu Gln Arg Asn
            980                 985                 990

Gln Gln Leu Leu Ala Glu Ser Phe Asn Ser Ala Ile Gly Asn Ile Thr
            995                 1000                1005

Ser Ala Phe Glu Ser Val Lys Glu Ala Ile Ser Gln Thr Ser Lys
    1010                1015                1020

Gly Leu Asn Thr Val Ala His Ala Leu Thr Lys Val Gln Glu Val
    1025                1030                1035

Val Asn Ser Gln Gly Ala Ala Leu Thr Gln Leu Thr Val Gln Leu
    1040                1045                1050

Gln His Asn Phe Gln Ala Ile Ser Ser Ser Ile Asp Asp Ile Tyr
    1055                1060                1065

Ser Arg Leu Asp Ile Leu Ser Ala Asp Val Gln Val Asp Arg Leu
    1070                1075                1080

Ile Thr Gly Arg Leu Ser Ala Leu Asn Ala Phe Val Ala Gln Thr
    1085                1090                1095

Leu Thr Lys Tyr Thr Glu Val Gln Ala Ser Arg Lys Leu Ala Gln
    1100                1105                1110

-continued

```
Gln Lys Val Asn Glu Cys Val Lys Ser Gln Ser Gln Arg Tyr Gly
    1115                1120                1125

Phe Cys Gly Gly Asp Gly Glu His Ile Phe Ser Leu Val Gln Ala
    1130                1135                1140

Ala Pro Gln Gly Leu Leu Phe Leu His Thr Val Leu Val Pro Gly
    1145                1150                1155

Asp Phe Ile Asp Val Ile Ala Ile Ala Gly Leu Cys Val Asn Asp
    1160                1165                1170

Glu Ile Ala Leu Thr Leu Arg Glu Pro Gly Leu Val Leu Phe Thr
    1175                1180                1185

His Glu Leu Gln Asn His Thr Ala Thr Glu Tyr Phe Val Ser Ser
    1190                1195                1200

Arg Arg Met Phe Glu Pro Arg Lys Pro Thr Val Ser Asp Phe Val
    1205                1210                1215

Gln Ile Glu Ser Cys Val Val Thr Tyr Val Asn Leu Thr Arg Asp
    1220                1225                1230

Gln Leu Pro Asp Val Ile Pro Asp Tyr Ile Asp Val Asn Lys Thr
    1235                1240                1245

Leu Asp Glu Ile Leu Ala Ser Leu Pro Asn Arg Thr Gly Pro Ser
    1250                1255                1260

Leu Pro Leu Asp Val Phe Asn Ala Thr Tyr Leu Asn Leu Thr Gly
    1265                1270                1275

Glu Ile Ala Asp Leu Glu Gln Arg Ser Glu Ser Leu Arg Asn Thr
    1280                1285                1290

Thr Glu Glu Leu Gln Ser Leu Ile Tyr Asn Ile Asn Asn Thr Leu
    1295                1300                1305

Val Asp Leu Glu Trp Leu Asn Arg Val Glu Thr Tyr Ile Lys Trp
    1310                1315                1320

Pro Trp Trp Val Trp Leu Ile Val Phe Ile Val Leu Ile Phe Val
    1325                1330                1335

Val Ser Leu Leu Val Phe Cys Cys Ile Ser Thr Gly Cys Cys Gly
    1340                1345                1350

Cys Cys Gly Cys Cys Ala Cys Phe Ser Gly Cys Cys Arg Gly
    1355                1360                1365

Pro Arg Leu Gln Pro Ala Glu Val Phe Glu Lys Val Arg Val Gln
    1370                1375                1380
```

<210> SEQ ID NO 15
<211> LENGTH: 1388
<212> TYPE: PRT
<213> ORGANISM: porcine epidemic diarrhea virus

<400> SEQUENCE: 15

```
Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Asn Thr Asn Phe
                20                  25                  30

Arg Arg Phe Phe Ser Lys Phe Asn Val Gln Ala Pro Ala Val Val Val
            35                  40                  45

Leu Gly Gly Tyr Leu Pro Ile Gly Glu Asn Gln Gly Val Asn Ser Thr
        50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95
```

```
Gln Glu Pro Phe Asp Pro Ser Gly Tyr Gln Leu Tyr Leu His Lys Ala
            100                 105                 110

Thr Asn Gly Asn Thr Asn Ala Thr Ala Arg Leu Arg Ile Cys Gln Phe
        115                 120                 125

Pro Ser Ile Lys Thr Leu Gly Pro Thr Ala Asn Asn Asp Val Thr Thr
    130                 135                 140

Gly Arg Asn Cys Leu Phe Asn Lys Ala Ile Pro Ala His Met Ser Glu
145                 150                 155                 160

His Ser Val Val Gly Ile Thr Trp Asp Asn Asp Arg Val Thr Val Phe
                165                 170                 175

Ser Asp Lys Ile Tyr Tyr Phe Tyr Phe Lys Asn Asp Trp Ser Arg Val
            180                 185                 190

Ala Thr Lys Cys Tyr Asn Ser Gly Cys Ala Met Gln Tyr Val Tyr
        195                 200                 205

Glu Pro Thr Tyr Tyr Met Leu Asn Val Thr Ser Ala Gly Glu Asp Gly
    210                 215                 220

Ile Ser Tyr Gln Pro Cys Thr Ala Asn Cys Ile Gly Tyr Ala Ala Asn
225                 230                 235                 240

Val Phe Ala Thr Glu Pro Asn Gly His Ile Pro Glu Gly Phe Ser Phe
                245                 250                 255

Asn Asn Trp Phe Leu Leu Ser Asn Asp Ser Thr Leu Val His Gly Lys
            260                 265                 270

Val Val Ser Asn Gln Pro Leu Leu Val Asn Cys Leu Leu Ala Ile Pro
        275                 280                 285

Lys Ile Tyr Gly Leu Gly Gln Phe Phe Ser Phe Asn Gln Thr Ile Asp
    290                 295                 300

Gly Val Cys Asn Gly Ala Ala Val Gln Arg Ala Pro Glu Ala Leu Arg
305                 310                 315                 320

Phe Asn Ile Asn Asp Thr Ser Val Ile Leu Ala Glu Gly Ser Ile Val
                325                 330                 335

Leu His Thr Ala Leu Gly Thr Asn Phe Ser Phe Val Cys Ser Asn Ser
            340                 345                 350

Ser Asn Pro His Leu Ala Thr Phe Ala Ile Pro Leu Gly Ala Thr Gln
        355                 360                 365

Val Pro Tyr Tyr Cys Phe Leu Lys Val Asp Thr Tyr Asn Ser Thr Val
    370                 375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
                405                 410                 415

Gly Leu Leu Asp Ala Val Thr Ile Asn Phe Thr Gly His Gly Thr Asp
            420                 425                 430

Asp Asp Val Ser Gly Phe Trp Thr Ile Ala Ser Thr Asn Phe Val Asp
        435                 440                 445

Ala Leu Ile Glu Val Gln Gly Thr Ala Ile Gln Arg Ile Leu Tyr Cys
    450                 455                 460

Asp Asp Pro Val Ser Gln Leu Lys Cys Ser Gln Val Ala Phe Asp Leu
465                 470                 475                 480

Asp Asp Gly Phe Tyr Pro Ile Ser Ser Arg Asn Leu Leu Ser His Glu
                485                 490                 495

Gln Pro Ile Ser Phe Val Thr Leu Pro Ser Phe Asn Asp His Ser Phe
            500                 505                 510
```

-continued

Val Asn Ile Thr Val Ser Ala Ser Phe Gly Gly His Ser Gly Ala Asn
515                 520                 525

Leu Ile Ala Ser Asp Thr Thr Ile Asn Gly Phe Ser Ser Phe Cys Val
530                 535                 540

Asp Thr Arg Gln Phe Thr Ile Ser Leu Phe Tyr Asn Val Thr Asn Ser
545                 550                 555                 560

Tyr Gly Tyr Val Ser Lys Ser Gln Asp Ser Asn Cys Pro Phe Thr Leu
                565                 570                 575

Gln Ser Val Asn Asp Tyr Leu Ser Phe Ser Lys Phe Cys Val Ser Thr
            580                 585                 590

Ser Leu Leu Ala Ser Ala Cys Thr Ile Asp Leu Phe Gly Tyr Pro Glu
        595                 600                 605

Phe Gly Ser Gly Val Lys Phe Thr Ser Leu Tyr Phe Gln Phe Thr Lys
    610                 615                 620

Gly Glu Leu Ile Thr Gly Thr Pro Lys Pro Leu Glu Gly Val Thr Asp
625                 630                 635                 640

Val Ser Phe Met Thr Leu Asp Val Cys Thr Lys Tyr Thr Ile Tyr Gly
                645                 650                 655

Phe Lys Gly Glu Gly Ile Ile Thr Leu Thr Asn Ser Ser Phe Leu Ala
            660                 665                 670

Gly Val Tyr Tyr Thr Ser Asp Ser Gly Gln Leu Leu Ala Phe Lys Asn
        675                 680                 685

Val Thr Ser Gly Ala Val Tyr Ser Val Thr Pro Cys Ser Phe Ser Glu
    690                 695                 700

Gln Ala Ala Tyr Val Asp Asp Ile Val Gly Val Ile Ser Ser Leu
705                 710                 715                 720

Ser Ser Ser Thr Phe Asn Ser Thr Arg Glu Leu Pro Gly Phe Phe Tyr
                725                 730                 735

His Ser Asn Asp Gly Ser Asn Cys Thr Glu Pro Val Leu Val Tyr Ser
            740                 745                 750

Asn Ile Gly Val Cys Lys Ser Gly Ser Ile Gly Tyr Val Pro Ser Gln
        755                 760                 765

Ser Gly Gln Val Lys Ile Ala Pro Thr Val Thr Gly Asn Ile Ser Ile
    770                 775                 780

Pro Thr Asn Phe Ser Met Ser Ile Arg Thr Glu Tyr Leu Gln Leu Tyr
785                 790                 795                 800

Asn Thr Pro Val Ser Val Asp Cys Ala Thr Tyr Val Cys Asn Gly Asn
                805                 810                 815

Ser Arg Cys Lys Gln Leu Leu Thr Gln Tyr Thr Ala Ala Cys Lys Thr
            820                 825                 830

Ile Glu Ser Ala Leu Gln Leu Ser Ala Arg Leu Glu Ser Val Glu Val
        835                 840                 845

Asn Ser Met Leu Thr Ile Ser Glu Glu Ala Leu Gln Leu Ala Thr Ile
    850                 855                 860

Ser Ser Phe Asn Gly Asp Gly Tyr Asn Phe Thr Asn Val Leu Gly Val
865                 870                 875                 880

Ser Val Tyr Asp Pro Ala Ser Gly Arg Val Val Gln Lys Arg Ser Phe
                885                 890                 895

Ile Glu Asp Ala Leu Phe Asn Lys Val Thr Asn Gly Leu Gly Thr
            900                 905                 910

Val Asp Glu Asp Tyr Lys Arg Cys Ser Asn Gly Arg Ser Val Ala Asp
    915                 920                 925

Leu Val Cys Ala Gln Tyr Tyr Ser Gly Val Met Val Leu Pro Gly Val

-continued

```
            930             935             940
Val Asp Ala Glu Lys Leu His Met Tyr Ser Ala Ser Leu Ile Gly Gly
945                 950                 955                 960

Met Val Leu Gly Gly Phe Thr Ser Ala Ala Ala Leu Pro Phe Ser Tyr
                965                 970                 975

Ala Val Gln Ala Arg Leu Asn Tyr Leu Ala Leu Gln Thr Asp Val Leu
            980                 985                 990

Gln Arg Asn Gln Gln Leu Leu Ala  Glu Ser Phe Asn Ser  Ala Ile Gly
        995                 1000                1005

Asn Ile  Thr Ser Ala Phe Glu  Ser Val Lys Glu Ala  Ile Ser Gln
    1010             1015             1020

Thr Ser  Lys Gly Leu Asn Thr  Val Ala His Ala Leu  Thr Lys Val
    1025             1030             1035

Gln Glu  Val Val Asn Ser Gln  Gly Ala Ala Leu Thr  Gln Leu Thr
    1040             1045             1050

Val Gln  Leu Gln His Asn Phe  Gln Ala Ile Ser Ser  Ser Ile Asp
    1055             1060             1065

Asp Ile  Tyr Ser Arg Leu Asp  Ile Leu Ser Ala Asp  Val Gln Val
    1070             1075             1080

Asp Arg  Leu Ile Thr Gly Arg  Leu Ser Ala Leu Asn  Ala Phe Val
    1085             1090             1095

Ala Gln  Thr Leu Thr Lys Tyr  Thr Glu Val Gln Ala  Ser Arg Lys
    1100             1105             1110

Leu Ala  Gln Gln Lys Val Asn  Glu Cys Val Lys Ser  Gln Ser Gln
    1115             1120             1125

Arg Tyr  Gly Phe Cys Gly Gly  Asp Gly Glu His Ile  Phe Ser Leu
    1130             1135             1140

Val Gln  Ala Ala Pro Gln Gly  Leu Leu Phe Leu His  Thr Val Leu
    1145             1150             1155

Val Pro  Ser Asp Phe Val Asp  Val Ile Ala Ile Ala  Gly Leu Cys
    1160             1165             1170

Val Asn  Asp Glu Ile Ala Leu  Thr Leu Arg Glu Pro  Gly Leu Val
    1175             1180             1185

Leu Phe  Thr His Glu Leu Gln  Asn His Thr Ala Thr  Glu Tyr Phe
    1190             1195             1200

Val Ser  Ser Arg Arg Met Phe  Glu Pro Arg Lys Pro  Thr Val Ser
    1205             1210             1215

Asp Phe  Val Gln Ile Glu Ser  Cys Val Val Thr Tyr  Val Asn Leu
    1220             1225             1230

Thr Arg  Asp Gln Leu Pro Asp  Val Ile Pro Asp Tyr  Ile Asp Val
    1235             1240             1245

Asn Lys  Thr Leu Asp Glu Ile  Leu Ala Ser Leu Pro  Asn Arg Thr
    1250             1255             1260

Gly Pro  Ser Leu Pro Leu Asp  Val Phe Asn Ala Thr  Tyr Leu Asn
    1265             1270             1275

Leu Thr  Gly Glu Ile Ala Asp  Leu Glu Gln Arg Ser  Glu Ser Leu
    1280             1285             1290

Arg Asn  Thr Thr Glu Glu Leu  Gln Ser Leu Ile Tyr  Asn Ile Asn
    1295             1300             1305

Asn Thr  Leu Val Asp Leu Glu  Trp Leu Asn Arg Val  Glu Thr Tyr
    1310             1315             1320

Ile Lys  Trp Pro Trp Trp Val  Trp Leu Ile Ile Phe  Ile Val Leu
    1325             1330             1335
```

-continued

```
Ile Phe Val Val Ser Leu Leu Val Phe Cys Cys Ile Ser Thr Gly
    1340                1345                1350

Cys Cys Gly Cys Cys Gly Cys Cys Ala Cys Phe Ser Gly Cys
    1355                1360                1365

Cys Arg Gly Pro Arg Leu Gln Pro Tyr Glu Val Phe Glu Lys Val
    1370                1375                1380

His Val Gln Cys Gly
    1385

<210> SEQ ID NO 16
<211> LENGTH: 1388
<212> TYPE: PRT
<213> ORGANISM: porcine epidemic diarrhea virus

<400> SEQUENCE: 16

Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Asn Thr Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ile Gly Glu Asn Gln Gly Val Asn Ser Thr
    50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
            100                 105                 110

Thr Asn Gly Asn Thr Asn Ala Thr Ala Arg Leu Arg Ile Cys Gln Phe
        115                 120                 125

Pro Ser Ile Lys Thr Leu Gly Pro Thr Ala Asn Asn Asp Val Thr Thr
    130                 135                 140

Gly Arg Asn Cys Leu Phe Asn Lys Ala Ile Pro Ala His Met Ser Glu
145                 150                 155                 160

His Ser Val Val Gly Ile Thr Trp Asp Asn Asp Arg Val Thr Val Phe
                165                 170                 175

Ser Asp Lys Ile Tyr Tyr Phe Tyr Phe Lys Asn Asp Trp Ser Arg Val
            180                 185                 190

Ala Thr Lys Cys Tyr Asn Ser Gly Gly Cys Ala Met Gln Tyr Val Tyr
        195                 200                 205

Glu Pro Thr Tyr Tyr Met Leu Asn Val Thr Ser Ala Gly Glu Asp Gly
    210                 215                 220

Ile Ser Tyr Gln Pro Cys Thr Ala Asn Cys Ile Gly Tyr Ala Ala Asn
225                 230                 235                 240

Val Phe Ala Thr Glu Pro Asn Gly His Ile Pro Glu Gly Phe Ser Phe
                245                 250                 255

Asn Asn Trp Phe Leu Leu Ser Asn Asp Ser Thr Leu Val His Gly Lys
            260                 265                 270

Val Val Ser Asn Gln Pro Leu Leu Val Asn Cys Leu Leu Ala Ile Pro
        275                 280                 285

Lys Ile Tyr Gly Leu Gly Gln Phe Phe Ser Phe Asn Gln Thr Ile Asp
    290                 295                 300

Gly Val Cys Asn Gly Ala Ala Val Gln Arg Ala Pro Glu Ala Leu Arg
```

```
                305                 310                 315                 320
        Phe Asn Ile Asn Asp Thr Ser Val Ile Leu Ala Glu Gly Ser Ile Val
                        325                 330                 335
        Leu His Thr Ala Leu Gly Thr Asn Phe Ser Phe Val Cys Ser Asn Ser
                        340                 345                 350
        Ser Asn Pro His Leu Ala Thr Phe Ala Ile Pro Leu Gly Ala Thr Gln
                        355                 360                 365
        Val Pro Tyr Tyr Cys Phe Leu Lys Val Asp Thr Tyr Asn Ser Thr Val
                370                 375                 380
        Tyr Lys Phe Leu Ala Val Leu Pro Pro Thr Val Arg Glu Ile Val Ile
        385                 390                 395                 400
        Thr Lys Tyr Gly Asp Val Tyr Val Asn Gly Phe Gly Tyr Leu His Leu
                        405                 410                 415
        Gly Leu Leu Asp Ala Val Thr Ile Asn Phe Thr Gly His Gly Thr Asp
                        420                 425                 430
        Asp Asp Val Ser Gly Phe Trp Thr Ile Ala Ser Thr Asn Phe Val Asp
                        435                 440                 445
        Ala Leu Ile Glu Val Gln Gly Thr Ala Ile Gln Arg Ile Leu Tyr Cys
                450                 455                 460
        Asp Asp Pro Val Ser Gln Leu Lys Cys Ser Gln Val Ala Phe Asp Leu
        465                 470                 475                 480
        Asp Asp Gly Phe Tyr Pro Ile Ser Ser Arg Asn Leu Leu Ser His Glu
                        485                 490                 495
        Gln Pro Ile Ser Phe Val Thr Leu Pro Ser Phe Asn Asp His Ser Phe
                        500                 505                 510
        Val Asn Ile Thr Val Ser Ala Ser Phe Gly Gly His Ser Gly Ala Asn
                        515                 520                 525
        Leu Ile Ala Ser Asp Thr Thr Ile Asn Gly Phe Ser Ser Phe Cys Val
                530                 535                 540
        Asp Thr Arg Gln Phe Thr Ile Ser Leu Phe Tyr Asn Val Thr Asn Ser
        545                 550                 555                 560
        Tyr Gly Tyr Val Ser Lys Ser Gln Asp Ser Asn Cys Pro Phe Thr Leu
                        565                 570                 575
        Gln Ser Val Asn Asp Tyr Leu Ser Phe Ser Lys Phe Cys Val Ser Thr
                        580                 585                 590
        Ser Leu Leu Ala Ser Ala Cys Thr Ile Asp Leu Phe Gly Tyr Pro Glu
                        595                 600                 605
        Phe Gly Ser Gly Val Lys Phe Thr Ser Leu Tyr Phe Gln Phe Thr Lys
                610                 615                 620
        Gly Glu Leu Ile Thr Gly Thr Pro Lys Pro Leu Glu Gly Val Thr Asp
        625                 630                 635                 640
        Val Ser Phe Met Thr Leu Asp Val Cys Thr Lys Tyr Thr Ile Tyr Gly
                        645                 650                 655
        Phe Lys Gly Glu Gly Ile Ile Thr Leu Thr Asn Ser Ser Phe Leu Ala
                        660                 665                 670
        Gly Val Tyr Tyr Thr Ser Asp Ser Gly Gln Leu Leu Ala Phe Lys Asn
                        675                 680                 685
        Val Thr Ser Gly Ala Val Tyr Ser Val Thr Pro Cys Ser Phe Ser Glu
                        690                 695                 700
        Gln Ala Ala Tyr Val Asp Asp Ile Val Gly Val Ile Ser Ser Leu
        705                 710                 715                 720
        Ser Ser Ser Thr Phe Asn Ser Thr Arg Glu Leu Pro Gly Phe Phe Tyr
                        725                 730                 735
```

-continued

His Ser Asn Asp Gly Ser Asn Cys Thr Glu Pro Val Leu Val Tyr Ser
                740                 745                 750

Asn Ile Gly Val Cys Lys Ser Gly Ser Ile Gly Tyr Val Pro Ser Gln
        755                 760                 765

Ser Gly Gln Val Lys Ile Ala Pro Thr Val Thr Gly Asn Ile Ser Ile
770                 775                 780

Pro Thr Asn Phe Ser Met Ser Ile Arg Thr Glu Tyr Leu Gln Leu Tyr
785                 790                 795                 800

Asn Thr Pro Val Ser Val Asp Cys Ala Thr Tyr Val Cys Asn Gly Asn
                805                 810                 815

Ser Arg Cys Lys Gln Leu Leu Thr Gln Tyr Thr Ala Ala Cys Lys Thr
                820                 825                 830

Ile Glu Ser Ala Leu Gln Leu Ser Ala Arg Leu Glu Ser Val Glu Val
                835                 840                 845

Asn Ser Met Leu Thr Ile Ser Glu Glu Ala Leu Gln Leu Ala Thr Ile
        850                 855                 860

Ser Ser Phe Asn Gly Asp Gly Tyr Asn Phe Thr Asn Val Leu Gly Val
865                 870                 875                 880

Ser Val Tyr Asp Pro Ala Ser Gly Arg Val Val Gln Lys Arg Ser Phe
                885                 890                 895

Ile Glu Asp Leu Ala Phe Asn Lys Val Val Thr Asn Gly Leu Gly Thr
                900                 905                 910

Val Asp Glu Asp Tyr Lys Arg Cys Ser Asn Gly Arg Ser Val Ala Asp
                915                 920                 925

Leu Val Cys Ala Gln Tyr Tyr Ser Gly Val Met Val Leu Pro Gly Val
                930                 935                 940

Val Asp Ala Glu Lys Leu His Met Tyr Ser Ala Ser Leu Ile Gly Gly
945                 950                 955                 960

Met Val Leu Gly Gly Phe Thr Ser Ala Ala Leu Pro Phe Ser Tyr
                965                 970                 975

Ala Val Gln Ala Arg Leu Asn Tyr Leu Ala Leu Gln Thr Asp Val Leu
                980                 985                 990

Gln Arg Asn Gln Gln Leu Leu Ala Glu Ser Phe Asn Ser Ala Ile Gly
                995                 1000                1005

Asn Ile Thr Ser Ala Phe Glu Ser Val Lys Glu Ala Ile Ser Gln
        1010                1015                1020

Thr Ser Lys Gly Leu Asn Thr Val Ala His Ala Leu Thr Lys Val
        1025                1030                1035

Gln Glu Val Val Asn Ser Gln Gly Ala Ala Leu Thr Gln Leu Thr
        1040                1045                1050

Val Gln Leu Gln His Asn Phe Gln Ala Ile Ser Ser Ser Ile Asp
        1055                1060                1065

Asp Ile Tyr Ser Arg Leu Asp Ile Leu Ser Ala Asp Val Gln Val
        1070                1075                1080

Asp Arg Leu Ile Thr Gly Arg Leu Ser Ala Leu Asn Ala Phe Val
        1085                1090                1095

Ala Gln Thr Leu Thr Lys Tyr Thr Glu Val Gln Ala Ser Arg Lys
        1100                1105                1110

Leu Ala Gln Gln Lys Val Asn Glu Cys Val Lys Ser Gln Ser Gln
        1115                1120                1125

Arg Tyr Gly Phe Cys Gly Gly Asp Gly Glu His Ile Phe Ser Leu
        1130                1135                1140

-continued

Val Gln Ala Ala Pro Gln Gly Leu Leu Phe Leu His Thr Val Leu
    1145                1150                1155

Val Pro Ser Asp Phe Val Asp Val Ile Ala Ile Ala Gly Leu Cys
    1160                1165                1170

Val Asn Asp Glu Ile Ala Leu Thr Leu Arg Glu Pro Gly Leu Val
    1175                1180                1185

Leu Phe Thr His Glu Leu Gln Asn His Thr Ala Thr Glu Tyr Phe
    1190                1195                1200

Val Ser Ser Arg Arg Met Phe Glu Pro Arg Lys Pro Thr Val Ser
    1205                1210                1215

Asp Phe Val Gln Ile Glu Ser Cys Val Val Thr Tyr Val Asn Leu
    1220                1225                1230

Thr Arg Asp Gln Leu Pro Asp Val Ile Pro Asp Tyr Ile Asp Val
    1235                1240                1245

Asn Lys Thr Leu Asp Glu Ile Leu Ala Ser Leu Pro Asn Arg Thr
    1250                1255                1260

Gly Pro Ser Leu Pro Leu Asp Val Phe Asn Ala Thr Tyr Leu Asn
    1265                1270                1275

Leu Thr Gly Glu Ile Ala Asp Leu Glu Gln Arg Ser Glu Ser Leu
    1280                1285                1290

Arg Asn Thr Thr Glu Glu Leu Gln Ser Leu Ile Tyr Asn Ile Asn
    1295                1300                1305

Asn Thr Leu Val Asp Leu Glu Trp Leu Asn Arg Val Glu Thr Tyr
    1310                1315                1320

Ile Lys Trp Pro Trp Trp Val Trp Leu Ile Ile Phe Ile Val Leu
    1325                1330                1335

Ile Phe Val Val Ser Leu Leu Val Phe Cys Cys Ile Ser Thr Gly
    1340                1345                1350

Cys Cys Gly Cys Cys Gly Cys Cys Cys Ala Cys Phe Ser Gly Cys
    1355                1360                1365

Cys Arg Gly Pro Arg Leu Gln Pro Tyr Glu Val Phe Glu Lys Val
    1370                1375                1380

His Val Gln Cys Gly
    1385

<210> SEQ ID NO 17
<211> LENGTH: 1388
<212> TYPE: PRT
<213> ORGANISM: porcine epidemic diarrhea virus

<400> SEQUENCE: 17

Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Asn Thr Asn Phe
                20                  25                  30

Arg Arg Phe Phe Ser Lys Phe Asn Val Gln Ala Pro Ala Val Val Val
            35                  40                  45

Leu Gly Gly Tyr Leu Pro Ile Gly Glu Asn Gln Gly Val Asn Ser Thr
        50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
                100                 105                 110

```
Thr Asn Gly Asn Thr Asn Ala Thr Ala Arg Leu Arg Ile Cys Gln Phe
            115                 120                 125

Pro Ser Ile Lys Thr Leu Gly Pro Thr Ala Asn Asn Asp Val Thr Thr
            130                 135                 140

Gly Arg Asn Cys Leu Phe Asn Lys Ala Ile Pro Ala His Met Ser Glu
145                 150                 155                 160

His Ser Val Val Gly Ile Thr Trp Asp Asn Asp Arg Val Thr Val Phe
            165                 170                 175

Ser Asp Lys Ile Tyr Tyr Phe Tyr Lys Asn Asp Trp Ser Arg Val
            180                 185                 190

Ala Thr Lys Cys Tyr Asn Ser Gly Gly Cys Ala Met Gln Tyr Val Tyr
            195                 200                 205

Glu Pro Thr Tyr Tyr Met Leu Asn Val Thr Ser Ala Gly Glu Asp Gly
            210                 215                 220

Ile Ser Tyr Gln Pro Cys Thr Ala Asn Cys Ile Gly Tyr Ala Ala Asn
225                 230                 235                 240

Val Phe Ala Thr Glu Pro Asn Gly His Ile Pro Glu Gly Phe Ser Phe
            245                 250                 255

Asn Asn Trp Phe Leu Leu Ser Asn Asp Ser Thr Leu Val His Gly Lys
            260                 265                 270

Val Val Ser Asn Gln Pro Leu Leu Val Asn Cys Leu Leu Ala Ile Pro
            275                 280                 285

Lys Ile Tyr Gly Leu Gly Gln Phe Phe Ser Phe Asn Gln Thr Ile Asp
            290                 295                 300

Gly Val Cys Asn Gly Ala Ala Val Gln Arg Ala Pro Glu Ala Leu Arg
305                 310                 315                 320

Phe Asn Ile Asn Asp Thr Ser Val Ile Leu Ala Glu Gly Ser Ile Val
            325                 330                 335

Leu His Thr Ala Leu Gly Thr Asn Phe Ser Phe Val Cys Ser Asn Ser
            340                 345                 350

Ser Asn Pro His Leu Ala Thr Phe Ala Ile Pro Leu Gly Ala Thr Gln
            355                 360                 365

Val Pro Tyr Tyr Cys Phe Leu Lys Val Asp Thr Tyr Asn Ser Thr Val
            370                 375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
            405                 410                 415

Gly Leu Leu Asp Ala Val Thr Ile Asn Phe Thr Gly His Gly Thr Asp
            420                 425                 430

Asp Asp Val Ser Gly Phe Trp Thr Ile Ala Ser Thr Asn Phe Val Asp
            435                 440                 445

Ala Leu Ile Glu Val Gln Gly Thr Ala Ile Gln Arg Ile Leu Tyr Cys
450                 455                 460

Asp Asp Pro Val Ser Gln Leu Lys Cys Ser Gln Val Ala Phe Asp Leu
465                 470                 475                 480

Asp Asp Gly Phe Tyr Pro Ile Ser Ser Arg Asn Leu Leu Ser His Glu
            485                 490                 495

Gln Pro Ile Ser Phe Val Thr Leu Pro Ser Phe Asn Asp His Ser Phe
            500                 505                 510

Val Asn Ile Thr Val Ser Ala Ser Phe Gly Gly His Ser Gly Ala Asn
            515                 520                 525
```

```
Leu Ile Ala Ser Asp Thr Thr Ile Asn Gly Phe Ser Ser Phe Cys Val
    530                 535                 540

Asp Thr Arg Gln Phe Thr Ile Ser Leu Phe Tyr Asn Val Thr Asn Ser
545                 550                 555                 560

Tyr Gly Tyr Val Ser Lys Ser Gln Asp Ser Asn Cys Pro Phe Thr Leu
                565                 570                 575

Gln Ser Val Asn Asp Tyr Leu Ser Phe Ser Lys Phe Cys Val Ser Thr
            580                 585                 590

Ser Leu Leu Ala Ser Ala Cys Thr Ile Asp Leu Phe Gly Tyr Pro Glu
        595                 600                 605

Phe Gly Ser Gly Val Lys Phe Thr Ser Leu Tyr Phe Gln Phe Thr Lys
    610                 615                 620

Gly Glu Leu Ile Thr Gly Thr Pro Lys Pro Leu Glu Gly Val Thr Asp
625                 630                 635                 640

Val Ser Phe Met Thr Leu Asp Val Cys Thr Lys Tyr Thr Ile Tyr Gly
                645                 650                 655

Phe Lys Gly Glu Gly Ile Ile Thr Leu Thr Asn Ser Ser Phe Leu Ala
            660                 665                 670

Gly Val Tyr Tyr Thr Ser Asp Ser Gly Gln Leu Leu Ala Phe Lys Asn
        675                 680                 685

Val Thr Ser Gly Ala Val Tyr Ser Val Thr Pro Cys Ser Phe Ser Glu
    690                 695                 700

Gln Ala Ala Tyr Val Asp Asp Ile Val Gly Val Ile Ser Ser Leu
705                 710                 715                 720

Ser Ser Ser Thr Phe Asn Ser Thr Arg Glu Leu Pro Gly Phe Phe Tyr
                725                 730                 735

His Ser Asn Asp Gly Ser Asn Cys Thr Glu Pro Val Leu Val Tyr Ser
            740                 745                 750

Asn Ile Gly Val Cys Lys Ser Gly Ser Ile Gly Tyr Val Pro Ser Gln
        755                 760                 765

Ser Gly Gln Val Lys Ile Ala Pro Thr Val Thr Gly Asn Ile Ser Ile
    770                 775                 780

Pro Thr Asn Phe Ser Met Ser Ile Arg Thr Glu Tyr Leu Gln Leu Tyr
785                 790                 795                 800

Asn Thr Pro Val Ser Val Asp Cys Ala Thr Tyr Val Cys Asn Gly Asn
                805                 810                 815

Ser Arg Cys Lys Gln Leu Leu Thr Gln Tyr Thr Ala Ala Cys Lys Thr
            820                 825                 830

Ile Glu Ser Ala Leu Gln Leu Ser Ala Arg Leu Glu Ser Val Glu Val
        835                 840                 845

Asn Ser Met Leu Thr Ile Ser Glu Glu Ala Leu Gln Leu Ala Thr Ile
    850                 855                 860

Ser Ser Phe Asn Gly Asp Gly Tyr Asn Phe Thr Asn Val Leu Gly Val
865                 870                 875                 880

Ser Val Tyr Asp Pro Ala Ser Gly Arg Val Val Gln Lys Arg Ser Phe
                885                 890                 895

Ile Glu Asp Ala Ala Phe Asn Lys Val Val Thr Asn Gly Leu Gly Thr
            900                 905                 910

Val Asp Glu Asp Tyr Lys Arg Cys Ser Asn Gly Arg Ser Val Ala Asp
        915                 920                 925

Leu Val Cys Ala Gln Tyr Tyr Ser Gly Val Met Val Leu Pro Gly Val
    930                 935                 940

Val Asp Ala Glu Lys Leu His Met Tyr Ser Ala Ser Leu Ile Gly Gly
```

```
                945            950             955            960
        Met Val Leu Gly Gly Phe Thr Ser Ala Ala Ala Leu Pro Phe Ser Tyr
                        965             970            975

Ala Val Gln Ala Arg Leu Asn Tyr Leu Ala Leu Gln Thr Asp Val Leu
                        980             985            990

Gln Arg Asn Gln Gln Leu Leu Ala Glu Ser Phe Asn Ser Ala Ile Gly
                        995            1000           1005

Asn Ile Thr Ser Ala Phe Glu Ser Val Lys Glu Ala Ile Ser Gln
               1010            1015           1020

Thr Ser Lys Gly Leu Asn Thr Val Ala His Ala Leu Thr Lys Val
               1025            1030           1035

Gln Glu Val Val Asn Ser Gln Gly Ala Ala Leu Thr Gln Leu Thr
               1040            1045           1050

Val Gln Leu Gln His Asn Phe Gln Ala Ile Ser Ser Ser Ile Asp
               1055            1060           1065

Asp Ile Tyr Ser Arg Leu Asp Ile Leu Ser Ala Asp Val Gln Val
               1070            1075           1080

Asp Arg Leu Ile Thr Gly Arg Leu Ser Ala Leu Asn Ala Phe Val
               1085            1090           1095

Ala Gln Thr Leu Thr Lys Tyr Thr Glu Val Gln Ala Ser Arg Lys
               1100            1105           1110

Leu Ala Gln Gln Lys Val Asn Glu Cys Val Lys Ser Gln Ser Gln
               1115            1120           1125

Arg Tyr Gly Phe Cys Gly Gly Asp Gly Glu His Ile Phe Ser Leu
               1130            1135           1140

Val Gln Ala Ala Pro Gln Gly Leu Leu Phe Leu His Thr Val Leu
               1145            1150           1155

Val Pro Ser Asp Phe Val Asp Val Ile Ala Ile Ala Gly Leu Cys
               1160            1165           1170

Val Asn Asp Glu Ile Ala Leu Thr Leu Arg Glu Pro Gly Leu Val
               1175            1180           1185

Leu Phe Thr His Glu Leu Gln Asn His Thr Ala Thr Glu Tyr Phe
               1190            1195           1200

Val Ser Ser Arg Arg Met Phe Glu Pro Arg Lys Pro Thr Val Ser
               1205            1210           1215

Asp Phe Val Gln Ile Glu Ser Cys Val Val Thr Tyr Val Asn Leu
               1220            1225           1230

Thr Arg Asp Gln Leu Pro Val Ile Pro Asp Tyr Ile Asp Val
               1235            1240           1245

Asn Lys Thr Leu Asp Glu Ile Leu Ala Ser Leu Pro Asn Arg Thr
               1250            1255           1260

Gly Pro Ser Leu Pro Leu Asp Val Phe Asn Ala Thr Tyr Leu Asn
               1265            1270           1275

Leu Thr Gly Glu Ile Ala Asp Leu Glu Gln Arg Ser Glu Ser Leu
               1280            1285           1290

Arg Asn Thr Thr Glu Glu Leu Gln Ser Leu Ile Tyr Asn Ile Asn
               1295            1300           1305

Asn Thr Leu Val Asp Leu Glu Trp Leu Asn Arg Val Glu Thr Tyr
               1310            1315           1320

Ile Lys Trp Pro Trp Trp Val Trp Leu Ile Ile Phe Ile Val Leu
               1325            1330           1335

Ile Phe Val Val Ser Leu Leu Val Phe Cys Cys Ile Ser Thr Gly
               1340            1345           1350
```

-continued

```
Cys Cys Gly Cys Cys Gly Cys  Cys Cys Ala Cys Phe  Ser Gly Cys
    1355              1360              1365

Cys Arg Gly Pro Arg Leu Gln  Pro Tyr Glu Val Phe  Glu Lys Val
    1370              1375              1380

His Val Gln Cys Gly
    1385

<210> SEQ ID NO 18
<211> LENGTH: 1388
<212> TYPE: PRT
<213> ORGANISM: porcine epidemic diarrhea virus

<400> SEQUENCE: 18

Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Asn Thr Asn Phe
                20                  25                  30

Arg Arg Phe Phe Ser Lys Phe Asn Val Gln Ala Pro Ala Val Val Val
            35                  40                  45

Leu Gly Gly Tyr Leu Pro Ile Gly Glu Asn Gln Gly Val Asn Ser Thr
50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
            100                 105                 110

Thr Asn Gly Asn Thr Asn Ala Thr Ala Arg Leu Arg Ile Cys Gln Phe
        115                 120                 125

Pro Ser Ile Lys Thr Leu Gly Pro Thr Ala Asn Asn Asp Val Thr Thr
130                 135                 140

Gly Arg Asn Cys Leu Phe Asn Lys Ala Ile Pro Ala His Met Ser Glu
145                 150                 155                 160

His Ser Val Val Gly Ile Thr Trp Asp Asn Asp Arg Val Thr Val Phe
                165                 170                 175

Ser Asp Lys Ile Tyr Tyr Phe Tyr Phe Lys Asn Asp Trp Ser Arg Val
            180                 185                 190

Ala Thr Lys Cys Tyr Asn Ser Gly Gly Cys Ala Met Gln Tyr Val Tyr
        195                 200                 205

Glu Pro Thr Tyr Tyr Met Leu Asn Val Thr Ser Ala Gly Glu Asp Gly
210                 215                 220

Ile Ser Tyr Gln Pro Cys Thr Ala Asn Cys Ile Gly Tyr Ala Ala Asn
225                 230                 235                 240

Val Phe Ala Thr Glu Pro Asn Gly His Ile Pro Glu Gly Phe Ser Phe
                245                 250                 255

Asn Asn Trp Phe Leu Leu Ser Asn Asp Ser Thr Leu Val His Gly Lys
            260                 265                 270

Val Val Ser Asn Gln Pro Leu Leu Val Asn Cys Leu Leu Ala Ile Pro
        275                 280                 285

Lys Ile Tyr Gly Leu Gly Gln Phe Phe Ser Phe Asn Gln Thr Ile Asp
290                 295                 300

Gly Val Cys Asn Gly Ala Ala Val Gln Arg Ala Pro Glu Ala Leu Arg
305                 310                 315                 320

Phe Asn Ile Asn Asp Thr Ser Val Ile Leu Ala Glu Gly Ser Ile Val
```

```
                    325                 330                 335
Leu His Thr Ala Leu Gly Thr Asn Phe Ser Phe Val Cys Ser Asn Ser
                340                 345                 350
Ser Asn Pro His Leu Ala Thr Phe Ala Ile Pro Leu Gly Ala Thr Gln
                355                 360                 365
Val Pro Tyr Tyr Cys Phe Leu Lys Val Asp Thr Tyr Asn Ser Thr Val
            370                 375                 380
Tyr Lys Phe Leu Ala Val Leu Pro Pro Thr Val Arg Glu Ile Val Ile
385                 390                 395                 400
Thr Lys Tyr Gly Asp Val Tyr Val Asn Gly Phe Gly Tyr Leu His Leu
                405                 410                 415
Gly Leu Leu Asp Ala Val Thr Ile Asn Phe Thr Gly His Gly Thr Asp
                420                 425                 430
Asp Asp Val Ser Gly Phe Trp Thr Ile Ala Ser Thr Asn Phe Val Asp
                435                 440                 445
Ala Leu Ile Glu Val Gln Gly Thr Ala Ile Gln Arg Ile Leu Tyr Cys
                450                 455                 460
Asp Asp Pro Val Ser Gln Leu Lys Cys Ser Gln Val Ala Phe Asp Leu
465                 470                 475                 480
Asp Asp Gly Phe Tyr Pro Ile Ser Ser Arg Asn Leu Leu Ser His Glu
                485                 490                 495
Gln Pro Ile Ser Phe Val Thr Leu Pro Ser Phe Asn Asp His Ser Phe
                500                 505                 510
Val Asn Ile Thr Val Ser Ala Ser Phe Gly Gly His Ser Gly Ala Asn
                515                 520                 525
Leu Ile Ala Ser Asp Thr Thr Ile Asn Gly Phe Ser Ser Phe Cys Val
                530                 535                 540
Asp Thr Arg Gln Phe Thr Ile Ser Leu Phe Tyr Asn Val Thr Asn Ser
545                 550                 555                 560
Tyr Gly Tyr Val Ser Lys Ser Gln Asp Ser Asn Cys Pro Phe Thr Leu
                565                 570                 575
Gln Ser Val Asn Asp Tyr Leu Ser Phe Ser Lys Phe Cys Val Ser Thr
                580                 585                 590
Ser Leu Leu Ala Ser Ala Cys Thr Ile Asp Leu Phe Gly Tyr Pro Glu
                595                 600                 605
Phe Gly Ser Gly Val Lys Phe Thr Ser Leu Tyr Phe Gln Phe Thr Lys
                610                 615                 620
Gly Glu Leu Ile Thr Gly Thr Pro Lys Pro Leu Glu Gly Val Thr Asp
625                 630                 635                 640
Val Ser Phe Met Thr Leu Asp Val Cys Thr Lys Tyr Thr Ile Tyr Gly
                645                 650                 655
Phe Lys Gly Glu Gly Ile Ile Thr Leu Thr Asn Ser Ser Phe Leu Ala
                660                 665                 670
Gly Val Tyr Tyr Thr Ser Asp Ser Gly Gln Leu Leu Ala Phe Lys Asn
                675                 680                 685
Val Thr Ser Gly Ala Val Tyr Ser Val Thr Pro Cys Ser Phe Ser Glu
                690                 695                 700
Gln Ala Ala Tyr Val Asp Asp Ile Val Gly Val Ile Ser Ser Leu
705                 710                 715                 720
Ser Ser Ser Thr Phe Asn Ser Thr Arg Glu Leu Pro Gly Phe Phe Tyr
                725                 730                 735
His Ser Asn Asp Gly Ser Asn Cys Thr Glu Pro Val Leu Val Tyr Ser
                740                 745                 750
```

```
Asn Ile Gly Val Cys Lys Ser Gly Ser Ile Gly Tyr Val Pro Ser Gln
    755                 760                 765

Ser Gly Gln Val Lys Ile Ala Pro Thr Val Thr Gly Asn Ile Ser Ile
    770                 775                 780

Pro Thr Asn Phe Ser Met Ser Ile Arg Thr Glu Tyr Leu Gln Leu Tyr
785                 790                 795                 800

Asn Thr Pro Val Ser Val Asp Cys Ala Thr Tyr Val Cys Asn Gly Asn
                805                 810                 815

Ser Arg Cys Lys Gln Leu Leu Thr Gln Tyr Thr Ala Ala Cys Lys Thr
                820                 825                 830

Ile Glu Ser Ala Leu Gln Leu Ser Ala Arg Leu Glu Ser Val Glu Val
                835                 840                 845

Asn Ser Met Leu Thr Ile Ser Glu Glu Ala Leu Gln Leu Ala Thr Ile
850                 855                 860

Ser Ser Phe Asn Gly Asp Gly Tyr Asn Phe Thr Asn Val Leu Gly Val
865                 870                 875                 880

Ser Val Tyr Asp Pro Ala Ser Gly Arg Val Val Gln Lys Arg Ser Phe
                885                 890                 895

Ile Glu Asp Ala Leu Phe Asn Lys Val Val Thr Asn Gly Leu Gly Thr
                900                 905                 910

Val Asp Glu Asp Tyr Lys Arg Cys Ser Asn Gly Arg Ser Val Ala Asp
                915                 920                 925

Leu Val Cys Ala Gln Tyr Tyr Ser Gly Val Met Val Leu Pro Gly Val
    930                 935                 940

Val Asp Ala Glu Lys Leu His Met Tyr Ser Ala Ser Leu Ile Gly Gly
945                 950                 955                 960

Met Val Leu Gly Gly Phe Thr Ser Ala Ala Ala Leu Pro Phe Ser Tyr
                965                 970                 975

Ala Val Gln Ala Arg Leu Asn Tyr Leu Ala Leu Gln Thr Asp Val Leu
                980                 985                 990

Gln Arg Asn Gln Gln Leu Leu Ala Glu Ser Phe Asn Ser Ala Ile Gly
    995                 1000                1005

Asn Ile Thr Ser Ala Phe Glu Ser Val Lys Glu Ala Ile Ser Gln
    1010                1015                1020

Thr Ser Lys Gly Leu Asn Thr Val Ala His Ala Leu Thr Lys Val
    1025                1030                1035

Gln Glu Val Val Asn Ser Gln Gly Ala Ala Leu Thr Gln Leu Thr
    1040                1045                1050

Val Gln Leu Gln His Asn Phe Gln Ala Ile Ser Ser Ser Ile Asp
    1055                1060                1065

Asp Ile Tyr Ser Arg Leu Asp Ile Leu Ser Ala Asp Val Gln Val
    1070                1075                1080

Asp Arg Leu Ile Thr Gly Arg Leu Ser Ala Leu Asn Ala Phe Val
    1085                1090                1095

Ala Gln Thr Leu Thr Lys Tyr Thr Glu Val Gln Ala Ser Arg Lys
    1100                1105                1110

Leu Ala Gln Gln Lys Val Asn Glu Cys Val Lys Ser Gln Ser Gln
    1115                1120                1125

Arg Tyr Gly Phe Cys Gly Gly Asp Gly Glu His Ile Phe Ser Leu
    1130                1135                1140

Val Gln Ala Ala Pro Gln Gly Leu Leu Phe Leu His Thr Val Leu
    1145                1150                1155
```

Val Pro Ser Asp Phe Val Asp Val Ile Ala Ile Ala Gly Leu Cys
1160                1165                1170

Val Asn Asp Glu Ile Ala Leu Thr Leu Arg Glu Pro Gly Leu Val
1175                1180                1185

Leu Phe Thr His Glu Leu Gln Asn His Thr Ala Thr Glu Tyr Phe
1190                1195                1200

Val Ser Ser Arg Arg Met Phe Glu Pro Arg Lys Pro Thr Val Ser
1205                1210                1215

Asp Phe Val Gln Ile Glu Ser Cys Val Val Thr Tyr Val Asn Leu
1220                1225                1230

Thr Arg Asp Gln Leu Pro Asp Val Ile Pro Asp Tyr Ile Asp Val
1235                1240                1245

Asn Lys Thr Leu Asp Glu Ile Leu Ala Ser Leu Pro Asn Arg Thr
1250                1255                1260

Gly Pro Ser Leu Pro Leu Asp Val Phe Asn Ala Thr Tyr Leu Asn
1265                1270                1275

Leu Thr Gly Glu Ile Ala Asp Leu Glu Gln Arg Ser Glu Ser Leu
1280                1285                1290

Arg Asn Thr Thr Glu Glu Leu Gln Ser Leu Ile Tyr Asn Ile Asn
1295                1300                1305

Asn Thr Leu Val Asp Leu Glu Trp Leu Asn Arg Val Glu Thr Tyr
1310                1315                1320

Ile Lys Trp Pro Trp Trp Val Trp Leu Ile Ile Phe Ile Val Leu
1325                1330                1335

Ile Phe Val Val Ser Leu Leu Val Phe Cys Cys Ile Ser Thr Gly
1340                1345                1350

Cys Cys Gly Cys Cys Gly Cys Cys Ala Cys Phe Ser Gly Cys
1355                1360                1365

Cys Arg Gly Pro Arg Leu Gln Pro Ala Glu Val Phe Glu Lys Val
1370                1375                1380

Arg Val Gln Cys Gly
1385

<210> SEQ ID NO 19
<211> LENGTH: 1388
<212> TYPE: PRT
<213> ORGANISM: porcine epidemic diarrhea virus

<400> SEQUENCE: 19

Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Asn Thr Asn Phe
                20                  25                  30

Arg Arg Phe Phe Ser Lys Phe Asn Val Gln Ala Pro Ala Val Val Val
            35                  40                  45

Leu Gly Gly Tyr Leu Pro Ile Gly Glu Asn Gln Gly Val Asn Ser Thr
        50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
                100                 105                 110

Thr Asn Gly Asn Thr Asn Ala Thr Ala Arg Leu Arg Ile Cys Gln Phe
            115                 120                 125

-continued

Pro Ser Ile Lys Thr Leu Gly Pro Thr Ala Asn Asn Asp Val Thr Thr
    130                 135                 140

Gly Arg Asn Cys Leu Phe Asn Lys Ala Ile Pro Ala His Met Ser Glu
145                 150                 155                 160

His Ser Val Val Gly Ile Thr Trp Asp Asn Asp Arg Val Thr Val Phe
                165                 170                 175

Ser Asp Lys Ile Tyr Tyr Phe Tyr Lys Asn Asp Trp Ser Arg Val
            180                 185                 190

Ala Thr Lys Cys Tyr Asn Ser Gly Cys Ala Met Gln Tyr Val Tyr
        195                 200                 205

Glu Pro Thr Tyr Tyr Met Leu Asn Val Thr Ser Ala Gly Glu Asp Gly
    210                 215                 220

Ile Ser Tyr Gln Pro Cys Thr Ala Asn Cys Ile Gly Tyr Ala Ala Asn
225                 230                 235                 240

Val Phe Ala Thr Glu Pro Asn Gly His Ile Pro Glu Gly Phe Ser Phe
                245                 250                 255

Asn Asn Trp Phe Leu Leu Ser Asn Asp Ser Thr Leu Val His Gly Lys
            260                 265                 270

Val Val Ser Asn Gln Pro Leu Leu Val Asn Cys Leu Leu Ala Ile Pro
        275                 280                 285

Lys Ile Tyr Gly Leu Gly Gln Phe Phe Ser Phe Asn Gln Thr Ile Asp
    290                 295                 300

Gly Val Cys Asn Gly Ala Ala Val Gln Arg Ala Pro Glu Ala Leu Arg
305                 310                 315                 320

Phe Asn Ile Asn Asp Thr Ser Val Ile Leu Ala Glu Gly Ser Ile Val
                325                 330                 335

Leu His Thr Ala Leu Gly Thr Asn Phe Ser Phe Val Cys Ser Asn Ser
            340                 345                 350

Ser Asn Pro His Leu Ala Thr Phe Ala Ile Pro Leu Gly Ala Thr Gln
        355                 360                 365

Val Pro Tyr Tyr Cys Phe Leu Lys Val Asp Thr Tyr Asn Ser Thr Val
    370                 375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
                405                 410                 415

Gly Leu Leu Asp Ala Val Thr Ile Asn Phe Thr Gly His Gly Thr Asp
            420                 425                 430

Asp Asp Val Ser Gly Phe Trp Thr Ile Ala Ser Thr Asn Phe Val Asp
        435                 440                 445

Ala Leu Ile Glu Val Gln Gly Thr Ala Ile Gln Arg Ile Leu Tyr Cys
    450                 455                 460

Asp Asp Pro Val Ser Gln Leu Lys Cys Ser Gln Val Ala Phe Asp Leu
465                 470                 475                 480

Asp Asp Gly Phe Tyr Pro Ile Ser Ser Arg Asn Leu Leu Ser His Glu
                485                 490                 495

Gln Pro Ile Ser Phe Val Thr Leu Pro Ser Phe Asn Asp His Ser Phe
            500                 505                 510

Val Asn Ile Thr Val Ser Ala Ser Phe Gly Gly His Ser Gly Ala Asn
        515                 520                 525

Leu Ile Ala Ser Asp Thr Thr Ile Asn Gly Phe Ser Ser Phe Cys Val
530                 535                 540

```
Asp Thr Arg Gln Phe Thr Ile Ser Leu Phe Tyr Asn Val Thr Asn Ser
545                 550                 555                 560

Tyr Gly Tyr Val Ser Lys Ser Gln Asp Ser Asn Cys Pro Phe Thr Leu
                565                 570                 575

Gln Ser Val Asn Asp Tyr Leu Ser Phe Ser Lys Phe Cys Val Ser Thr
            580                 585                 590

Ser Leu Leu Ala Ser Ala Cys Thr Ile Asp Leu Phe Gly Tyr Pro Glu
        595                 600                 605

Phe Gly Ser Gly Val Lys Phe Thr Ser Leu Tyr Phe Gln Phe Thr Lys
    610                 615                 620

Gly Glu Leu Ile Thr Gly Thr Pro Lys Pro Leu Glu Gly Val Thr Asp
625                 630                 635                 640

Val Ser Phe Met Thr Leu Asp Val Cys Thr Lys Tyr Thr Ile Tyr Gly
                645                 650                 655

Phe Lys Gly Glu Gly Ile Ile Thr Leu Thr Asn Ser Ser Phe Leu Ala
                660                 665                 670

Gly Val Tyr Tyr Thr Ser Asp Ser Gly Gln Leu Leu Ala Phe Lys Asn
            675                 680                 685

Val Thr Ser Gly Ala Val Tyr Ser Val Thr Pro Cys Ser Phe Ser Glu
        690                 695                 700

Gln Ala Ala Tyr Val Asp Asp Ile Val Gly Val Ile Ser Ser Leu
705                 710                 715                 720

Ser Ser Ser Thr Phe Asn Ser Thr Arg Glu Leu Pro Gly Phe Phe Tyr
                725                 730                 735

His Ser Asn Asp Gly Ser Asn Cys Thr Glu Pro Val Leu Val Tyr Ser
                740                 745                 750

Asn Ile Gly Val Cys Lys Ser Gly Ser Ile Gly Tyr Val Pro Ser Gln
            755                 760                 765

Ser Gly Gln Val Lys Ile Ala Pro Thr Val Thr Gly Asn Ile Ser Ile
        770                 775                 780

Pro Thr Asn Phe Ser Met Ser Ile Arg Thr Glu Tyr Leu Gln Leu Tyr
785                 790                 795                 800

Asn Thr Pro Val Ser Val Asp Cys Ala Thr Tyr Val Cys Asn Gly Asn
                805                 810                 815

Ser Arg Cys Lys Gln Leu Leu Thr Gln Tyr Thr Ala Ala Cys Lys Thr
                820                 825                 830

Ile Glu Ser Ala Leu Gln Leu Ser Ala Arg Leu Glu Ser Val Glu Val
            835                 840                 845

Asn Ser Met Leu Thr Ile Ser Glu Glu Ala Leu Gln Leu Ala Thr Ile
850                 855                 860

Ser Ser Phe Asn Gly Asp Gly Tyr Asn Phe Thr Asn Val Leu Gly Val
865                 870                 875                 880

Ser Val Tyr Asp Pro Ala Ser Gly Arg Val Val Gln Lys Arg Ser Phe
                885                 890                 895

Ile Glu Asp Leu Ala Phe Asn Lys Val Val Thr Asn Gly Leu Gly Thr
            900                 905                 910

Val Asp Glu Asp Tyr Lys Arg Cys Ser Asn Gly Arg Ser Val Ala Asp
        915                 920                 925

Leu Val Cys Ala Gln Tyr Tyr Ser Gly Val Met Val Leu Pro Gly Val
    930                 935                 940

Val Asp Ala Glu Lys Leu His Met Tyr Ser Ala Ser Leu Ile Gly Gly
945                 950                 955                 960

Met Val Leu Gly Gly Phe Thr Ser Ala Ala Ala Leu Pro Phe Ser Tyr
```

-continued

```
                965                 970                 975
Ala Val Gln Ala Arg Leu Asn Tyr Leu Ala Leu Gln Thr Asp Val Leu
                    980                 985                 990
Gln Arg Asn Gln Gln Leu Leu Ala  Glu Ser Phe Asn Ser  Ala Ile Gly
        995                 1000                1005
Asn Ile Thr Ser Ala Phe Glu  Ser Val Lys Glu Ala  Ile Ser Gln
    1010                1015                1020
Thr Ser Lys Gly Leu Asn Thr  Val Ala His Ala Leu  Thr Lys Val
    1025                1030                1035
Gln Glu Val Val Asn Ser Gln  Gly Ala Ala Leu Thr  Gln Leu Thr
    1040                1045                1050
Val Gln Leu Gln His Asn Phe  Gln Ala Ile Ser Ser  Ser Ile Asp
    1055                1060                1065
Asp Ile Tyr Ser Arg Leu Asp  Ile Leu Ser Ala Asp  Val Gln Val
    1070                1075                1080
Asp Arg Leu Ile Thr Gly Arg  Leu Ser Ala Leu Asn  Ala Phe Val
    1085                1090                1095
Ala Gln Thr Leu Thr Lys Tyr  Thr Glu Val Gln Ala  Ser Arg Lys
    1100                1105                1110
Leu Ala Gln Gln Lys Val Asn  Glu Cys Val Lys Ser  Gln Ser Gln
    1115                1120                1125
Arg Tyr Gly Phe Cys Gly Gly  Asp Gly Glu His Ile  Phe Ser Leu
    1130                1135                1140
Val Gln Ala Ala Pro Gln Gly  Leu Leu Phe Leu His  Thr Val Leu
    1145                1150                1155
Val Pro Ser Asp Phe Val Asp  Val Ile Ala Ile Ala  Gly Leu Cys
    1160                1165                1170
Val Asn Asp Glu Ile Ala Leu  Thr Leu Arg Glu Pro  Gly Leu Val
    1175                1180                1185
Leu Phe Thr His Glu Leu Gln  Asn His Thr Ala Thr  Glu Tyr Phe
    1190                1195                1200
Val Ser Ser Arg Arg Met Phe  Glu Pro Arg Lys Pro  Thr Val Ser
    1205                1210                1215
Asp Phe Val Gln Ile Glu Ser  Cys Val Val Thr Tyr  Val Asn Leu
    1220                1225                1230
Thr Arg Asp Gln Leu Pro Asp  Val Ile Pro Asp Tyr  Ile Asp Val
    1235                1240                1245
Asn Lys Thr Leu Asp Glu Ile  Leu Ala Ser Leu Pro  Asn Arg Thr
    1250                1255                1260
Gly Pro Ser Leu Pro Leu Asp  Val Phe Asn Ala Thr  Tyr Leu Asn
    1265                1270                1275
Leu Thr Gly Glu Ile Ala Asp  Leu Glu Gln Arg Ser  Glu Ser Leu
    1280                1285                1290
Arg Asn Thr Thr Glu Glu Leu  Gln Ser Leu Ile Tyr  Asn Ile Asn
    1295                1300                1305
Asn Thr Leu Val Asp Leu Glu  Trp Leu Asn Arg Val  Glu Thr Tyr
    1310                1315                1320
Ile Lys Trp Pro Trp Trp Val  Trp Leu Ile Ile Phe  Ile Val Leu
    1325                1330                1335
Ile Phe Val Val Ser Leu Leu  Val Phe Cys Cys Ile  Ser Thr Gly
    1340                1345                1350
Cys Cys Gly Cys Cys Gly Cys  Cys Cys Ala Cys Phe  Ser Gly Cys
    1355                1360                1365
```

```
Cys Arg Gly Pro Arg Leu Gln Pro Ala Glu Val Phe Glu Lys Val
    1370                1375                1380

Arg Val Gln Cys Gly
    1385

<210> SEQ ID NO 20
<211> LENGTH: 1388
<212> TYPE: PRT
<213> ORGANISM: porcine epidemic diarrhea virus

<400> SEQUENCE: 20

Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Asn Thr Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ile Gly Glu Asn Gln Gly Val Asn Ser Thr
    50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
            100                 105                 110

Thr Asn Gly Asn Thr Asn Ala Thr Ala Arg Leu Arg Ile Cys Gln Phe
        115                 120                 125

Pro Ser Ile Lys Thr Leu Gly Pro Thr Ala Asn Asn Asp Val Thr Thr
    130                 135                 140

Gly Arg Asn Cys Leu Phe Asn Lys Ala Ile Pro Ala His Met Ser Glu
145                 150                 155                 160

His Ser Val Val Gly Ile Thr Trp Asp Asn Asp Arg Val Thr Val Phe
                165                 170                 175

Ser Asp Lys Ile Tyr Tyr Phe Tyr Phe Lys Asn Asp Trp Ser Arg Val
            180                 185                 190

Ala Thr Lys Cys Tyr Asn Ser Gly Gly Cys Ala Met Gln Tyr Val Tyr
        195                 200                 205

Glu Pro Thr Tyr Tyr Met Leu Asn Val Thr Ser Ala Gly Glu Asp Gly
    210                 215                 220

Ile Ser Tyr Gln Pro Cys Thr Ala Asn Cys Ile Gly Tyr Ala Ala Asn
225                 230                 235                 240

Val Phe Ala Thr Glu Pro Asn Gly His Ile Pro Glu Gly Phe Ser Phe
                245                 250                 255

Asn Asn Trp Phe Leu Leu Ser Asn Asp Ser Thr Leu Val His Gly Lys
            260                 265                 270

Val Val Ser Asn Gln Pro Leu Leu Val Asn Cys Leu Leu Ala Ile Pro
        275                 280                 285

Lys Ile Tyr Gly Leu Gly Gln Phe Phe Ser Phe Asn Gln Thr Ile Asp
    290                 295                 300

Gly Val Cys Asn Gly Ala Ala Val Gln Arg Ala Pro Glu Ala Leu Arg
305                 310                 315                 320

Phe Asn Ile Asn Asp Thr Ser Val Ile Leu Ala Glu Gly Ser Ile Val
                325                 330                 335

Leu His Thr Ala Leu Gly Thr Asn Phe Ser Phe Val Cys Ser Asn Ser
```

```
                340             345             350
Ser Asn Pro His Leu Ala Thr Phe Ala Ile Pro Leu Gly Ala Thr Gln
            355                 360             365

Val Pro Tyr Tyr Cys Phe Leu Lys Val Asp Thr Tyr Asn Ser Thr Val
370             375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
                405                 410                 415

Gly Leu Leu Asp Ala Val Thr Ile Asn Phe Thr Gly His Gly Thr Asp
                420                 425                 430

Asp Asp Val Ser Gly Phe Trp Thr Ile Ala Ser Thr Asn Phe Val Asp
        435                 440                 445

Ala Leu Ile Glu Val Gln Gly Thr Ala Ile Gln Arg Ile Leu Tyr Cys
        450                 455                 460

Asp Asp Pro Val Ser Gln Leu Lys Cys Ser Gln Val Ala Phe Asp Leu
465                 470                 475                 480

Asp Asp Gly Phe Tyr Pro Ile Ser Ser Arg Asn Leu Leu Ser His Glu
                485                 490                 495

Gln Pro Ile Ser Phe Val Thr Leu Pro Ser Phe Asn Asp His Ser Phe
                500                 505                 510

Val Asn Ile Thr Val Ser Ala Ser Phe Gly Gly His Ser Gly Ala Asn
                515                 520                 525

Leu Ile Ala Ser Asp Thr Thr Ile Asn Gly Phe Ser Ser Phe Cys Val
        530                 535                 540

Asp Thr Arg Gln Phe Thr Ile Ser Leu Phe Tyr Asn Val Thr Asn Ser
545                 550                 555                 560

Tyr Gly Tyr Val Ser Lys Ser Gln Asp Ser Asn Cys Pro Phe Thr Leu
                565                 570                 575

Gln Ser Val Asn Asp Tyr Leu Ser Phe Ser Lys Phe Cys Val Ser Thr
                580                 585                 590

Ser Leu Leu Ala Ser Ala Cys Thr Ile Asp Leu Phe Gly Tyr Pro Glu
        595                 600                 605

Phe Gly Ser Gly Val Lys Phe Thr Ser Leu Tyr Phe Gln Phe Thr Lys
        610                 615                 620

Gly Glu Leu Ile Thr Gly Thr Pro Lys Pro Leu Glu Gly Val Thr Asp
625                 630                 635                 640

Val Ser Phe Met Thr Leu Asp Val Cys Thr Lys Tyr Thr Ile Tyr Gly
                645                 650                 655

Phe Lys Gly Glu Gly Ile Ile Thr Leu Thr Asn Ser Ser Phe Leu Ala
                660                 665                 670

Gly Val Tyr Tyr Thr Ser Asp Ser Gly Gln Leu Leu Ala Phe Lys Asn
                675                 680                 685

Val Thr Ser Gly Ala Val Tyr Ser Val Thr Pro Cys Ser Phe Ser Glu
        690                 695                 700

Gln Ala Ala Tyr Val Asp Asp Ile Val Gly Val Ile Ser Ser Leu
705                 710                 715                 720

Ser Ser Ser Thr Phe Asn Ser Thr Arg Glu Leu Pro Gly Phe Phe Tyr
                725                 730                 735

His Ser Asn Asp Gly Ser Asn Cys Thr Glu Pro Val Leu Val Tyr Ser
                740                 745                 750

Asn Ile Gly Val Cys Lys Ser Gly Ser Ile Gly Tyr Val Pro Ser Gln
                755                 760                 765
```

-continued

Ser Gly Gln Val Lys Ile Ala Pro Thr Val Thr Gly Asn Ile Ser Ile
770             775                 780

Pro Thr Asn Phe Ser Met Ser Ile Arg Thr Glu Tyr Leu Gln Leu Tyr
785             790                 795                 800

Asn Thr Pro Val Ser Val Asp Cys Ala Thr Tyr Val Cys Asn Gly Asn
            805                 810                 815

Ser Arg Cys Lys Gln Leu Leu Thr Gln Tyr Thr Ala Ala Cys Lys Thr
        820                 825                 830

Ile Glu Ser Ala Leu Gln Leu Ser Ala Arg Leu Glu Ser Val Glu Val
        835                 840                 845

Asn Ser Met Leu Thr Ile Ser Glu Glu Ala Leu Gln Leu Ala Thr Ile
850                 855                 860

Ser Ser Phe Asn Gly Asp Gly Tyr Asn Phe Thr Asn Val Leu Gly Val
865                 870                 875                 880

Ser Val Tyr Asp Pro Ala Ser Gly Arg Val Val Gln Lys Arg Ser Phe
            885                 890                 895

Ile Glu Asp Ala Ala Phe Asn Lys Val Val Thr Asn Gly Leu Gly Thr
            900                 905                 910

Val Asp Glu Asp Tyr Lys Arg Cys Ser Asn Gly Arg Ser Val Ala Asp
915                 920                 925

Leu Val Cys Ala Gln Tyr Tyr Ser Gly Val Met Val Leu Pro Gly Val
930                 935                 940

Val Asp Ala Glu Lys Leu His Met Tyr Ser Ala Ser Leu Ile Gly Gly
945                 950                 955                 960

Met Val Leu Gly Gly Phe Thr Ser Ala Ala Ala Leu Pro Phe Ser Tyr
                965                 970                 975

Ala Val Gln Ala Arg Leu Asn Tyr Leu Ala Leu Gln Thr Asp Val Leu
            980                 985                 990

Gln Arg Asn Gln Gln Leu Leu Ala Glu Ser Phe Asn Ser Ala Ile Gly
        995                 1000                1005

Asn Ile Thr Ser Ala Phe Glu Ser Val Lys Glu Ala Ile Ser Gln
        1010                1015                1020

Thr Ser Lys Gly Leu Asn Thr Val Ala His Ala Leu Thr Lys Val
        1025                1030                1035

Gln Glu Val Val Asn Ser Gly Ala Ala Leu Thr Gln Leu Thr
        1040                1045                1050

Val Gln Leu Gln His Asn Phe Gln Ala Ile Ser Ser Ser Ile Asp
        1055                1060                1065

Asp Ile Tyr Ser Arg Leu Asp Ile Leu Ser Ala Asp Val Gln Val
        1070                1075                1080

Asp Arg Leu Ile Thr Gly Arg Leu Ser Ala Leu Asn Ala Phe Val
        1085                1090                1095

Ala Gln Thr Leu Thr Lys Tyr Thr Glu Val Gln Ala Ser Arg Lys
        1100                1105                1110

Leu Ala Gln Gln Lys Val Asn Glu Cys Val Lys Ser Gln Ser Gln
        1115                1120                1125

Arg Tyr Gly Phe Cys Gly Gly Asp Gly Glu His Ile Phe Ser Leu
        1130                1135                1140

Val Gln Ala Ala Pro Gln Gly Leu Leu Phe Leu His Thr Val Leu
        1145                1150                1155

Val Pro Ser Asp Phe Val Asp Val Ile Ala Ile Ala Gly Leu Cys
        1160                1165                1170

-continued

```
Val Asn Asp Glu Ile Ala Leu Thr Leu Arg Glu Pro Gly Leu Val
    1175                1180                1185

Leu Phe Thr His Glu Leu Gln Asn His Thr Ala Thr Glu Tyr Phe
    1190                1195                1200

Val Ser Ser Arg Arg Met Phe Glu Pro Arg Lys Pro Thr Val Ser
    1205                1210                1215

Asp Phe Val Gln Ile Glu Ser Cys Val Val Thr Tyr Val Asn Leu
    1220                1225                1230

Thr Arg Asp Gln Leu Pro Asp Val Ile Pro Asp Tyr Ile Asp Val
    1235                1240                1245

Asn Lys Thr Leu Asp Glu Ile Leu Ala Ser Leu Pro Asn Arg Thr
    1250                1255                1260

Gly Pro Ser Leu Pro Leu Asp Val Phe Asn Ala Thr Tyr Leu Asn
    1265                1270                1275

Leu Thr Gly Glu Ile Ala Asp Leu Glu Gln Arg Ser Glu Ser Leu
    1280                1285                1290

Arg Asn Thr Thr Glu Glu Leu Gln Ser Leu Ile Tyr Asn Ile Asn
    1295                1300                1305

Asn Thr Leu Val Asp Leu Glu Trp Leu Asn Arg Val Glu Thr Tyr
    1310                1315                1320

Ile Lys Trp Pro Trp Trp Val Trp Leu Ile Ile Phe Ile Val Leu
    1325                1330                1335

Ile Phe Val Val Ser Leu Leu Val Phe Cys Cys Ile Ser Thr Gly
    1340                1345                1350

Cys Cys Gly Cys Cys Gly Cys Cys Ala Cys Phe Ser Gly Cys
    1355                1360                1365

Cys Arg Gly Pro Arg Leu Gln Pro Ala Glu Val Phe Glu Lys Val
    1370                1375                1380

Arg Val Gln Cys Gly
    1385

<210> SEQ ID NO 21
<211> LENGTH: 8
<212> TYPE: PRT
<213> ORGANISM: Artificial Sequence
<220> FEATURE:
<223> OTHER INFORMATION: sequence of fusion domain
<220> FEATURE:
<221> NAME/KEY: VARIANT
<222> LOCATION: (3)..(3)
<223> OTHER INFORMATION: X at residue 3 can be any amino acid residue
<220> FEATURE:
<221> NAME/KEY: VARIANT
<222> LOCATION: (8)..(8)
<223> OTHER INFORMATION: X at residue 8 is an amino acid residue other
      than a leucine residue

<400> SEQUENCE: 21

Arg Ser Xaa Ile Glu Asp Leu Xaa
1               5

<210> SEQ ID NO 22
<211> LENGTH: 8
<212> TYPE: PRT
<213> ORGANISM: Artificial Sequence
<220> FEATURE:
<223> OTHER INFORMATION: sequence of fusion domain
<220> FEATURE:
<221> NAME/KEY: VARIANT
<222> LOCATION: (3)..(3)
<223> OTHER INFORMATION: X at residue 3 can be any amino acid residue
<220> FEATURE:
```

```
<221> NAME/KEY: VARIANT
<222> LOCATION: (7)..(7)
<223> OTHER INFORMATION: X at residue 7 is an amino acid residue other
      than a leucine residue

<400> SEQUENCE: 22

Arg Ser Xaa Ile Glu Asp Xaa Leu
1               5

<210> SEQ ID NO 23
<211> LENGTH: 8
<212> TYPE: PRT
<213> ORGANISM: Artificial Sequence
<220> FEATURE:
<223> OTHER INFORMATION: sequence of fusion domain
<220> FEATURE:
<221> NAME/KEY: VARIANT
<222> LOCATION: (3)..(3)
<223> OTHER INFORMATION: X at residue 3 can be any amino acid residue

<400> SEQUENCE: 23

Arg Ser Xaa Ile Glu Asp Leu Ala
1               5

<210> SEQ ID NO 24
<211> LENGTH: 8
<212> TYPE: PRT
<213> ORGANISM: Artificial Sequence
<220> FEATURE:
<223> OTHER INFORMATION: sequence of fusion domain
<220> FEATURE:
<221> NAME/KEY: VARIANT
<222> LOCATION: (3)..(3)
<223> OTHER INFORMATION: X at residue 3 can be any amino acid residue

<400> SEQUENCE: 24

Arg Ser Xaa Ile Glu Asp Ala Leu
1               5

<210> SEQ ID NO 25
<211> LENGTH: 8
<212> TYPE: PRT
<213> ORGANISM: Artificial Sequence
<220> FEATURE:
<223> OTHER INFORMATION: sequence of fusion domain
<220> FEATURE:
<221> NAME/KEY: VARIANT
<222> LOCATION: (3)..(3)
<223> OTHER INFORMATION: X at residue 3 can be any amino acid residue

<400> SEQUENCE: 25

Arg Ser Xaa Ile Glu Asp Ala Ala
1               5

<210> SEQ ID NO 26
<211> LENGTH: 10
<212> TYPE: PRT
<213> ORGANISM: Artificial Sequence
<220> FEATURE:
<223> OTHER INFORMATION: sequence of retention domain
<220> FEATURE:
<221> NAME/KEY: VARIANT
<222> LOCATION: (1)..(1)
<223> OTHER INFORMATION: X at residue 1 is an amino acid residue other
      than a tyrosine residue
<220> FEATURE:
<221> NAME/KEY: VARIANT
<222> LOCATION: (2)..(2)
<223> OTHER INFORMATION: X at residue 2 can be any amino acid residue
<220> FEATURE:
<221> NAME/KEY: VARIANT
```

```
<222> LOCATION: (3)..(3)
<223> OTHER INFORMATION: X at residue 3 can be any amino acid residue
<220> FEATURE:
<221> NAME/KEY: VARIANT
<222> LOCATION: (5)..(5)
<223> OTHER INFORMATION: X at residue 5 can be any amino acid residue
<220> FEATURE:
<221> NAME/KEY: VARIANT
<222> LOCATION: (7)..(7)
<223> OTHER INFORMATION: X at residue 7 can be any amino acid residue
<220> FEATURE:
<221> NAME/KEY: VARIANT
<222> LOCATION: (9)..(9)
<223> OTHER INFORMATION: X at residue 9 can be any amino acid residue
<220> FEATURE:
<221> NAME/KEY: VARIANT
<222> LOCATION: (10)..(10)
<223> OTHER INFORMATION: X at residue 10 can be any amino acid residue

<400> SEQUENCE: 26

Xaa Xaa Xaa Phe Xaa Lys Xaa His Xaa Xaa
1               5                   10

<210> SEQ ID NO 27
<211> LENGTH: 10
<212> TYPE: PRT
<213> ORGANISM: Artificial Sequence
<220> FEATURE:
<223> OTHER INFORMATION: sequence of retention domain
<220> FEATURE:
<221> NAME/KEY: VARIANT
<222> LOCATION: (2)..(2)
<223> OTHER INFORMATION: X at residue 2 can be any amino acid residue
<220> FEATURE:
<221> NAME/KEY: VARIANT
<222> LOCATION: (3)..(3)
<223> OTHER INFORMATION: X at residue 3 can be any amino acid residue
<220> FEATURE:
<221> NAME/KEY: VARIANT
<222> LOCATION: (5)..(5)
<223> OTHER INFORMATION: X at residue 5 can be any amino acid residue
<220> FEATURE:
<221> NAME/KEY: VARIANT
<222> LOCATION: (7)..(7)
<223> OTHER INFORMATION: X at residue 7 can be any amino acid residue
<220> FEATURE:
<221> NAME/KEY: VARIANT
<222> LOCATION: (8)..(8)
<223> OTHER INFORMATION: X at residue 8 is an amino acid residue other
      than a histidine residue
<220> FEATURE:
<221> NAME/KEY: VARIANT
<222> LOCATION: (9)..(9)
<223> OTHER INFORMATION: X at residue 9 can be any amino acid residue
<220> FEATURE:
<221> NAME/KEY: VARIANT
<222> LOCATION: (10)..(10)
<223> OTHER INFORMATION: X at residue 10 can be any amino acid residue

<400> SEQUENCE: 27

Tyr Xaa Xaa Phe Xaa Lys Xaa Xaa Xaa Xaa
1               5                   10

<210> SEQ ID NO 28
<211> LENGTH: 10
<212> TYPE: PRT
<213> ORGANISM: Artificial Sequence
<220> FEATURE:
<223> OTHER INFORMATION: sequence of retention domain
<220> FEATURE:
<221> NAME/KEY: VARIANT
<222> LOCATION: (2)..(2)
<223> OTHER INFORMATION: X at residue 2 can be any amino acid residue
<220> FEATURE:
<221> NAME/KEY: VARIANT
```

```
<222> LOCATION: (3)..(3)
<223> OTHER INFORMATION: X at residue 3 can be any amino acid residue
<220> FEATURE:
<221> NAME/KEY: VARIANT
<222>

```
<223> OTHER INFORMATION: X at residue 5 can be any amino acid residue
<220> FEATURE:
<221> NAME/KEY: VARIANT
<222> LOCATION: (7)..(7)
<223> OTHER INFORMATION: X at residue 7 can be any amino acid residue
<220> FEATURE:
<221> NAME/KEY: VARIANT
<222> LOCATION: (9)..(9)
<223> OTHER INFORMATION: X at residue 9 can be any amino acid residue
<220> FEATURE:
<221> NAME/KEY: VARIANT
<222> LOCATION: (10)..(10)
<223> OTHER INFORMATION: X at residue 10 can be any amino acid residue

<400> SEQUENCE: 30

Ala Xaa Xaa Phe Xaa Lys Xaa Arg Xaa Xaa
1               5                   10

<210> SEQ ID NO 31
<211> LENGTH: 8
<212> TYPE: PRT
<213> ORGANISM: Artificial Sequence
<220> FEATURE:
<223> OTHER INFORMATION: sequence of fusion domain
<220> FEATURE:
<221> NAME/KEY: VARIANT
<222> LOCATION: (3)..(3)
<223> OTHER INFORMATION: X at residue 3 can be any amino acid residue

<400> SEQUENCE: 31

Arg Ser Xaa Ile Glu Asp Leu Gly
1               5

<210> SEQ ID NO 32
<211> LENGTH: 8
<212> TYPE: PRT
<213> ORGANISM: Artificial Sequence
<220> FEATURE:
<223> OTHER INFORMATION: sequence of retention domain
<220> FEATURE:
<221> NAME/KEY: VARIANT
<222> LOCATION: (3)..(3)
<223> OTHER INFORMATION: X at residue 3 can be any amino acid residue

<400> SEQUENCE: 32

Arg Ser Xaa Ile Glu Asp Gly Leu
1               5

<210> SEQ ID NO 33
<211> LENGTH: 8
<212> TYPE: PRT
<213> ORGANISM: Artificial Sequence
<220> FEATURE:
<223> OTHER INFORMATION: sequence of fusion domain
<220> FEATURE:
<221> NAME/KEY: VARIANT
<222> LOCATION: (3)..(3)
<223> OTHER INFORMATION: X at residue 3 can be any amino acid residue

<400> SEQUENCE: 33

Arg Ser Xaa Ile Glu Asp Gly Gly
1               5

<210> SEQ ID NO 34
<211> LENGTH: 8
<212> TYPE: PRT
<213> ORGANISM: Artificial Sequence
<220> FEATURE:
<223> OTHER INFORMATION: sequence of fusion domain
<220> FEATURE:
<221> NAME/KEY: VARIANT
```

```
<222> LOCATION: (3)..(3)
<223> OTHER INFORMATION: X at residue 3 can be any amino acid residue

<400> SEQUENCE: 34

Arg Ser Xaa Ile Glu Asp Gly Ala
1               5

<210> SEQ ID NO 35
<211> LENGTH: 8
<212> TYPE: PRT
<213> ORGANISM: Artificial Sequence
<220> FEATURE:
<223> OTHER INFORMATION: sequence of fusion domain
<220> FEATURE:
<221> NAME/KEY: VARIANT
<222> LOCATION: (3)..(3)
<223> OTHER INFORMATION: X at residue 3 can be any amino acid residue

<400> SEQUENCE: 35

Arg Ser Xaa Ile Glu Asp Ala Gly
1               5

<210> SEQ ID NO 36
<211> LENGTH: 5153
<212> TYPE: DNA
<213> ORGANISM: Artificial Sequence
<220> FEATURE:
<223> OTHER INFORMATION: PEDV spike protein encoding cassette

<400> SEQUENCE: 36
ccgcggtaat cggaaggaca gtggtattac tctgggctca aaaggtcaac tattgagaga      60
cctccagctg aaacccattg acaaagagtc tagctcggca atcggataca aaccaaagga     120
taccgcacct tctaaagctg tacttgcatc attgatcaga tcaagcagag ttgatcaaag     180
tcacaaacat aacatgctgg ttctgcttaa aaatatcaag ggagatgaca acctaaacga     240
gttctaccag atggtcaaga gtattactca tgcttaatct gtagcgttga ctaatctact     300
aaccggcgca aaactgcttt cactatcgct taaaagcaat tataaaaaac ttaggactca     360
ggtagtccag cagcaccatg aaatccctca actacttctg gctcttcctc cccgtgctct     420
ccaccctcag cctccctcag gatgtcacaa gatgccagtc cacaatcaac ttcagacggt     480
tcttctccaa gttcaacgtg caggcccccg ccgtggtggt gctgggcggc tacctgccaa     540
gcatgaactc cagctcctgg tactgcggca ccggcctgga ccgcctcc ggcgtgcacg     600 gcatcttcct gagctacatc gacgccggcc agggcttcga gatcggcatc agccaggagc     660
ccttcgaccc aagcggctac cagctgtacc tgcacaaggc caccaacggc aaccacaacg     720
ccatcgccag gctgagaatc tgccagttcc ccaacaacaa gaccctgggc cccaccgtga     780
acgacgtgac caccggcaga aactgcctgt caacaaggc catcccagcc tacatgcagg     840
acggcaagaa catcgtggtg ggcatcacct gggacaacga cagagtgacc gtgttcgccg     900
acaagatcta ccacttctac ctgaagaacg actggtccag agtggccacc aggtgctaca     960
acaagcggag ctgcgccatg cagtacgtgt acacccccaa ctactacatg ctgaacgtga    1020
ccagcgccgg cgaggacggc atctactacg agccctgcac cgccaactgc agcggctacg    1080
ccgtgaacgt gttcgccacc gacagcaacg gccacatccc cgagggcttc tccttcaaca    1140
actggttcct gctgagcaac gactccaccc tgctgcacgg caaggtggtg tccaaccagc    1200
cactgctggt gaactgcctg ctggccatcc aaagatcta cggcctgggc cagttcttca    1260
gcttcaacca gaccatggac ggcgtgtgca acggcgccgc cgcccagagg gccccagagg    1320
```

```
ccctgagatt caacatcaac gacacctccg tgatcctggc cgagggcagc atcgtgctgc    1380
acaccgccct gggcaccaac ctgagcttcg tgtgctccaa cagctccgac ccccacctgg    1440
ccaccttcac catcccactg ggcgccaccc aggtgccata ctactgcttc ctgaaggtgg    1500
acacctacaa cagcaacgtg tacaagttcc tggccgtgct gccacccacc gtgagagaga    1560
tcgtgatcac caagtacggc gacgtgtacg tgaacggctt cggctacctg cacctgggcc    1620
tgctggacgc cgtgaccatc aacttcaccg gccacggcac cgacgacgac gtgagcggct    1680
tctggaccat cgcctccacc aacttcgtgg acgccctgat cgaggtgcag ggcaccgcca    1740
tccagcgcat cctgtactgc gacgacccag tgtcccagct gaagtgcagc caggtggcct    1800
tcgacctgga cgacggcttc tacccccatca gctccagaaa cctgctgagc cacgagcagc    1860
caatcagctt cgtgaccctg ccatccttca cgaccactc cttcgtgaac atcaccgtga    1920
gcgcctcctt cggcggccac tccggcgcca acctgatcgc ctccgacacc accatcaacg    1980
gcttctccag cttctgcgtg gacaccaggc agttcaccat cagcctgttc tacaacgtga    2040
ccaacagcta cggctacgtg agcaagagcc aggactccaa ctgccccttc accctgcagt    2100
ccgtgaacga ctacctgtcc ttcagcaagt ctgcgtgtc caccagcctg ctggccagcg    2160
cctgcaccat cgacctgttc ggctacccag agttcggctc cggcgtgaag ttcaccagcc    2220
tgtacttcca gttcaccgag ggcgagctga tcaccggcac cccaaagccc ctggagggcg    2280
tgaccgacgt gagcttcatg acccctggacg tgtgcaccaa gtacaccatc tacggcttca    2340
agggcgaggg catcatcacc ctgaccaaca gctccttcct ggccggcgtg tactacacct    2400
ccgacagcgc ccagctgctg gccttcaaga acgtgacctc cggcgccgtg tacagcgtga    2460
ccccctgctc cttcagcgag caggccgcct acgtggacga cgacatcgtg ggcgtgatct    2520
ccagcctgtc ctccagcacc ttcaactcca ccagagagct gccaggcttc ttctaccaca    2580
gcaacgacgg ctccaactgc accgagccag tgctggtgta ctccaacatc ggcgtgtgca    2640
agagcggctc catcggctac gtgccatccc agagcggcca ggtgaagatc gccccaccg    2700 tgaccggcaa catctccatc cccaccaact tctccatgag catcagaacc gagtacctgc    2760
agctgtacaa caccccgtg tccgtggact gcgccaccta cgtgtgcaac ggcaactcca    2820
gatgcaagca gctgctgacc cagtacaccg ccgcctgcaa gaccatcgag agcgccctgc    2880
agctgagcgc caggctggag tccgtggagg tgaacagcat gctgaccatc tccgaggagg    2940
ccctgcagct ggccaccatc agctccttca acggcgacgg ctacaacttc accaacgtgc    3000
tgggcgtgag cgtgtacgac ccagccagcg gcagagtggt gcagaagagg agcttcatcg    3060
aggacgccgc cttcaacaag gtggtgacca acggcctggg caccgtggac gaggactaca    3120
agagatgcag caacggcaga tccgtggccg acctggtgtg cgcccagtat tacagcggcg    3180
tgatggtgct gccaggcgtg gtggacgccg agaagctgca catgtacagc gcctccctga    3240
tcggcggcat ggtgctgggc ggcttcacct ccgccgccgc cctgcccttc agctacgccg    3300
tgcaggccag actgaactac ctggccctgc agaccgacgt gctgcagaga aaccagcagc    3360
tgctggccga gagcttcaac agcgccatcg gcaacatcac ctccgccttc gagagcgtga    3420
aggaggccat cagccagacc tccaagggcc tgaacaccgt ggcccacgcc ctgaccaagg    3480
tgcaggaggt ggtgaactcc cagggcgccg ccctgaccca gctgaccgtg cagctgcagc    3540
acaacttcca ggccatctcc agctccatcg acgacatcta ctccaggctg gacatcctgt    3600
ccgccgacgt gcaggtggac agactgatca ccggcagact gtccgccctg aacgccttcg    3660
tggcccagac cctgaccaag tacaccgagg tgcaggcctc cagaaagctg gcccagcaga    3720
```

```
aggtgaacga gtgcgtgaag tcccagagcc agagatacgg cttctgcggc ggcgacggcg    3780
agcacatctt ctccctggtg caggccgccc acagggcct gctgttcctg cacaccgtgc     3840
tggtgccagg cgacttcatc gacgtgatcg ccatcgccgg cctgtgcgtg aacgacgaga    3900
tcgccctgac cctgagagag cccggcctgg tgctgttcac ccacgagctg cagaaccaca    3960
ccgccaccga gtatttcgtg agctccagac ggatgttcga gccaagaaag cccaccgtga    4020
gcgacttcgt gcagatcgag tcctgcgtgg tgacctacgt gaacctgacc agagaccagc    4080
tgccagacgt gatcccagac tacatcgacg tgaacaagac cctggacgag atcctggcct    4140
ccctgccaaa cagaaccggc cccagcctgc ccctggacgt gttcaacgcc acctacctga    4200
acctgaccgg cgagatcgcc gacctggagc agagaagcga gtccctgaga acaccaccg     4260
aggagctgca gtccctgatc tacaacatca acaacccct ggtggacctg gagtggctga     4320
acagagtgga gacctacatc aagtggccat ggtgggtgtg gctgatcgtg ttcatcgtgc    4380
tgatcttcgt ggtgtccctg ctggtgttct gctgcatctc caccggctgc tgcggctgct    4440
gcggctgctg ctgcgcctgc ttcagcggct gctgtagagg accccggctc cagcccgctg    4500
aggtgtttga gaaagtgaga gtgcagtgat aaatattcaa gaccagtcct gcatcagtca    4560
acaattatca ttctaaactc attataaaaa acttaggaca caagagccta agtcctctcc    4620
taaaaaatga ctgaggtgta cgacttcgat cagtcttctt gggacaccaa gggcttattg    4680
gcccctattt tgcctaccac ttatcccgat ggtaggctca taccccaagt cagagtaata    4740
gatccaggac tcggcgatag gaaagatgaa tgcttcatgt atatttttct actgggtata    4800
atagaagaca atgatggcct cggaccccca attggaagaa catttggatt gctgcctttg    4860
ggagttgggc gtactacagc cagacctgag gagttattga agaagccac cctgttggat     4920
attgtggtaa ggcgaactgc aggtgtcaag gaacaactgg tattttataa taacacccca    4980
ttgcacatct taactccgtg gaaaaaggtc cttacgagtg gaagtgtgtt cagtgcaaat    5040
caagtctgta acgcagtcaa tctaatacca ttagacatag cacaaagatt cagggtggta    5100
tatatgagca tcactcgact atcagacgat ggaagttaca gaattccccg cgg          5153
```

<210> SEQ ID NO 37
<211> LENGTH: 4155
<212> TYPE: RNA
<213> ORGANISM: Artificial Sequence
<220> FEATURE:
<223> OTHER INFORMATION: encodes a PEDV S protein

<400> SEQUENCE: 37

```
uuaucacugc acucucacuu ucucaaacac ucagcgggc uggagccggg guccucuaca      60
gcagccgcug aagcaggcgc agcagcagcc gcagcagccg cagcagccgg uggagaugca    120
gcagaacacc agcagggaca ccacgaagau cagcacgaug aacacgauca gccacaccca    180
ccauggccac uugauguagg ucccacucu guucagccac uccaggucca ccaggguguu     240
guugauguug uagaucaggg acugcagcuc ucggugguug uuucucaggg acucgcuucu    300
cugcuccagg ucggcgaucu cgccggucag guucagguag guggcguuga acacguccag    360
gggcaggcug gggccgguuc uguuuggcag ggaggccagg aucucgucca ggucuugguu    420
cacgucgaug uagucuggga ucacgucugg cagcuggucu cuggucaggu ucacguaggu    480
caccacgcag gacucgaucu gcacgaaguc gcucacggug ggcuucuug gcucgaacau    540
ccgucuggag cucacgaaau acucggggc ggugugguuc ugcagcucgu ggugugaacag     600
```

-continued

```
caccaggccg ggcucucuca ggglucagggc gaucucgucg uucacgcaca ggccggcgau    660
ggcgaucacg ucgaugaagu cgccuggcac cagcacggug ugcaggaaca gcaggcccug    720
uggggcggcc ugcaccaggg agaagaugug cucgccgucg ccgccgcaga agccguaucu    780
cuggcucugg gacuucacgc acucguucac cuucugcugg gccagcuuuc uggaggccug    840
caccucggug uacuugguca gggucugggc cacgaaggcg uucagggcgg acagucugcc    900
ggugaucagu cugucccaccu gcacgucggc ggacaggaug uccagccugg aguagaugu    c960 gucgauggag cuggagaugg ccuggaaguu gugcugcagc ugcacgguca gcugggucag   1020
ggcggcgccc uggagguuca ccaccuccug caccuuggluc agggcguggg ccacggluguu   1080 caggcccuug gaggucluggc ugauggccuc cuucacgcuc ucgaaggcgg aggugauguu   1140
gccgauggcg cuguugaagc ucucggccag cagcugcugg uuucucugca gcacgucggu   1200
cugcagggcc agguaguuca gucluggccug cacggcguag cugaagggca gggcggcggc   1260
ggaggugaag ccgcccagca ccaugccgcc gaucagggag gcgcuguaca ugugcagcuu   1320
cucggcguuc accacgccug gcagcaccau cacgccgcug uaauacuggg cgcacaccag   1380
gucggccacg gaucugccgu ugcugcaucu cuguagucc ucuccacgg ugcccaggcc    1440 guuggucacc accuuguuga aggcggcguc cucgaugaag cuccucuucu gcaccacucu   1500
gccgcuggcu ggucguaca cgcucacgcc cagcacgulug ugaaguugu agccgucgcc    1560 guugaaggag cugaugguggg ccagcluggcag ggccluccucg gagauggluca gcaugcuguu   1620 caccuccacg gacuccagcc uggcgcucag cugcagggcg cucucgaugg ucuugcaggc   1680 ggcguguac uggucagca gcugcuugca ucggaguug ccguugcaca cguaggugc     1740 gcaguccacg gacacggggg uguugluacag cugcagguac ucgguucuga ugcucaugga   1800
gaaguuggug gggauggaga guugccggu cacggugggg gcgaucuuca ccuggccgcu    1860
cugggauggc acguagccga uggagccgcu cuugcacacg ccgauguugg aguacaccag   1920
cacuggcucg gugcaguugg agccgucguu cugcugguag aagaagccug gcagcucucu   1980
gguggaguug aaggugcugg aggacaggcu ggagaucacg cccacgaugu cgucguccac   2040
guaggcggcc ugclucgcuga aggagcaggg ggucacgcug uacacggcgc cggaggulcac    2100 guucuugaag gccagcagcu ggccgcuguc ggagguguag uacacgccgg ccaggaagga   2160 gcuguuggluc agggugauga ugcccucgcc cuugaagccg uagauggugu acuuggugca   2220
cacguccagg ucaugaagc ucacgucggu cacgcccucc agggggcuuug ggugccggu    2280 gaucagcucg cccucgguga acuggaagua caggcuggga aacuuacgc cggagccgaa   2340 cucugggluag ccgaacaggu cgauggugca ggcgcuggcc agcaggclugg uggacacgca   2400 gaacuugcug aaggacaggu agucguucac ggacugcagg ugaagggglc aguggaguc     2460 cluggcluculug cucacguagc cguagcugulu ggucacguug uagaacaggc ugauggugaa   2520 cugccluggug uccacgcaga agcluggagaa gccguugalug ugglugucgg aggcgaucag    2580 guuggcgccg gagluggccgc cgaaggaggc gclucacgglug auguucacga aggagglugguc   2640 guugaaggau ggcagggluca cgaagcugau uggculgcucg uggcucagca gguuucugga    2700 gclugaugggg uagaagccgu cguccagguc gaaggccacc uggcluglgcacu ucaglcluggga   2760 cacugggulcg ucgcaguaca ggaugcgcug gauggcggug cccluglgcaccu cgaucagggc   2820 guccacgaag uuggluggagg cgaulgglucca gaagccgcuc acglucglucglu cgglugccglug   2880 gccglglgaag uugaulgglulca cggcglucag cagglcccagg ulgcagglulagc cgaagccgluu   2940 cacguacacg ucgccgulaclu ugglugaulcac galulcucuclu acgglugggglu gcagcacggc   3000
```

| | |
|---|---:|
| caggaacuug uacacguugc uguuguaggu guccaccuuc aggaagcagu aguauggcac | 3060 |
| cuggguggcg cccagugggn uggugaaggu ggccaggugg gggucggagc uguuggagca | 3120 |
| cacgaagcuc agguugguge ccagggcggu gugcagcacg augcugcccu cggccaggau | 3180 |
| cacggaggug ucguugaugu ugaaucucag ggccucuggg gcccucuggg cggcggcgcc | 3240 |
| guugcacacg ccguccaugg ucugguugaa gcugaagaac uggcccaggc cguagaucuu | 3300 |
| ugggauggcc agcaggcagu ucaccagcag uggcugguug acaccaccu ugccgugcag | 3360 |
| cagggugag ucguugcuca gcaggaacca guuguugaag gagaagcccu cggggaugug | 3420 |
| gccguucug ucgguggcga acacguucac ggcguagccg cugcaguugg cggugcaggg | 3480 |
| cucguaguag augccguccu cgccggcgcu ggucacguuc agcauguagu agguuggggu | 3540 |
| guacacguac ugcauggcgc agcuccgcuu guuguagcac cugguggcca cucuggacca | 3600 |
| gucguucuuc agguagaagu gguagaucuu gucggcgaac acggucacuc ugucguuguc | 3660 |
| ccaggugaug cccaccacga uguucuugcc guccugcaug uaggcuggga uggccuuguu | 3720 |
| gaacaggcag uuucugccgg uggucacguc guucacgguc gggcccaggg ucuguuguu | 3780 |
| ggggaacugg cagauucuca gccuggcgau ggcguugugg uugccguugg uggccuugug | 3840 |
| cagguacagc ugguagccgc uugggucgaa gggcuccugg cugaugccga ucucgaagcc | 3900 |
| cuggccggcg ucgauguagc ucaggaagau gccgugcacg ccggaggcgg ucuccaggcc | 3960 |
| ggugccgcag uaccaggagc uggaguucau gcuuggcagg uagccgccca gcaccaccac | 4020 |
| ggcgggggcc ugcacguuga acuuggagaa gaaccgucug aaguugauug uggacuggca | 4080 |
| ucuugugaca uccugaggga ggcugagggu ggagagcacg ggaggaaga gccagaagua | 4140 |
| guugagggau uucau | 4155 |

<210> SEQ ID NO 38
<211> LENGTH: 4245
<212> TYPE: RNA
<213> ORGANISM: Artificial Sequence
<220> FEATURE:
<223> OTHER INFORMATION: comprises a sequence encoding a PEDV S protein

<400> SEQUENCE: 38

| | |
|---|---:|
| aaguuuuuua uaaugaguuu agaaugauaa uuguugacug augcaggacu ggucuugaau | 60 |
| auuuaucacu gcacucucac uuucucaaac accucagcgg gcuggagccg ggguccucua | 120 |
| cagcagccgc ugaagcaggc gcagcagcag ccgcagcagc cgcagcagcc gguggagaug | 180 |
| cagcagaaca ccagcaggga caccacgaag aucagcacga ugaacacgau cagccacacc | 240 |
| caccauggcc acuugaugua ggucuccacu cguucagcc acuccagguc caccagggug | 300 |
| uuguugaugu guagaucag ggacugcagc uccgcgugg uguuucucag ggacucgcuu | 360 |
| cucugcucca ggucggcgau cucgccgguc agguucaggu agguggcguu gaacacgucc | 420 |
| aggggcaggc uggggccggu ucuguuuggc agggaggcca ggaucucguc cagggucuug | 480 |
| uucacgucga uguagucugg gaucacgucu ggcagcuggu cucggucag guucacguag | 540 |
| gucaccacgc aggacucgau cugcacgaag ucgcucacgg ugggcuuucu uggcucgaac | 600 |
| auccgucugg agcucacgaa auacgggug gcggguggg ucugcagcuc guggguguaac | 660 |
| agcaccaggc cgggcucucu cagggucagg gcgaucucgu cguucacgca caggccggcg | 720 |
| auggcgauca cgucgaugaa gucgccugge accagcacgg ugcaggaa cagcaggccc | 780 |
| ugugggggcgg ccugcaccag ggagaagaug ugcucgccgu cgccgccgca gaagccguau | 840 |

```
cucuggcucu gggacuucac gcacucguuc accuucugcu gggccagcuu ucuggaggcc    900
ugcaccucgg uguacuuggu cagggucugg gccacgaagg cguucagggc ggacagucug    960
ccggugauca gucuguccac cugcacgucg gcggacagga uguccagccu ggaguagaug   1020
ucgucgaugg agcuggagau ggccuggaag uugugcugca gcugcacggu cagcuggguc   1080
agggcggcgc ccugggaguu caccaccucc ugcaccuugg ucagggcgug ggccacggug   1140
uucaggcccu uggaggucug gcugauggcc uccuucacgc ucgaaggc ggaggugaug    1200 uugccgaugg cgcuguugaa gcucucggcc agcagcugcu gguuucucug cagcacgucg   1260
gucugcaggg ccagguaguu cagucuggcc ugcacggcgu agcugaaggg cagggcggcg   1320
gcggagguga agccgcccag caccaugccg ccgaucaggg aggcgcugua caugugcagc   1380 uucucgcgu ccaccacgcc uggcagcacc aucacgccgc uguaauacug ggcgcacacc    1440
aggucggcca cggaucugcc guugcugcau ucuuguagu ccucguccac ggugcccagg    1500
ccguugguca ccaccuuguu gaaggcggcg uccucgauga agcuccucuu cugcaccacu   1560
cugccgcugg cugggucgua cacgcucacg cccagcacgu uggugaaguu guagccgucg   1620
ccguugaagg agcugauggu ggccagcugc agggccuccu cggagauggu cagcaugcug   1680
uucaccucca cggacuccag ccuggcgcuc agcugcaggg cgcucgau ggucuugcag    1740 gcggcgugu acugggucag cagcugcuug caucuggagu ugccguugca cacguaggug   1800
gcgcagucca cggacacggg ggugugac agcugcaggu acucgguucu gaugcucaug    1860
gagaaguugg uggggaugga gauguugccg gucacgguug gggcgaucuu caccuggccg   1920
cucugggaug gcacguagcc gauggagccg cucuugcaca cgccgauguu ggaguacacc   1980
agcacuggcu cggugcaguu ggagccgucg uugcuguggu agaagaagcc uggcagcucu   2040
cugguggagu ugaaggugcu ggaggacagg cuggagauca cgcccacgau gucgucgucc   2100
acguaggcgg ccugcucgcu gaaggagcag ggggucacgc uguacacggc gccggagguc   2160
acguucuuga aggccagcag cuggccgcug ucggagugu aguacacgcc ggccaggaag    2220
gagcuguugg ucagggugau gaugcccucg cccuugaagc cguagauggu guacuuggug   2280
cacacgucca gggucaugaa gcucacgucg gucacgcccu caggggcuu uggggugccg    2340 gugaucagcu cgcccucggu gaacuggaag uacaggcugg ugaacuucac gccggagccg   2400 aacucuigggu agccgaacag gucgauggug caggcgcugg ccagcaggcu gguggacacg   2460
cagaacuugc ugaaggacag guagucguuc acggacugca gggugaaggg gcaguuggag   2520
uccuggcucu ugcucacgua gccguagcug uggucacgu uguagaacag gcugauggug    2580
aacugccugg uguccacgca gaagcuggag aagccguuga uggugugguc ggaggcgauc   2640
agguuggcgc cggaguggcc gccgaaggag gcgcucacgg ugauguucac gaaggagugg   2700
ucguugaagg auggcagggu cacgaagcug auuggcugcu cguggcucag cagguuucug   2760
gagcugaugg gguagaagcc gucguccagg ucgaaggcca ccuggcugca cuucagcugg   2820
gacacugggu cgucgcagua cagga ugcgc uggauggcgg ugcccugcac cucgaucagg   2880
gcguccacga aguuggugga ggcgauggu cagaagccgc ucacgucguc gucggugccg    2940
uggccgguga aguugauggu cacgcgucc agcaggccca ggucaggua ccgaagccg     3000 uucacguaca cgucgccgua cuuggugauc acgaucucuc ucacgguggg uggcagcacg   3060
gccaggaacu uguacacguu gcuguuguag guguccaccu ucaggaagca guaguauggc   3120
accuggugug cgcccagugg gauggugaag gguggccaggu ggggucgga gcuguuggag    3180 cacacgaagc ucaguugguu gcccagggcg gugugcagca cgaugcugcc cucggccagg   3240
```

```
aucacggagg ugucguugau guugaaucuc agggccucug ggcccucug ggcggcggcg    3300 ccguugcaca cgccguccau ggucuggung aagcugaaga acuggccag gccguagauc    3360 uuugggaugg ccagcaggca guucaccagc aguggcuggu uggacaccac cuugccguc    3420 agcagggugg agucguugcu cagcaggaac caguuguuga aggagaagcc cucggggaug    3480
uggccguugc ugucggugc gaacacguuc acggcguagc cgcugcaguu ggcggugcag    3540
ggcucguagu agaugccguc cucgccggcg cuggucacgu ucagcaugua guagguuggg    3600
guguacacgu acugcauggc gcagcuccgu uguuguagc accuggugc cacucuggac    3660 cagucguucu ucagguagaa guggagauc uugucggcga acacggucac ucugucguug    3720
ucccagguga ugcccaccac gauguucuug ccguccugca guaggcugg gauggccuug    3780 uugaacaggc aguucugcc gguggucacg ucguucacgg uggggcccag ggucuuguug    3840
uuggggaacu ggcagauucu cagccuggcg auggcguugu ggungccguu gguggccuug    3900
ugcagguaca gcuggagcc gcuugggucg aagggcuccu ggcugaugcc gaucucgaag    3960
cccuggccgg cgucgaugua gcucaggaag augccgugca cgccggaggc ggucuccagg    4020
ccggugccgc aguaccagga gcuggaguuc augcuuggca gguagccgcc cagcaccacc    4080
acggcggggg ccugcacguu gaacuuggag aagaaccguc ugaaguugau guggacugg    4140 caucuuguga cauccugagg gaggcugagg guggagagca cggggaggaa gagccagaag    4200
uaguugaggg auuucauggu gcucuggac uaccugaguc cuaag                    4245
```

<210> SEQ ID NO 39
<211> LENGTH: 1386
<212> TYPE: PRT
<213> ORGANISM: porcine epidemic diarrhea virus

<400> SEQUENCE: 39

```
Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Asn Thr Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ile Gly Glu Asn Gln Gly Val Asn Ser Thr
    50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
            100                 105                 110

Thr Asn Gly Asn Thr Asn Ala Thr Ala Arg Leu Arg Ile Cys Gln Phe
        115                 120                 125

Pro Ser Ile Lys Thr Leu Gly Pro Thr Ala Asn Asn Asp Val Thr Thr
    130                 135                 140

Gly Arg Asn Cys Leu Phe Asn Lys Ala Ile Pro Ala Tyr Met Ser Glu
145                 150                 155                 160

His Ser Val Val Gly Ile Thr Trp Asp Asn Asp Arg Val Thr Val Phe
                165                 170                 175

Ser Asp Lys Ile Tyr Tyr Phe Tyr Phe Lys Asn Asp Trp Ser Arg Val
            180                 185                 190
```

```
Ala Thr Lys Cys Tyr Asn Ser Gly Gly Cys Ala Met Gln Tyr Val Tyr
            195                 200                 205

Glu Pro Thr Tyr Tyr Met Leu Asn Val Thr Ser Ala Gly Glu Asp Gly
210                 215                 220

Ile Ser Tyr Gln Pro Cys Thr Ala Asn Cys Ile Gly Tyr Ala Ala Asn
225                 230                 235                 240

Val Phe Ala Thr Glu Pro Asn Gly His Ile Pro Glu Gly Phe Ser Phe
            245                 250                 255

Asn Asn Trp Phe Leu Leu Ser Asn Asp Ser Thr Leu Val His Gly Lys
            260                 265                 270

Val Val Ser Asn Gln Pro Leu Leu Val Asn Cys Leu Leu Ala Ile Pro
            275                 280                 285

Lys Ile Tyr Gly Leu Gly Gln Phe Phe Ser Phe Asn Gln Thr Ile Asp
            290                 295                 300

Gly Val Cys Asn Gly Ala Ala Val Gln Arg Ala Pro Glu Ala Leu Arg
305                 310                 315                 320

Phe Asn Ile Asn Asp Thr Ser Val Ile Leu Ala Glu Gly Ser Ile Val
                325                 330                 335

Leu His Thr Ala Leu Gly Thr Asn Phe Ser Phe Val Cys Ser Asn Ser
            340                 345                 350

Ser Gly Pro His Leu Ala Thr Phe Ala Ile Pro Leu Gly Ala Thr Gln
            355                 360                 365

Val Pro Tyr Tyr Cys Phe Leu Lys Val Asp Thr Tyr Asn Ser Thr Val
            370                 375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
                405                 410                 415

Gly Leu Leu Asp Ala Val Thr Ile Asn Phe Thr Gly His Gly Thr Asp
            420                 425                 430

Gly Asp Val Ser Gly Phe Trp Thr Ile Ala Ser Thr Asn Phe Val Asp
            435                 440                 445

Ala Leu Ile Glu Val Gln Gly Thr Ala Ile Gln Arg Ile Leu Tyr Cys
450                 455                 460

Asp Asp Pro Val Ser Gln Leu Lys Cys Ser Gln Val Ala Phe Asp Leu
465                 470                 475                 480

Asp Asp Gly Phe Tyr Pro Ile Ser Ser Arg Asn Leu Leu Ser His Glu
                485                 490                 495

Gln Pro Ile Ser Phe Val Thr Leu Pro Ser Phe Asn Asp His Ser Phe
            500                 505                 510

Val Asn Ile Thr Val Ser Ala Ser Phe Gly Gly His Ser Gly Ala Asn
            515                 520                 525

Leu Ile Ala Ser Asp Thr Thr Ile Asn Gly Phe Ser Ser Phe Cys Val
            530                 535                 540

Asp Thr Arg Gln Phe Thr Ile Ser Leu Phe Tyr Asn Val Thr Asn Ser
545                 550                 555                 560

Tyr Gly Tyr Val Ser Asn Ser Gln Asp Ser Asn Cys Pro Phe Thr Leu
                565                 570                 575

Gln Ser Val Asn Asp Tyr Leu Ser Phe Ser Lys Phe Cys Val Ser Thr
            580                 585                 590

Ser Leu Leu Ala Ser Ala Cys Thr Ile Asp Leu Phe Gly Tyr Pro Glu
            595                 600                 605

Phe Gly Ser Gly Val Lys Phe Thr Ser Leu Tyr Phe Gln Phe Thr Lys
```

-continued

```
            610                 615                 620
Gly Glu Leu Ile Thr Gly Thr Pro Lys Pro Leu Glu Gly Val Thr Asp
625                 630                 635                 640

Val Ser Phe Met Thr Leu Asp Val Cys Thr Lys Tyr Thr Ile Tyr Gly
                645                 650                 655

Phe Lys Gly Glu Gly Ile Ile Thr Leu Thr Asn Ser Ser Phe Leu Ala
                660                 665                 670

Gly Phe Tyr Tyr Thr Ser Asp Ser Gly Gln Leu Leu Ala Phe Lys Asn
            675                 680                 685

Val Thr Ser Gly Ala Val Tyr Ser Val Thr Pro Cys Ser Phe Ser Glu
        690                 695                 700

Gln Ala Ala Tyr Val Asp Asp Ile Val Gly Val Ile Ser Ser Leu
705                 710                 715                 720

Ser Ser Ser Thr Phe Asn Ser Thr Arg Glu Leu Pro Gly Phe Phe Tyr
                725                 730                 735

His Ser Asn Asp Gly Ser Asn Cys Thr Glu Pro Val Leu Val Tyr Ser
                740                 745                 750

Asn Ile Gly Val Cys Lys Ser Gly Ser Ile Gly Tyr Val Pro Ser Gln
            755                 760                 765

Ser Gly Gln Val Lys Ile Ala Pro Thr Val Thr Gly Asn Ile Ser Ile
770                 775                 780

Pro Thr Asn Phe Ser Met Ser Ile Arg Thr Glu Tyr Leu Gln Leu Tyr
785                 790                 795                 800

Asn Thr Pro Val Ser Val Asp Cys Ala Thr Tyr Val Cys Asn Gly Asn
                805                 810                 815

Ser Arg Cys Lys Gln Leu Leu Thr Gln Tyr Thr Ala Ala Cys Lys Thr
            820                 825                 830

Ile Glu Ser Ala Leu Gln Leu Ser Ala Arg Leu Glu Ser Val Glu Val
        835                 840                 845

Asn Ser Met Leu Thr Ile Ser Glu Glu Ala Leu Gln Leu Ala Thr Ile
    850                 855                 860

Ser Ser Phe Asn Gly Asp Gly Tyr Asn Phe Thr Asn Val Leu Gly Val
865                 870                 875                 880

Ser Val Tyr Asp Pro Ala Ser Gly Arg Val Val Gln Lys Arg Ser Phe
                885                 890                 895

Ile Glu Asp Leu Leu Phe Asn Lys Val Val Thr Asn Gly Leu Gly Thr
            900                 905                 910

Val Asp Glu Asp Tyr Lys Arg Cys Ser Asn Gly Arg Ser Val Ala Asp
        915                 920                 925

Leu Val Cys Ala Gln Tyr Tyr Ser Gly Val Met Val Leu Pro Gly Val
    930                 935                 940

Val Asp Ala Glu Lys Leu His Met Tyr Ser Ala Ser Leu Ile Gly Gly
945                 950                 955                 960

Met Val Leu Gly Gly Phe Thr Ser Ala Ala Ala Leu Pro Phe Ser Tyr
                965                 970                 975

Ala Val Gln Ala Arg Leu Asn Tyr Leu Ala Leu Gln Thr Asp Val Leu
            980                 985                 990

Gln Arg Asn Gln Gln Leu Leu Ala Glu Ser Phe Asn Ser Ala Ile Gly
        995                 1000                1005

Asn Ile Thr Ser Ala Phe Glu Ser Val Lys Glu Ala Ile Ser Gln
    1010                1015                1020

Thr Ser Lys Gly Leu Asn Thr Val Ala His Ala Leu Thr Lys Val
    1025                1030                1035
```

Gln Glu Val Val Asn Ser Gln Gly Ala Ala Leu Thr Gln Leu Thr
    1040                1045                1050

Val Gln Leu Gln His Asn Phe Gln Ala Ile Ser Ser Ile Asp
    1055                1060                1065

Asp Ile Tyr Ser Arg Leu Asp Ile Leu Ser Ala Asp Val Gln Val
    1070                1075                1080

Asp Arg Leu Ile Thr Gly Arg Leu Ser Ala Leu Asn Ala Phe Val
    1085                1090                1095

Ala Gln Thr Leu Thr Lys Tyr Thr Glu Val Gln Ala Ser Arg Lys
    1100                1105                1110

Leu Ala Gln Gln Lys Val Asn Glu Cys Val Lys Ser Gln Ser Gln
    1115                1120                1125

Arg Tyr Gly Phe Cys Gly Gly Asp Gly Glu His Ile Phe Ser Leu
    1130                1135                1140

Val Gln Ala Ala Pro Gln Gly Leu Leu Phe Leu His Thr Val Leu
    1145                1150                1155

Val Pro Gly Asp Phe Val Asp Val Ile Ala Ile Ala Gly Leu Cys
    1160                1165                1170

Val Asn Asp Glu Ile Ala Leu Thr Leu Arg Glu Pro Gly Leu Val
    1175                1180                1185

Leu Phe Thr His Glu Leu Gln Asn His Thr Ala Thr Glu Tyr Phe
    1190                1195                1200

Val Ser Ser Arg Arg Met Phe Glu Pro Arg Lys Pro Thr Val Ser
    1205                1210                1215

Asp Phe Val Gln Ile Glu Ser Cys Val Val Thr Tyr Val Asn Leu
    1220                1225                1230

Thr Arg Asp Gln Leu Pro Asp Val Ile Pro Asp Tyr Ile Asp Val
    1235                1240                1245

Asn Lys Thr Leu Asp Glu Ile Leu Ala Ser Leu Pro Asn Arg Thr
    1250                1255                1260

Gly Pro Ser Leu Pro Leu Asp Val Phe Asn Ala Thr Tyr Leu Asn
    1265                1270                1275

Leu Thr Gly Glu Ile Ala Asp Leu Glu Gln Arg Ser Glu Ser Leu
    1280                1285                1290

Arg Asn Thr Thr Glu Glu Leu Gln Ser Leu Ile Tyr Asn Ile Asn
    1295                1300                1305

Asn Thr Leu Val Asp Leu Glu Trp Leu Asn Arg Val Glu Thr Tyr
    1310                1315                1320

Ile Lys Trp Pro Trp Trp Val Trp Leu Ile Ile Phe Ile Val Leu
    1325                1330                1335

Ile Phe Val Val Ser Leu Leu Val Phe Cys Cys Ile Ser Thr Gly
    1340                1345                1350

Cys Cys Gly Cys Cys Gly Cys Cys Cys Ala Cys Phe Ser Gly Cys
    1355                1360                1365

Cys Arg Gly Pro Arg Leu Gln Pro Tyr Glu Ala Phe Glu Lys Val
    1370                1375                1380

His Val Gln
    1385

<210> SEQ ID NO 40
<211> LENGTH: 1386
<212> TYPE: PRT
<213> ORGANISM: porcine epidemic diarrhea virus

```
<400> SEQUENCE: 40

Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Asn Thr Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ile Gly Glu Asn Gln Gly Val Asn Ser Thr
    50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
                100                 105                 110

Thr Asn Gly Asn Thr Asn Ala Thr Ala Arg Leu Arg Ile Cys Gln Phe
            115                 120                 125

Pro Ser Ile Lys Thr Leu Gly Pro Thr Ala Asn Asn Asp Val Thr Thr
    130                 135                 140

Gly Arg Asn Cys Leu Phe Asn Lys Ala Ile Pro Ala Tyr Met Ser Glu
145                 150                 155                 160

His Ser Val Val Gly Ile Thr Trp Asp Asn Asp Arg Val Thr Val Phe
                165                 170                 175

Ser Asp Lys Ile Tyr Tyr Phe Tyr Phe Lys Asn Asp Trp Ser Arg Val
                180                 185                 190

Ala Thr Lys Cys Tyr Asn Ser Gly Gly Cys Ala Met Gln Tyr Val Tyr
            195                 200                 205

Glu Pro Thr Tyr Tyr Met Leu Asn Val Thr Ser Ala Gly Glu Asp Gly
    210                 215                 220

Ile Ser Tyr Gln Pro Cys Thr Ala Asn Cys Ile Gly Tyr Ala Ala Asn
225                 230                 235                 240

Val Phe Ala Thr Glu Pro Asn Gly His Ile Pro Glu Gly Phe Ser Phe
                245                 250                 255

Asn Asn Trp Phe Leu Leu Ser Asn Asp Ser Thr Leu Val His Gly Lys
            260                 265                 270

Val Val Ser Asn Gln Pro Leu Leu Val Asn Cys Leu Leu Ala Ile Pro
    275                 280                 285

Lys Ile Tyr Gly Leu Gly Gln Phe Phe Ser Phe Asn Gln Thr Ile Asp
290                 295                 300

Gly Val Cys Asn Gly Ala Ala Val Gln Arg Ala Pro Glu Ala Leu Arg
305                 310                 315                 320

Phe Asn Ile Asn Asp Thr Ser Val Ile Leu Ala Glu Gly Ser Ile Val
                325                 330                 335

Leu His Thr Ala Leu Gly Thr Asn Phe Ser Phe Val Cys Ser Asn Ser
            340                 345                 350

Ser Gly Pro His Leu Ala Thr Phe Ala Ile Pro Leu Gly Ala Thr Gln
    355                 360                 365

Val Pro Tyr Tyr Cys Phe Leu Lys Val Asp Thr Tyr Asn Ser Thr Val
    370                 375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
                405                 410                 415
```

```
Gly Leu Leu Asp Ala Val Thr Ile Asn Phe Thr Gly His Gly Thr Asp
                420                 425                 430

Gly Asp Val Ser Gly Phe Trp Thr Ile Ala Ser Thr Asn Phe Val Asp
            435                 440                 445

Ala Leu Ile Glu Val Gln Gly Thr Ala Ile Gln Arg Ile Leu Tyr Cys
    450                 455                 460

Asp Asp Pro Val Ser Gln Leu Lys Cys Ser Gln Val Ala Phe Asp Leu
465                 470                 475                 480

Asp Asp Gly Phe Tyr Pro Ile Ser Ser Arg Asn Leu Leu Ser His Glu
                485                 490                 495

Gln Pro Ile Ser Phe Val Thr Leu Pro Ser Phe Asn Asp His Ser Phe
            500                 505                 510

Val Asn Ile Thr Val Ser Ala Ser Phe Gly Gly His Ser Gly Ala Asn
    515                 520                 525

Leu Ile Ala Ser Asp Thr Thr Ile Asn Gly Phe Ser Ser Phe Cys Val
530                 535                 540

Asp Thr Arg Gln Phe Thr Ile Ser Leu Phe Tyr Asn Val Thr Asn Ser
545                 550                 555                 560

Tyr Gly Tyr Val Ser Asn Ser Gln Asp Ser Asn Cys Pro Phe Thr Leu
                565                 570                 575

Gln Ser Val Asn Asp Tyr Leu Ser Phe Ser Lys Phe Cys Val Ser Thr
            580                 585                 590

Ser Leu Leu Ala Ser Ala Cys Thr Ile Asp Leu Phe Gly Tyr Pro Glu
    595                 600                 605

Phe Gly Ser Gly Val Lys Phe Thr Ser Leu Tyr Phe Gln Phe Thr Lys
610                 615                 620

Gly Glu Leu Ile Thr Gly Thr Pro Lys Pro Leu Glu Gly Val Thr Asp
625                 630                 635                 640

Val Ser Phe Met Thr Leu Asp Val Cys Thr Lys Tyr Thr Ile Tyr Gly
                645                 650                 655

Phe Lys Gly Glu Gly Ile Ile Thr Leu Thr Asn Ser Ser Phe Leu Ala
            660                 665                 670

Gly Phe Tyr Tyr Thr Ser Asp Ser Gly Gln Leu Leu Ala Phe Lys Asn
    675                 680                 685

Val Thr Ser Gly Ala Val Tyr Ser Val Thr Pro Cys Ser Phe Ser Glu
690                 695                 700

Gln Ala Ala Tyr Val Asp Asp Ile Val Gly Val Ile Ser Ser Leu
705                 710                 715                 720

Ser Ser Ser Thr Phe Asn Ser Thr Arg Glu Leu Pro Gly Phe Phe Tyr
                725                 730                 735

His Ser Asn Asp Gly Ser Asn Cys Thr Glu Pro Val Leu Val Tyr Ser
            740                 745                 750

Asn Ile Gly Val Cys Lys Ser Gly Ser Ile Gly Tyr Val Pro Ser Gln
    755                 760                 765

Ser Gly Gln Val Lys Ile Ala Pro Thr Val Thr Gly Asn Ile Ser Ile
770                 775                 780

Pro Thr Asn Phe Ser Met Ser Ile Arg Thr Glu Tyr Leu Gln Leu Tyr
785                 790                 795                 800

Asn Thr Pro Val Ser Val Asp Cys Ala Thr Tyr Val Cys Asn Gly Asn
                805                 810                 815

Ser Arg Cys Lys Gln Leu Leu Thr Gln Tyr Thr Ala Ala Cys Lys Thr
            820                 825                 830
```

-continued

```
Ile Glu Ser Ala Leu Gln Leu Ser Ala Arg Leu Glu Ser Val Glu Val
835                 840                 845

Asn Ser Met Leu Thr Ile Ser Glu Glu Ala Leu Gln Leu Ala Thr Ile
850                 855                 860

Ser Ser Phe Asn Gly Asp Gly Tyr Asn Phe Thr Asn Val Leu Gly Val
865                 870                 875                 880

Ser Val Tyr Asp Pro Ala Ser Gly Arg Val Val Gln Lys Arg Ser Phe
            885                 890                 895

Ile Glu Asp Ala Ala Phe Asn Lys Val Thr Asn Gly Leu Gly Thr
                900                 905                 910

Val Asp Glu Asp Tyr Lys Arg Cys Ser Asn Gly Arg Ser Val Ala Asp
            915                 920                 925

Leu Val Cys Ala Gln Tyr Tyr Ser Gly Val Met Val Leu Pro Gly Val
        930                 935                 940

Val Asp Ala Glu Lys Leu His Met Tyr Ser Ala Ser Leu Ile Gly Gly
945                 950                 955                 960

Met Val Leu Gly Gly Phe Thr Ser Ala Ala Ala Leu Pro Phe Ser Tyr
                965                 970                 975

Ala Val Gln Ala Arg Leu Asn Tyr Leu Ala Leu Gln Thr Asp Val Leu
            980                 985                 990

Gln Arg Asn Gln Gln Leu Leu Ala  Glu Ser Phe Asn Ser  Ala Ile Gly
            995                1000                1005

Asn Ile  Thr Ser Ala Phe Glu  Ser Val Lys Glu Ala   Ile Ser Gln
        1010                1015                1020

Thr Ser  Lys Gly Leu Asn Thr  Val Ala His Ala Leu   Thr Lys Val
        1025                1030                1035

Gln Glu  Val Val Asn Ser Gly  Ala Ala Leu Thr   Gln Leu Thr
        1040                1045                1050

Val Gln  Leu Gln His Asn Phe  Gln Ala Ile Ser Ser   Ser Ile Asp
        1055                1060                1065

Asp Ile  Tyr Ser Arg Leu Asp  Ile Leu Ser Ala Asp   Val Gln Val
        1070                1075                1080

Asp Arg  Leu Ile Thr Gly Arg  Leu Ser Ala Leu Asn   Ala Phe Val
        1085                1090                1095

Ala Gln  Thr Leu Thr Lys Tyr  Thr Glu Val Gln Ala   Ser Arg Lys
        1100                1105                1110

Leu Ala  Gln Gln Lys Val Asn  Glu Cys Val Lys Ser   Gln Ser Gln
        1115                1120                1125

Arg Tyr  Gly Phe Cys Gly Gly  Asp Gly Glu His Ile   Phe Ser Leu
        1130                1135                1140

Val Gln  Ala Ala Pro Gln Gly  Leu Leu Phe Leu His   Thr Val Leu
        1145                1150                1155

Val Pro  Gly Asp Phe Val Asp  Val Ile Ala Ile Ala   Gly Leu Cys
        1160                1165                1170

Val Asn  Asp Glu Ile Ala Leu  Thr Leu Arg Glu Pro   Gly Leu Val
        1175                1180                1185

Leu Phe  Thr His Glu Leu Gln  Asn His Thr Ala Thr   Glu Tyr Phe
        1190                1195                1200

Val Ser  Ser Arg Arg Met Phe  Glu Pro Arg Lys Pro   Thr Val Ser
        1205                1210                1215

Asp Phe  Val Gln Ile Glu Ser  Cys Val Val Thr Tyr   Val Asn Leu
        1220                1225                1230

Thr Arg  Asp Gln Leu Pro Asp  Val Ile Pro Asp Tyr   Ile Asp Val
```

-continued

```
                1235                1240                1245

Asn Lys Thr Leu Asp Glu Ile Leu Ala Ser Leu Pro Asn Arg Thr
        1250                1255                1260

Gly Pro Ser Leu Pro Leu Asp Val Phe Asn Ala Thr Tyr Leu Asn
    1265                1270                1275

Leu Thr Gly Glu Ile Ala Asp Leu Glu Gln Arg Ser Glu Ser Leu
1280                1285                1290

Arg Asn Thr Thr Glu Glu Leu Gln Ser Leu Ile Tyr Asn Ile Asn
        1295                1300                1305

Asn Thr Leu Val Asp Leu Glu Trp Leu Asn Arg Val Glu Thr Tyr
    1310                1315                1320

Ile Lys Trp Pro Trp Trp Val Trp Leu Ile Ile Phe Ile Val Leu
1325                1330                1335

Ile Phe Val Val Ser Leu Leu Val Phe Cys Cys Ile Ser Thr Gly
        1340                1345                1350

Cys Cys Gly Cys Cys Gly Cys Cys Ala Cys Phe Ser Gly Cys
    1355                1360                1365

Cys Arg Gly Pro Arg Leu Gln Pro Ala Glu Ala Phe Glu Lys Val
1370                1375                1380

Arg Val Gln
    1385
```

<210> SEQ ID NO 41
<211> LENGTH: 29
<212> TYPE: DNA
<213> ORGANISM: Artificial Sequence
<220> FEATURE:
<223> OTHER INFORMATION: probe sequence

<400> SEQUENCE: 41
acagagcctg tgttggtgta tagtaacat                                              29

<210> SEQ ID NO 42
<211> LENGTH: 23
<212> TYPE: DNA
<213> ORGANISM: Artificial Sequence
<220> FEATURE:
<223> OTHER INFORMATION: primer sequence

<400> SEQUENCE: 42
tatagtgggt gttatttcta gtt                                                    23

<210> SEQ ID NO 43
<211> LENGTH: 21
<212> TYPE: DNA
<213> ORGANISM: Artificial Sequence
<220> FEATURE:
<223> OTHER INFORMATION: primer sequence

<400> SEQUENCE: 43
gccaatactg ccagatttac a                                                      21

<210> SEQ ID NO 44
<211> LENGTH: 170
<212> TYPE: DNA
<213> ORGANISM: Artificial Sequence
<220> FEATURE:
<223> OTHER INFORMATION: ultramer sequence

<400> SEQUENCE: 44
tgatgatata gtgggtgtta tttctagttt gtctagctcc acttttaaca gtactaggga            60

```
gttgcctggt ttcttctacc attctaatga tggctctaat tgtacagagc ctgtgttggt    120
gtatagtaac ataggtgttt gtaaatctgg cagtattggc tatgtccat               170
```